United States Patent
Han et al.

(10) Patent No.: US 12,157,727 B2
(45) Date of Patent: Dec. 3, 2024

(54) SUBSTITUTED TETRAHYDROQUINOLIN COMPOUNDS AS INDOLEAMINE 2,3-DIOXYGENASE (IDO) INHIBITORS

(71) Applicant: Merck Sharp & Dohme LLC, Rahway, NJ (US)

(72) Inventors: Yongxin Han, Needham, MA (US); Yongqi Deng, Newton, MA (US); Hua Zhou, Acton, MA (US); Meredeth A. McGowan, Boston, MA (US); Hongjun Zhang, Boston, MA (US); Wensheng Yu, Edison, NJ (US); Brett A. Hopkins, Brownsburg, IN (US); Xavier Fradera, Boston, MA (US); Nunzio Sciammetta, Sudbury, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 554 days.

(21) Appl. No.: 17/615,718

(22) PCT Filed: Jun. 8, 2020

(86) PCT No.: PCT/US2020/036553
§ 371 (c)(1),
(2) Date: Dec. 1, 2021

(87) PCT Pub. No.: WO2020/251871
PCT Pub. Date: Dec. 17, 2020

(65) Prior Publication Data
US 2022/0235028 A1 Jul. 28, 2022

Related U.S. Application Data

(60) Provisional application No. 62/860,059, filed on Jun. 11, 2019.

(51) Int. Cl.
*C07D 401/06* (2006.01)
*C07D 401/08* (2006.01)
*C07D 471/04* (2006.01)
*C07D 519/00* (2006.01)

(52) U.S. Cl.
CPC ......... *C07D 401/06* (2013.01); *C07D 401/08* (2013.01); *C07D 471/04* (2013.01); *C07D 519/00* (2013.01)

(58) Field of Classification Search
CPC .. C07D 401/06; C07D 401/08; C07D 471/04; C07D 519/00
See application file for complete search history.

(56) References Cited

FOREIGN PATENT DOCUMENTS

| WO | 2019027855 A1 | 2/2019 |
|---|---|---|
| WO | 2019027856 A1 | 2/2019 |

OTHER PUBLICATIONS

Pubchem CID 79752129 and 79752128 (Year: 2014).*
Matsuno, Kenji et al., Novel candesartan derivatives as indoleamine 2,3-dioxygenase inhibitors, Med. Chem. Commun., 2012, 475-479, 3.
PubChem-CID-79752128, Create Date: Oct. 19, 2014 (Oct. 19, 2014), 11 pages.
PubChem-CID-79752129, Create Date: Oct. 19, 2014 (Oct. 19, 2014), 5 pages.
Ram, N. et al., Medicinal Chemistry of Drugs with Active Metabolites (N-, 0-, and S-desalkylation and Some Specific Oxidative Alterations, Current Medicinal Chemistry, 2012, 5683-5704, 19.

* cited by examiner

Primary Examiner — Matthew P Coughlin
Assistant Examiner — Ashli Ariana Chicks
(74) Attorney, Agent, or Firm — Kristi K. Harman; Catherine D. Fitch

(57) ABSTRACT

Disclosed herein is a compound of formula (I), or a pharmaceutically acceptable salt thereof: Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

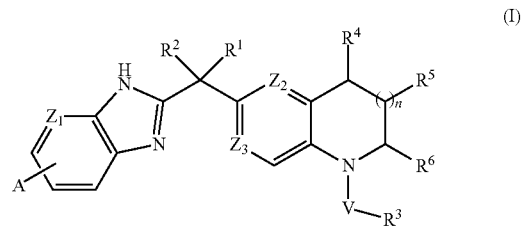

20 Claims, No Drawings

SUBSTITUTED TETRAHYDROQUINOLIN COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2020/036553, filed Jun. 8, 2020, which claims the benefit of U.S. Provisional Application No. 62/860,059, filed Jun. 11, 2019, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as Toxoplasma gondii and Chlamydia trachomatis. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immuno-inhibitory phenotype through up-regulation of IDO activity. A reduction in PBL proliferation upon treatment with inter-leukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair anti-tumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed during pregnancy, the genetically disparate mammalian conceptus survives despite what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by pre-immunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that co-expressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs co-express the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, serotonergic functions may also be affected because of reduced serotonin production (Wirleitner, et al., 2003, Curr. Med. Chem., 10: 1581-91).

Considering the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Compounds of formula I

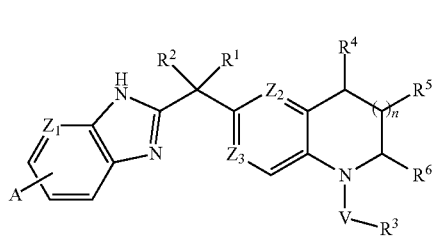

or the pharmaceutically acceptable salts, solvates, esters, and prodrugs thereof, are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

The invention is a compound of the formula

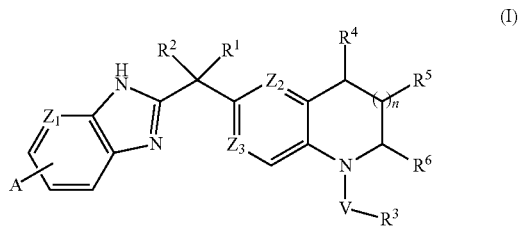

or pharmaceutically acceptable salts thereof, wherein

A is selected from H, halogen, CN, $C_{1-6}$alkyl optionally substituted with 1-3 halogens;

$Z_1$, $Z_2$ and $Z_3$ are each independently selected from $CR^8$ or N;

$R^8$, if present, is H, halogen, $C_{1-6}$alkyl, $OC_{0-6}$alkyl, or $NH_2$;

$R^1$ and $R^2$ are independently selected from H, $C_{1-6}$alkyl, $C_{3-6}$cycloalkyl, optionally substituted with $C_{3-6}$cycloalkyl, or $R^1$ and $R^2$, together with the carbon atom to which they are attached, optionally form $C_{3-6}$cycloalkyl, optionally substituted with $C_{3-6}$cycloalkyl;

V is absent, a bond, or selected from H, C(O), CONH, or $C_{3-6}$ heterocycle containing 1-4 nitrogen, wherein the $C_{3-6}$ heterocycle is optionally substituted with $CH_3$ or $CF_3$;

$R^3$ is selected from H, $C_{1-6}$alkyl, $C_{3-6}$cycloalkyl, $OC_{1-6}$alkyl, $OC_{3-6}$cycloalkyl, or $C_{3-10}$ heterocyclyl containing 1-4 nitrogen or oxygen, optionally substituted with halogen, $C_{1-6}$alkyl or $CF_3$;

$R^4$ and $R^5$ are independently selected from H, OH, halogen, or $C_{1-6}$alkyl;

$R^6$ is independently selected from H, OH, halogen, or $C_{1-6}$alkyl;

and is 0, 1, 2, 3, or 4.

An embodiment of the invention of the compound of formula (I), or a pharmaceutically acceptable salt thereof, is the compound of formula (Ia);

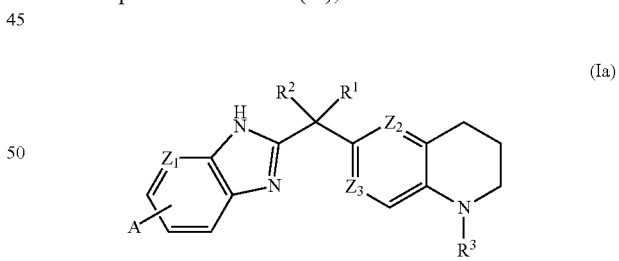

wherein:

A, $Z_1$, $Z_2$, $Z_3$, $R^1$, $R^2$, and $R^3$ are as described herein.

In a subembodiment of the invention of formula Ia, A is selected from H, halogen, CN, $C_{1-6}$alkyl or $CF_3$.

In a further subembodiment of the invention of formula Ia, A is selected from H, halogen, CN or $CF_3$.

In a further subembodiment of the invention of formula Ia, A is H.

In a further subembodiment of the invention of formula Ia, A is halogen.

In a further subembodiment of the invention of formula Ia, A is Cl.

In a further subembodiment of the invention of formula Ia,
A is CN.

In a further subembodiment of the invention of formula Ia,
A is $CF_3$.

In a subembodiment of the invention of formula Ia, $Z_1$, $Z_2$, and $Z_3$ are each independently selected from CH and N.

In a further subembodiment of the invention of formula Ia,
$Z_1$ is CH.

In a further subembodiment of the invention of formula Ia,
$Z_1$ is N.

In a further subembodiment of the invention of formula Ia,
$Z_2$ is CH.

In a further subembodiment of the invention of formula Ia,
$Z_2$ is N.

In a further subembodiment of the invention of formula Ia,
$Z_3$ is CH.

In a further subembodiment of the invention of formula Ia,
$Z_3$ is N.

In a further subembodiment of the invention of formula Ia,
$Z_1$, $Z_2$ and $Z_3$ are CH.

In a further subembodiment of the invention of formula Ia,
$Z_1$, $Z_2$ and $Z_3$ are N.

In a further subembodiment of the invention of formula Ia,
$Z_1$ is N, $Z_2$ is N, and $Z_3$ is CH.

In a further subembodiment of the invention of formula Ia,
$Z_1$ is N, $Z_2$ is CH, and $Z_3$ is N.

In a further subembodiment of the invention of formula Ia,
$Z_1$ is CH, $Z_2$ is N, and $Z_3$ is N.

In a further subembodiment of the invention of formula Ia,
$Z_1$ is CH, $Z_2$ is CH, and $Z_3$ is N.

In a further subembodiment of the invention of formula Ia,
$Z_1$ is CH, $Z_2$ is N, and $Z_3$ is CH.

In a further subembodiment of the invention of formula Ia,
$Z_1$ is N, $Z_2$ is CH, and $Z_3$ is CH.

In a subembodiment of the invention of formula Ia, $R^1$ and $R^2$ are independently selected from H, $C_{1-6}$alkyl, $C_{3-6}$cycloalkyl, optionally substituted with $C_{3-6}$cycloalkyl, or $R^1$ and $R^2$, together with the carbon atom to which they are attached, optionally form $C_{3-6}$cycloalkyl optionally substituted with $C_{3-6}$cycloalkyl.

In a further subembodiment of the invention of formula Ia, $R^1$ and $R^2$, together with the carbon atom to which they are attached, combine to form a compound selected from the group consisting of spirocyclopropyl, cyclobutyl, cyclopentyl and cyclohexyl.

In a further subembodiment of the invention of formula Ia, $R^1$ and $R^2$ combine to form spirocyclopropyl.

In a further subembodiment of the invention of formula Ia, $R^1$ and $R^2$ combine to form cyclobutyl.

In a further subembodiment of the invention of formula Ia, $R^1$ and $R^2$ combine to form cyclopentyl.

In a further subembodiment of the invention of formula Ia, $R^1$ and $R^2$ combine to form cyclohexyl.

In a further subembodiment of the invention of formula Ia, $R^1$ and $R^2$ combine to form spirohexane.

In a subembodiment of the invention of formula Ia, $R^3$ is selected from H, $C_{1-6}$alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, $C_{1-6}$alkyl or $CF_3$.

In a further subembodiment of the invention of formula Ia, $R^3$ is selected from H, cyclopropyl, tetrahydrofuran, $OCH_3$, O-cyclopropyl, tetrahydropyran, $OCH_2CH_3$, or phenyl optionally substituted with halogen.

In a further subembodiment of the invention of formula Ia, $R^3$ is selected from $C_{3-10}$ heterocyclyl containing 1-2 nitrogen optionally substituted with halogen, $C_{1-6}$alkyl, or $CF_3$.

In a further subembodiment of the invention of formula Ia, $R^3$ is selected from $C_{3-6}$ heterocyclyl containing 1-2 nitrogen optionally substituted with Cl, $CH_3$, or $CF_3$.

In a further subembodiment of the invention of formula Ia, $R^3$ is hydrogen or $C_{1-3}$alkyl.

Another embodiment of the invention of the compound of formula (I), or a pharmaceutically acceptable salt thereof, is the compound of formula (Ib);

(Ib)

wherein:
A, $Z_1$, $Z_2$, $Z_3$, $R^1$, $R^2$, and $R^3$ are as described herein.

In a subembodiment of the invention of formula Ib, A is selected from hydrogen, halogen, CN, $C_{1-6}$alkyl, or $CF_3$.

In a further subembodiment of the invention of formula Ib, A is selected from H, halogen, CN, $CH_3$, or $CF_3$. In a further subembodiment of the invention of formula Ib, A is H.

In a further subembodiment of the invention of formula Ib, A is halogen.

In a further subembodiment of the invention of formula Ib, A is Cl.

In a further subembodiment of the invention of formula Ib, A is CN.

In a further subembodiment of the invention of formula Ib, A is $CF_3$.

In a subembodiment of the invention of formula Ib, $Z_1$, $Z_2$, and $Z_3$ are each independently selected from CH and N.

In a further subembodiment of the invention of formula Ib,
$Z_1$ is CH.

In a further subembodiment of the invention of formula Ib,
$Z_1$ is N.

In a further subembodiment of the invention of formula Ib,
$Z_2$ is CH.

In a further subembodiment of the invention of formula Ib,
$Z_2$ is N.

In a further subembodiment of the invention of formula Ib,
$Z_3$ is CH.

In a further subembodiment of the invention of formula Ib,
$Z_3$ is N.

In a further subembodiment of the invention of formula Ib,
$Z_1$, $Z_2$ and $Z_3$ are CH.

In a further subembodiment of the invention of formula Ib,
$Z_1$, $Z_2$ and $Z_3$ are N.

In a further subembodiment of the invention of formula Ib,
$Z_1$ is N, $Z_2$ is N, and $Z_3$ is CH.

In a further subembodiment of the invention of formula Ib,
$Z_1$ is N, $Z_2$ is CH, and $Z_3$ is N.

In a further subembodiment of the invention of formula Ib,
$Z_1$ is CH, $Z_2$ is N, and $Z_3$ is N.

In a further subembodiment of the invention of formula Ib,
$Z_1$ is CH, $Z_2$ is CH, and $Z_3$ is N.

In a further subembodiment of the invention of formula Ib,
$Z_1$ is CH, $Z_2$ is N, and $Z_3$ is CH.

In a further subembodiment of the invention of formula Ib, $Z_1$ is N, $Z_2$ is CH, and $Z_3$ is CH.

In a subembodiment of the invention of formula Ib, $R^1$ and $R^2$ are independently selected from H, $C_{1-6}$alkyl, $C_{3-6}$cycloalkyl, optionally substituted with $C_{3-6}$cycloalkyl, or $R^1$ and $R^2$, together with the carbon atom to which they are attached, optionally form $C_{3-6}$cycloalkyl, optionally substituted with $C_{3-6}$cycloalkyl.

In a further subembodiment of the invention of formula Ib, $R^1$ and $R^2$ combine to form a compound selected from the group consisting of spirocyclopropyl, cyclobutyl, cyclopentyl and cyclohexyl.

In a further subembodiment of the invention of formula Ib, $R^1$ and $R^2$ combine to form spirocyclopropyl.

In a further subembodiment of the invention of formula Ib, $R^1$ and $R^2$ combine to form cyclobutyl.

In a further subembodiment of the invention of formula Ib, $R^1$ and $R^2$ combine to form cyclopentyl.

In a further subembodiment of the invention of formula Ib, $R^1$ and $R^2$ combine to form cyclohexyl.

In a further subembodiment of the invention of formula Ia, $R^1$ and $R^2$ combine to form spirohexane.

In a subembodiment of the invention of formula Ib, $R^3$ is selected from H, $C_{1-6}$ alkyl, $C_{3-6}$cycloalkyl, $OC_{1-6}$alkyl, $OC_{3-6}$cycloalkyl, or $C_{3-10}$ heterocyclyl containing 1-4 nitrogen or oxygen, optionally substituted with halogen, $C_{1-6}$alkyl or $CF_3$.

In a further subembodiment of the invention of formula Ib, $R^3$ is selected from H, cyclopropyl, tetrahydrofuran, $OCH_3$, O-cyclopropyl, tetrahydropyran, $OCH_2CH_3$, or phenyl optionally substituted with halogen.

Another embodiment of the invention of the compound of formula (I), or a pharmaceutically acceptable salt thereof, is the compound of formula (Ic);

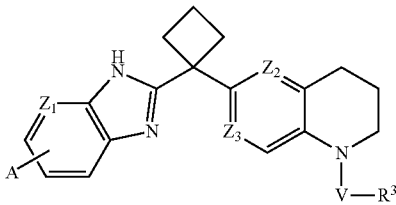

(Ic)

wherein:
A, $Z_1$, $Z_2$, $Z_3$, V, and $R^3$ are as described herein.

In a subembodiment of the invention of formula Ic, A is selected from H, halogen, CN, or $CF_3$.

In a further subembodiment of the invention of formula Ic, A is H.

In a further subembodiment of the invention of formula Ic, A is $CF_3$.

In a further subembodiment of the invention of formula Ic, A is halogen.

In a further subembodiment of the invention of formula Ic, A is Cl.

In a further subembodiment of the invention of formula Ic, A is CN.

In a subembodiment of the invention of formula Ic, $Z_1$, $Z_2$, and $Z_3$ are each independently selected from CH and N.

In a further subembodiment of the invention of formula Ic, $Z_1$ is CH.

In a further subembodiment of the invention of formula Ic, $Z_1$ is N.

In a further subembodiment of the invention of formula Ic, $Z_2$ is CH.

In a further subembodiment of the invention of formula Ic, $Z_2$ is N.

In a further subembodiment of the invention of formula Ic, $Z_3$ is CH.

In a further subembodiment of the invention of formula Ic, $Z_3$ is N.

In a further subembodiment of the invention of formula Ic, $Z_1$, $Z_2$ and $Z_3$ are CH.

In a further subembodiment of the invention of formula Ic, $Z_1$, $Z_2$ and $Z_3$ are N.

In a further subembodiment of the invention of formula Ic, $Z_1$ is N, $Z_2$ is N, and $Z_3$ is CH.

In a further subembodiment of the invention of formula Ic, $Z_1$ is N, $Z_2$ is CH, and $Z_3$ is N.

In a further subembodiment of the invention of formula Ic, $Z_1$ is CH, $Z_2$ is N, and $Z_3$ is N.

In a further subembodiment of the invention of formula Ic, $Z_1$ is CH, $Z_2$ is CH, and $Z_3$ is N.

In a further subembodiment of the invention of formula Ic, $Z_1$ is CH, $Z_2$ is N, and $Z_3$ is CH.

In a further subembodiment of the invention of formula Ic, $Z_1$ is N, $Z_2$ is CH, and $Z_3$ is CH.

In a subembodiment of the invention of formula Ic, V is absent, a bond, or selected from H, C(O), CONH, or $C_{3-6}$ heterocycle containing 1-4 nitrogen, optionally substituted with $CH_3$ or $CF_3$.

In a subembodiment of the invention of formula Ic, V is pyridine or pyrimidine.

In a further subembodiment of the invention of formula Ic, V is C(O).

In a further subembodiment of the invention of formula Ic, V is a bond.

In a subembodiment of the invention of formula Ic, $R^3$ is selected from H, $C_{1-6}$alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, wherein the $C_{1-6}$alkyl is optionally substituted with $CF_3$.

In a further subembodiment of the invention of formula Ic, $R^3$ is selected from H, cyclopropyl, tetrahydrofuran, $OCH_3$, O-cyclopropyl, tetrahydropyran, $OCH_2CH_3$, or phenyl optionally substituted with halogen.

In a further subembodiment of the invention of formula Ic, $R^3$ is selected from $C_{3-10}$heterocyclyl containing 1-2 nitrogen optionally substituted with halogen, $C_{1-6}$alkyl, or $CF_3$.

In a further subembodiment of the invention of formula Ic, $R^3$ is selected from $C_{3-6}$heterocyclyl containing 1-2 nitrogen optionally substituted with Cl, $CH_3$, or $CF_3$.

Another embodiment of the invention of the compound of formula (I), or a pharmaceutically acceptable salt thereof, is the compound of formula (Id);

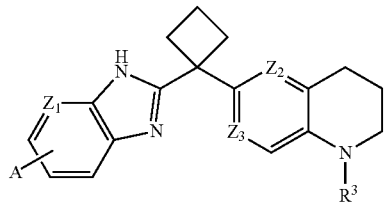

(Id)

wherein:
A, $Z_1$, $Z_2$, $Z_3$, and $R^3$ are as described herein.

In a subembodiment of the invention of formula Id, A is selected from H, halogen, CN, or $CF_3$.

In a further subembodiment of the invention of formula Id, A is H.

In a further subembodiment of the invention of formula Id, A is $CF_3$.

In a further subembodiment of the invention of formula Id, A is halogen.

In a further subembodiment of the invention of formula Id, A is Cl.

In a further subembodiment of the invention of formula Id, A is CN.

In a subembodiment of the invention of formula Id, $Z_1$, $Z_2$, and $Z_3$ are each independently selected from CH and N.

In a further subembodiment of the invention of formula Id, $Z_1$ is CH.

In a further subembodiment of the invention of formula Id, $Z_1$ is N.

In a further subembodiment of the invention of formula Id, $Z_2$ is CH.

In a further subembodiment of the invention of formula Id, $Z_2$ is N.

In a further subembodiment of the invention of formula Id, $Z_3$ is CH.

In a further subembodiment of the invention of formula Id, $Z_3$ is N.

In a further subembodiment of the invention of formula Id, $Z_1$, $Z_2$ and $Z_3$ are CH.

In a further subembodiment of the invention of formula Id, $Z_1$, $Z_2$ and $Z_3$ are N.

In a further subembodiment of the invention of formula Id, $Z_1$ is N, $Z_2$ is N, and $Z_3$ is CH.

In a further subembodiment of the invention of formula Id, $Z_1$ is N, $Z_2$ is CH, and $Z_3$ is N.

In a further subembodiment of the invention of formula Id, $Z_1$ is CH, $Z_2$ is N, and $Z_3$ is N.

In a further subembodiment of the invention of formula Id, $Z_1$ is CH, $Z_2$ is CH, and $Z_3$ is N.

In a further subembodiment of the invention of formula Id, $Z_1$ is CH, $Z_2$ is N, and $Z_3$ is CH.

In a further subembodiment of the invention of formula Id, $Z_1$ is N, $Z_2$ is CH, and $Z_3$ is CH.

In a subembodiment of the invention of formula Id, $R^3$ is selected from H, $C_{1-6}$alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, $C_{1-6}$alkyl or $CF_3$.

In a further subembodiment of the invention of formula Id, $R^3$ is selected from H, cyclopropyl, tetrahydrofuran, $OCH_3$, O-cyclopropyl, tetrahydropyran, $OCH_2CH_3$, or phenyl optionally substituted with halogen.

In a further subembodiment of the invention of formula Id, $R^3$ is pyridine or pyrimidine.

Another embodiment of the invention of the compound of formula (I), or a pharmaceutically acceptable salt thereof, is the compound of formula (Ie);

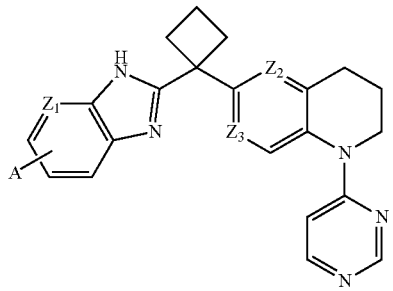

(Ie)

wherein:

A, $Z_1$, $Z_2$, and $Z_3$ are as described herein.

In a subembodiment of the invention of formula Ie, A is selected from H, halogen, CN, or $CF_3$.

In a further subembodiment of the invention of formula Ie, A is H.

In a further subembodiment of the invention of formula Ie, A is $CF_3$.

In a further subembodiment of the invention of formula Ie, A is halogen.

In a further subembodiment of the invention of formula Ie, A is Cl.

In a further subembodiment of the invention of formula Ie, A is CN.

In a subembodiment of the invention of formula Id, $Z_1$, $Z_2$, and $Z_3$ are each independently selected from CH and N.

In a further subembodiment of the invention of formula Ie, $Z_1$ is CH.

In a further subembodiment of the invention of formula Ie, $Z_1$ is N.

In a further subembodiment of the invention of formula Ie, $Z_2$ is CH.

In a further subembodiment of the invention of formula Ie, $Z_2$ is N.

In a further subembodiment of the invention of formula Ie, $Z_3$ is CH.

In a further subembodiment of the invention of formula Ie, $Z_3$ is N.

In a further subembodiment of the invention of formula Ie, $Z_1$, $Z_2$ and $Z_3$ are CH.

In a further subembodiment of the invention of formula Ie, $Z_1$, $Z_2$ and $Z_3$ are N.

In a further subembodiment of the invention of formula Ie, $Z_1$ is N, $Z_2$ is N, and $Z_3$ is CH.

In a further subembodiment of the invention of formula Ie, $Z_1$ is N, $Z_2$ is CH, and $Z_3$ is N.

In a further subembodiment of the invention of formula Ie, $Z_1$ is CH, $Z_2$ is N, and $Z_3$ is N.

In a further subembodiment of the invention of formula Ie, $Z_1$ is CH, $Z_2$ is CH, and $Z_3$ is N.

In a further subembodiment of the invention of formula Ie, $Z_1$ is CH, $Z_2$ is N, and $Z_3$ is CH.

In a further subembodiment of the invention of formula Ie, $Z_1$ is N, $Z_2$ is CH, and $Z_3$ is CH.

Another embodiment of the invention of the compound of formula (I), or a pharmaceutically acceptable salt thereof, is the compound of formula (If);

(If)

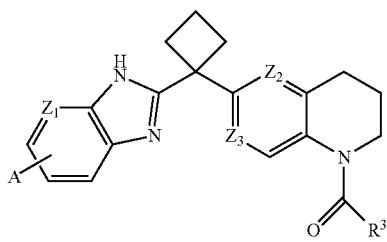

wherein:

A, $Z_1$, and $R^3$ are as described herein.

In a subembodiment of the invention of formula If, A is selected from H, halogen, CN, or $CF_3$.

In a further subembodiment of the invention of formula If, A is H.

In a further subembodiment of the invention of formula If, A is $CF_3$.

In a further subembodiment of the invention of formula If, A is halogen.

In a further subembodiment of the invention of formula If, A is Cl.

In a further subembodiment of the invention of formula If, A is CN.

In a subembodiment of the invention of formula If, $Z_1$ is CH or N.

In a further subembodiment of the invention of formula If, $Z_1$ is CH.

In a further subembodiment of the invention of formula If, $Z_1$ is N.

In a subembodiment of the invention of formula If, $R^3$ is selected from H, $C_{1-6}$alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, $C_{1-6}$alkyl or $CF_3$.

In a further subembodiment of the invention of formula If, $R^3$ is selected from H, cyclopropyl, tetrahydrofuran, $OCH_3$, O-cyclopropyl, tetrahydropyran, $OCH_2CH_3$, or phenyl optionally substituted with halogen.

Another embodiment of the invention of the compound of formula (I), or a pharmaceutically acceptable salt thereof, is the compound of formula (Ig):

(Ig)

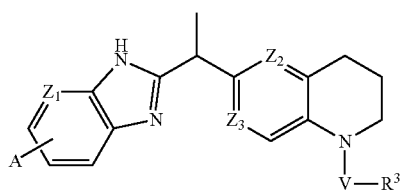

wherein:

A, $Z_1$, $Z_2$, V, and $R^3$ are as described herein.

In a subembodiment of the invention of formula Ig, A is selected from H, halogen, CN, or $CF_3$.

In a further subembodiment of the invention of formula Ig, A is H.

In a further subembodiment of the invention of formula Ig, A is $CF_3$.

In a further subembodiment of the invention of formula Ig, A is halogen.

In a further subembodiment of the invention of formula Ig, A is Cl.

In a further subembodiment of the invention of formula Ig, A is CN.

In a subembodiment of the invention of formula Ig, $Z_1$ is CH or N.

In a further subembodiment of the invention of formula Ig, $Z_1$ is CH.

In a further subembodiment of the invention of formula Ig, $Z_1$ is N.

In a subembodiment of the invention of formula Ig, $Z_2$ is CH or N.

In a further subembodiment of the invention of formula Ig, $Z_2$ is CH.

In a further subembodiment of the invention of formula Ig, $Z_2$ is N.

In a further subembodiment of the invention of formula Ig, V is absent, a bond, or selected from H, C(O), CONH, or $C_{3-6}$ heterocycle containing 1-4 nitrogen, wherein the $C_{3-6}$ heterocycle is optionally substituted with $CH_3$ or $CF_3$.

In a further subembodiment of the invention of formula Ig, V is C(O).

In a further subembodiment of the invention of formula Ig, V is H.

In a subembodiment of the invention of formula Ig, $R^3$ is selected from H, $C_{1-6}$alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, $C_{1-6}$alkyl or $CF_3$.

In a further subembodiment of the invention of formula Ig, $R^3$ is selected from H, cyclopropyl, tetrahydrofuran, $OCH_3$, O-cyclopropyl, tetrahydropyran, $OCH_2CH_3$, or phenyl optionally substituted with halogen.

Another embodiment of the invention of the compound of formula (I), or a pharmaceutically acceptable salt thereof, is the compound of formula (Ih):

(Ih)

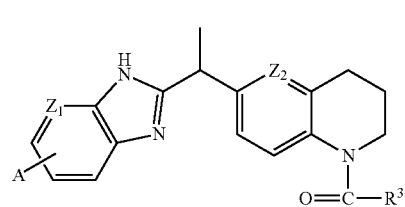

wherein:

A, $Z_1$, $Z_2$, and $R^3$ are as described herein.

In a subembodiment of the invention of formula Ih, A is selected from H, $CF_3$, halogen and CN.

In a further subembodiment of the invention of formula Ih, A is H.

In a further subembodiment of the invention of formula Ih, A is $CF_3$.

In a further subembodiment of the invention of formula Ih, A is halogen.

In a further subembodiment of the invention of formula Ih, A is Cl.

In a further subembodiment of the invention of formula Ih, A is CN.

In a subembodiment of the invention of formula Ih, $Z_1$ is CH or N.

In a further subembodiment of the invention of formula Ih, $Z_1$ is CH.

In a further subembodiment of the invention of formula Ih, $Z_1$ is N.

In a subembodiment of the invention of formula Ih, $Z_2$ is CH or N.

In a further subembodiment of the invention of formula Ih, $Z_2$ is CH.

In a further subembodiment of the invention of formula Ih, $Z_2$ is N.

In a subembodiment of the invention of formula Ih, $R^3$ is selected from H, $C_{1-6}$ alkyl, $C_{3-6}$cycloalkyl, $OC_{1-6}$alkyl, $OC_{3-6}$cycloalkyl, or $C_{3-10}$heterocyclyl containing 1-4 nitrogen or oxygen, optionally substituted with halogen, $C_{1-6}$alkyl or $CF_3$.

In a further subembodiment of the invention of formula Ih, $R^3$ is selected from H, cyclopropyl, tetrahydrofuran, $OCH_3$, O-cyclopropyl, tetrahydropyran, $OCH_2CH_3$, or phenyl optionally substituted with halogen.

In an embodiment of the invention, the compound is

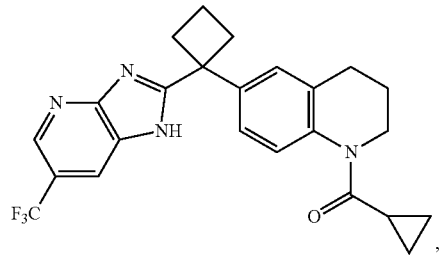

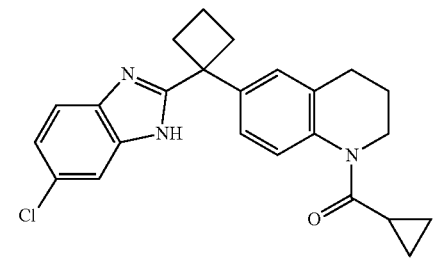

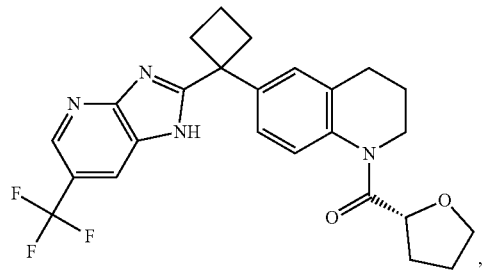

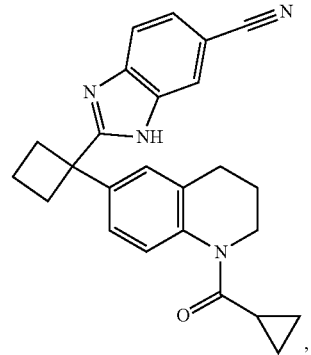

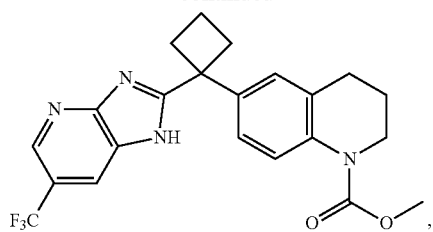

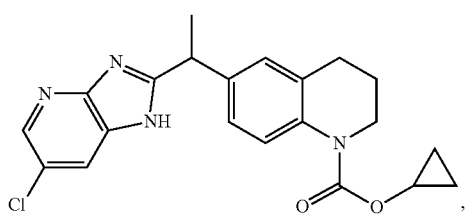

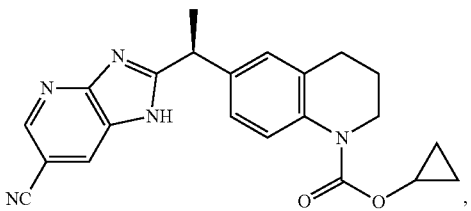

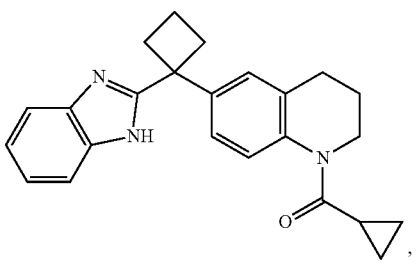

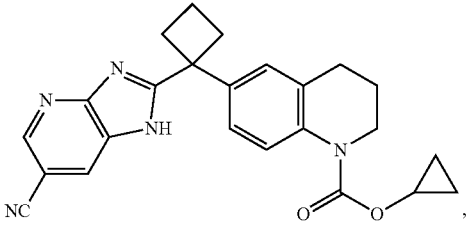

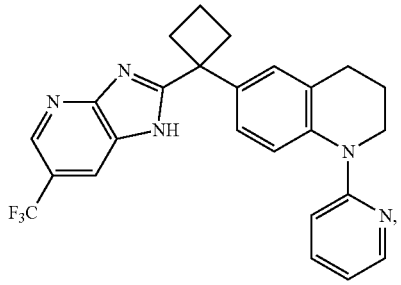

15
-continued
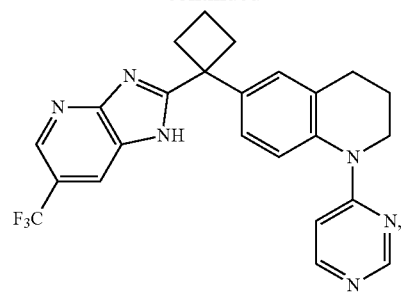
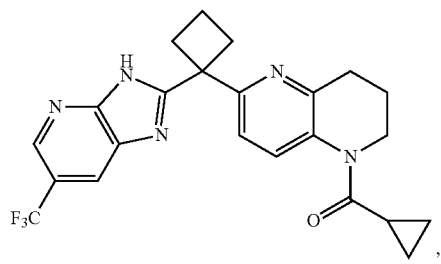
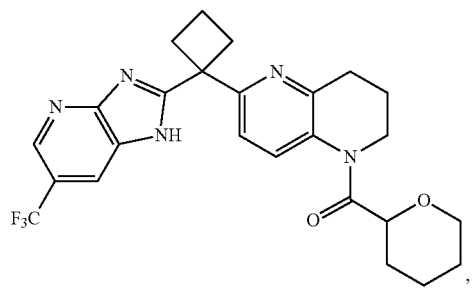
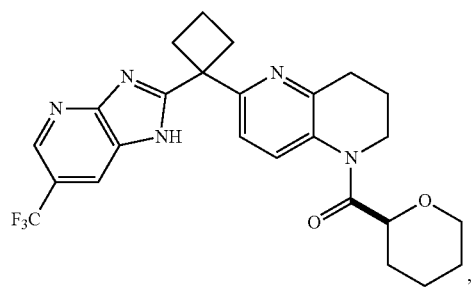
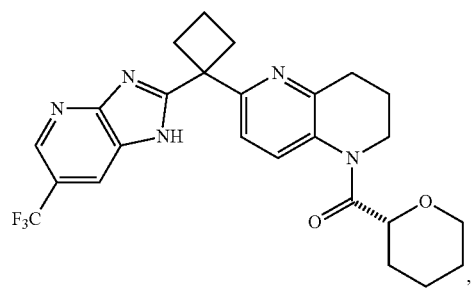
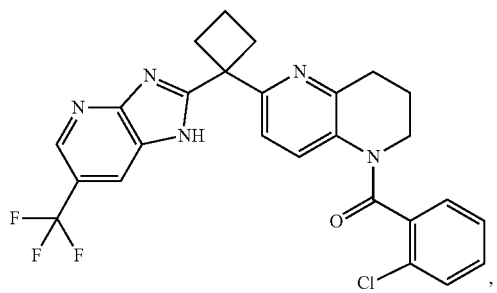
16
-continued
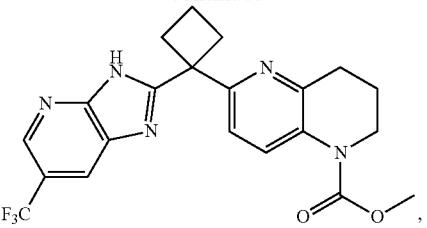
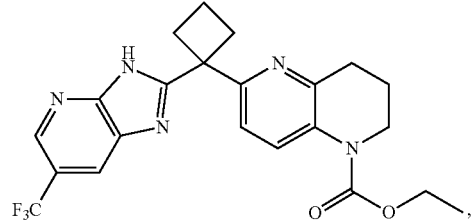
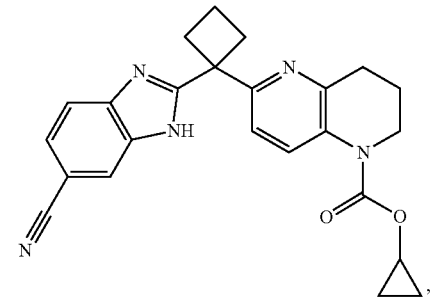
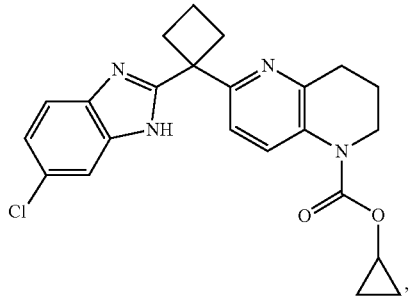
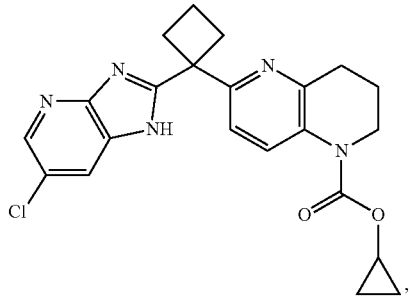
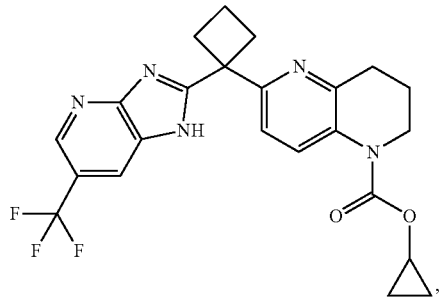

-continued
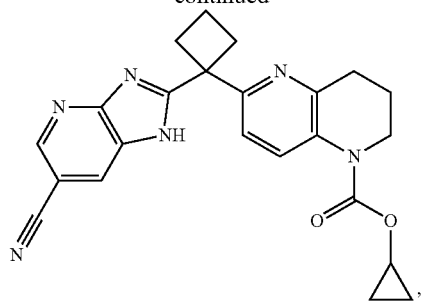
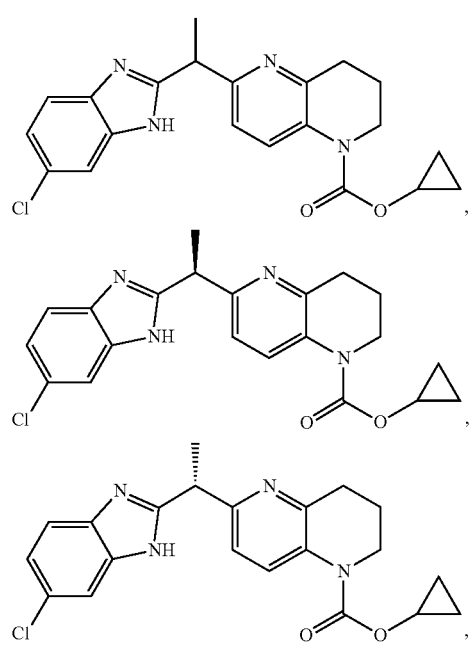
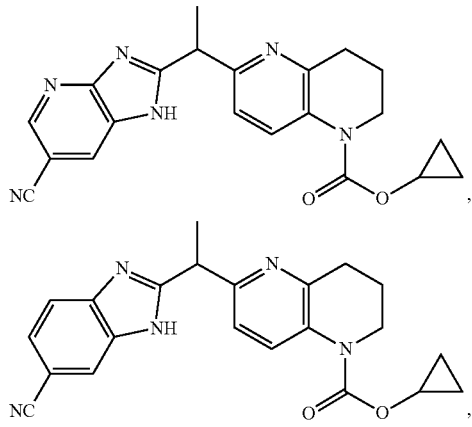
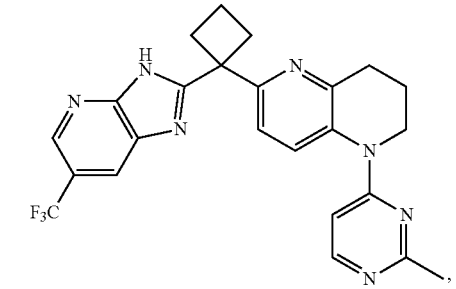
-continued
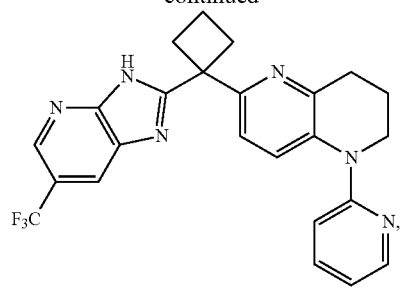
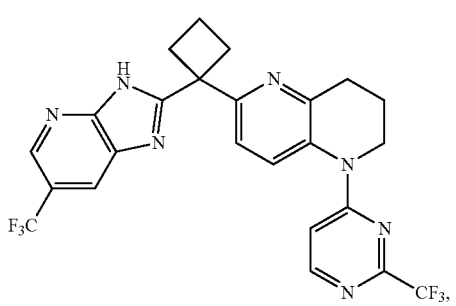
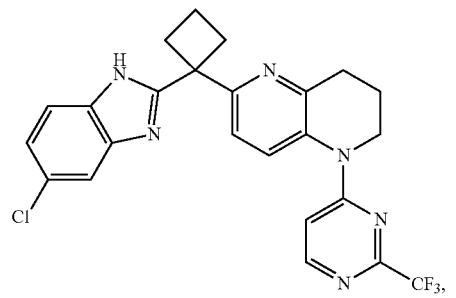
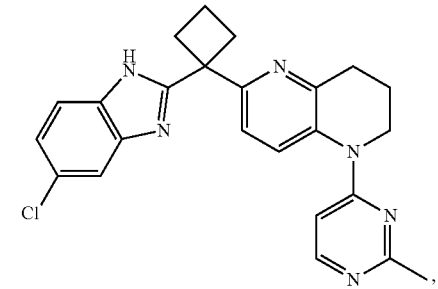
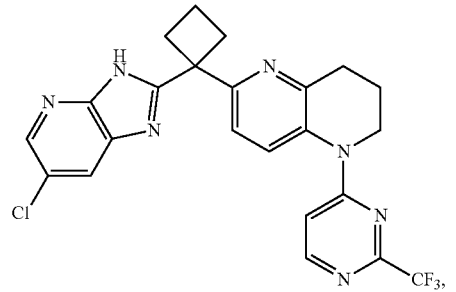

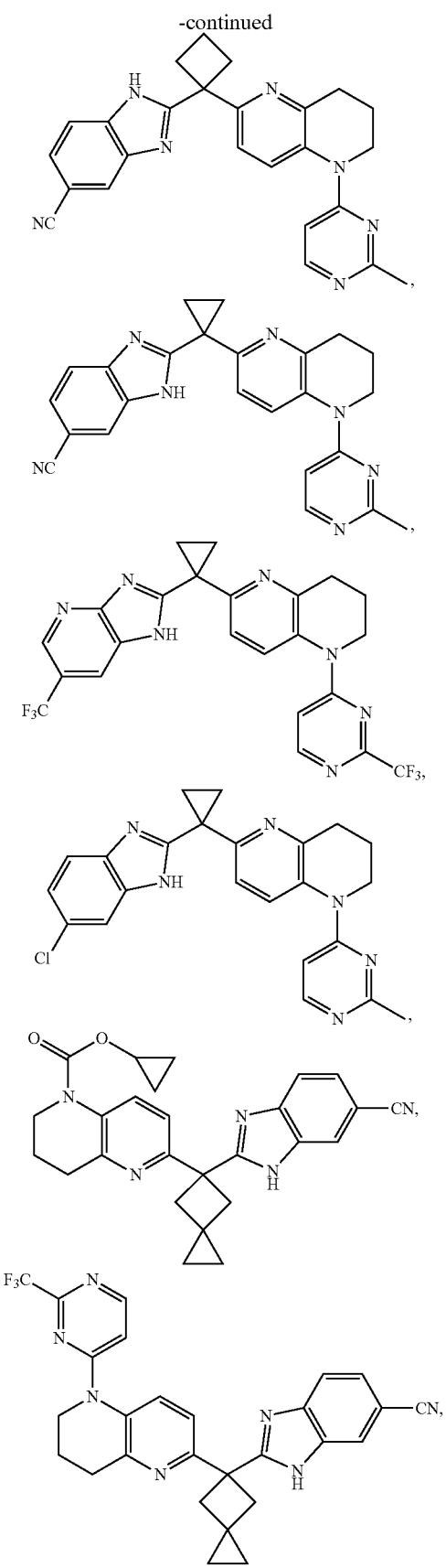

or a pharmaceutically acceptable salt thereof.

In another embodiment of the invention, a compound disclosed herein is selected from the group consisting of the compound exemplified in Examples 1 to 41, or a pharmaceutically acceptable salt thereof.

In one embodiment, the present invention is a composition comprising a compound of formula I, Ia, Ib, Ic, Id, Ie, If, Ig, or Ih, and at least one pharmaceutically acceptable carrier.

In another embodiment, the present invention is a method of treating cancer, viral infection, depression, a neurodegenerative disorder, trauma, age-related cataracts, organ transplant rejection, or an autoimmune disease comprising administering to a patient in need thereof a composition of formula I, Ia, Ib, Ic, Id, Ie, If, Ig, or Ih.

In another embodiment, the present invention is the use of a compound of formula I, Ia, Ib, Ic, Id, Ie, If, Ig, or Ih, or a pharmaceutically acceptable salt thereof, in the manufacture of a medicament for treating cancer, viral infection, depression, a neurodegenerative disorder, trauma, age-related cataracts, organ transplant rejection, or an autoimmune disease.

In another embodiment, the present invention includes compounds of formula I, Ia, Ib, Ic, Id, Ie, If, Ig, or Ih, for use in the treatment of cancer, viral infection, depression, a neurodegenerative disorder, trauma, age-related cataracts, organ transplant rejection, or an autoimmune disease.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tent-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Cycloalkyl" refers to a non-aromatic ring system comprising from about 3 to about 6 ring carbon atoms. Non-limiting examples of monocyclic cycloalkyl include cyclopropyl, cyclobutyl, cyclopentyl. Non-limiting examples of cycloalkyl additionally include bicyclic spiro-cycloalkyl including spirohexane

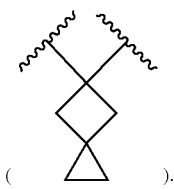

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

'H' refers to hydrogen.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

"Celite®" (Fluka) diatomite is diatomaceous earth and can be referred to as "celite".

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers-Diastereomers-Geometric Isomers-Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

Regarding stereoisomers, a compound disclosed herein may have one or more asymmetric carbon atom and may occur as mixtures (such as a racemic mixture) or as individual enantiomers or diastereomers. All such isomeric forms are included herein, including mixtures thereof If a compound disclosed herein contains a double bond, the substituent may be in the E or Z configuration. If a compound disclosed herein contains a disubstituted cycloalkyl, the cycloalkyl substituent may have a cis- or trans- configuration. All tautomeric forms are also intended to be included.

Any asymmetric atom (e.g., carbon) of a compound disclosed herein, can be present in racemic mixture or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated based on the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. A basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —CH$_2$C(O)— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2$H (i.e., Deuterium or "D") $^3$H , $^{11}$C, $^{13}$C, $^{14}$C, $^{13}$N, $^{15}$N, $^{15}$O, $^{17}$O, $^{18}$O, $^{32}$P, $^{35}$S, $^{18}$F, $^{123}$I, $^{125}$I and $^{36}$Cl. The invention includes various isotopically labeled compounds as defined herein, for example those into which radioactive isotopes, such as $^3$H and $^{14}$C, or those into which non-radioactive isotopes, such as $^2$H and $^{13}$C are present. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. Substitution with positron emitting isotopes, such as $^{11}$C, $^{15}$O and $^{13}$N, may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared using a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein, and other active agents will generally also be within the aforementioned range, but in each case, an effective dose of each active agent should be used. In such combinations, the compound disclosed herein, and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)-((R)-1-(4-(4-Fluoro-2-methyl-1H-indol -5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following examples are intended to be illustrative only and not limiting in any way. Abbreviations used are those conventional in the art or the following.

ACN acetonitrile
AcOH Acetic Acid
aq. aqueous
Boc tert-butoxycarbonyl
Boc2O Di-tent-butyl dicarbonate
° C. degree Celsius
Ca circa (about)
CPhos Pd G4 [(2-Dicyclohexylphosphino-2',6'-bis(N,N-dimethylamino) -1,1'-biphenyl)-2-(2'-methylamino-1,1'-biphenyl)] palladium(II) methanesulfonate
CPME Cyclopentyl methyl ether
DAST (Dimethylamino)sulfur trifluoride
DCM dichloromethane
DIEA or DIPEA N,N-diisopropylethylamine
DMA dimethylamine
DMF N,N-dimethylformamide
DMAP 4-Dimethylaminopyridine
DMSO dimethylsulfoxide
dppf 1,1'-bis(diphenylphosphino)ferrocene
EDC N-(3-Dimethylaminopropyl)-N'-ethylcarbodiimide hydrochloride
EDC1 N-(3-Dimethylaminopropyl)-N'-ethylcarbodiimide hydrochloride
EI electron ionization
EtOAc ethyl acetate
EtOH ethanol
g gram
h hour(s)
HATU 1-[bis(dimethylamino)methylene]-1H-1,2,3-triazolo[4,5-b]pyridinium 3-oxid-hexafluorophosphate
HCl hydrochloric acid
HPLC high pressure liquid chromatography
kg kilogram
L liter
LC liquid chromatography
LCMS liquid chromatography and mass spectrometry
mCPBA 3-chloroperbenzoic acid
MeOH methanol
MS mass spectrometry
MTBE methyl tent-butyl ether
min minutes
mL milliliter(s)
m/z mass to charge ratio
nm nanometer
nM nanomolar
N normal
NBS N-Bromosuccinimide
NiXantPhos G4 Methanesulfonato [4,6-Bis(diphenylphosphino)phenoxazine-(2'-methylamino-1, 1'-biphenyl-2-yl)] palladium(II)
P(t-Bu)3 Pd G2 Chloro[(tri-tert-butylphosphine)-2-(2-aminobiphenyl)] palladium(II)
Pd/C Palladium on carbon
Pd$_2$(dba)$_3$ Tris(dibenzylideneacetone)dipalladium(0)
Pd(dppf)2C12 [1,1'-Bis(diphenylphosphino)ferrocene]dichloropalladium(II)
PdCl$_2$(dtbpf) [1,1'-Bi s(di-tert-butylphosphino)ferrocene] dichloropalladium(II)
PE petroleum ether
PS polystyrene
RT or rt room temperature
sat. saturated
t-BuOH tent-butanol
t-Bu tent-butyl
TEA triethyl amine
TFA trifluoroacetic acid
THF tetrahydrofuran
TLC thin layer chromatography
TMSOK Potassium trimethylsilanolate
uL microliter(s)
XPhos Pd G2 Chloro(2-dicyclohexylphosphino-2',4',6'-triisopropyl-1,1'-biphenyl)[2-(2'-amino-1,1'-biphenyl)] palladium(II)
XantPhos Pd G3[(4,5-Bis(diphenylphosphino)-9,9-dimethylxanthene)-2-(2'-amino-1,1'-biphenyl)]palladium (II) methanesulfonate The following examples are intended to be illustrative only and not limiting in any way.

Abbreviations used are those conventional in the art or the following.

General Synthetic Schemes

The compounds of formula (I) may be prepared by methods known in the art of organic synthesis as set forth in part by the following synthetic schemes and synthetic procedures and conditions for the illustrative intermediates and examples.

The compounds described herein may be made from commercially available starting materials or synthesized using known organic, inorganic, and/or enzymatic processes.

While the present invention has been described in conjunction with the specific examples set forth below, many alternatives, modifications, and variations thereof will be apparent to those of ordinary skill in the art. All such alternatives, modifications, and variations are intended to fall within the spirit and scope of the present invention.

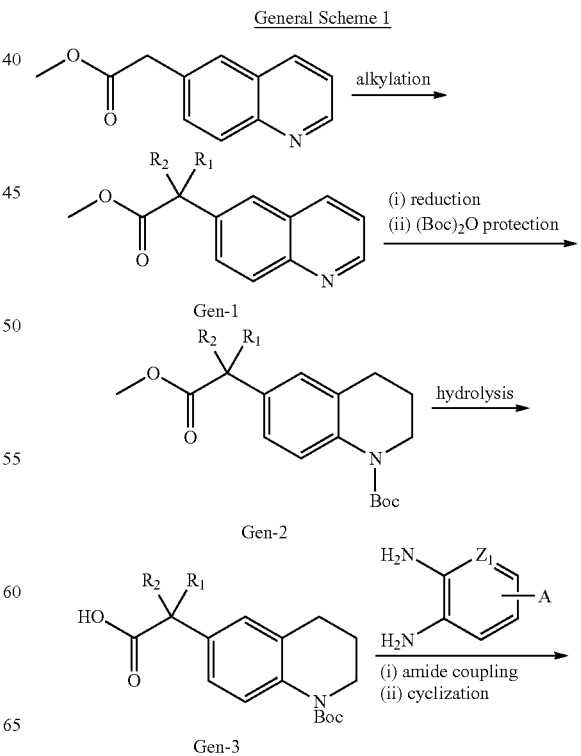

General Scheme 1

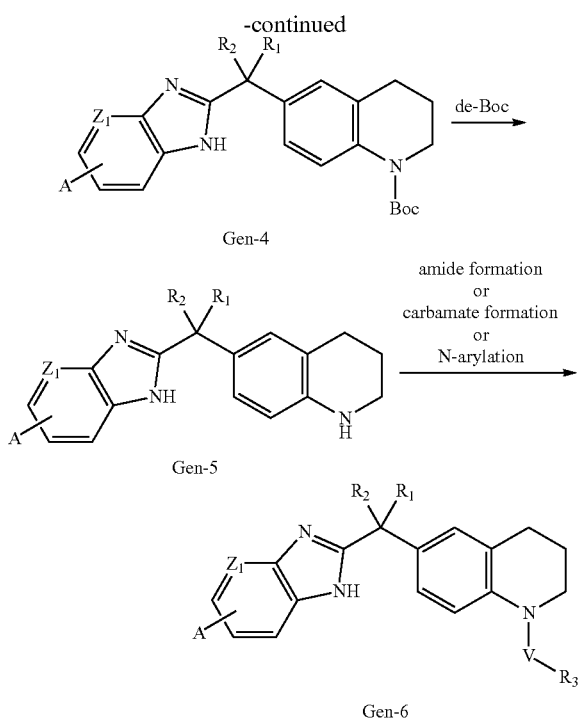

Gen-4

Gen-5

Gen-6

In General Scheme 1, Gen-1 was prepared through alkylation of commercially available methyl 2-(quinolin-6-yl) acetate, following partial reduction, then Boc protection to generate Gen-2. Gen-2 was converted to Gen-3 through ester hydrolysis. Gen-3 was elaborated to Gen-4 by amide coupling with diverse phenyl or hererocyclic diamines, followed by dehydrative cyclization. Gen-4 was de-Boc to generate Gen-5. Then Gen-5 went through amide coupling reaction or carbamate formation reaction, or N-arylation to generate Gen-6. The representative compounds are described in more detail below.

In General Scheme 2, Gen-8 was prepared through palladium catalyzed coupling reaction of synthetically prepared intermediate (I-D) with diverse acetonitrile derivatives, followed by hydrolysis. Gen-8 can also be prepared through alkylation of synthetically prepared intermediate (I-H), followed by hydrolysis. Then Gen-8 was elaborated to Gen-9 by amide coupling with diverse phenyl or heterocyclic diamines, followed by dehydrative cyclization. Gen-9 was de-Boc to generate Gen-10. Then Gen-10 went through amide coupling reaction or carbamate formation reaction, or N-arylation to generate Gen-11. The representative compounds are described in more detail below.

EXAMPLES

The following experimental procedures detail the preparation of specific examples of the instant disclosure. The examples are for illustrative purposes only and are not intended to limit the scope of the instant disclosure in any way.

The compounds described herein may be made from commercially available starting materials or synthesized using known organic, inorganic, and/or enzymatic processes.

While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention. Starting materials and intermediates are purchased from commercial sources, made from known procedures, or are otherwise illustrated.

Unless otherwise indicated, all variables are as previously defined.

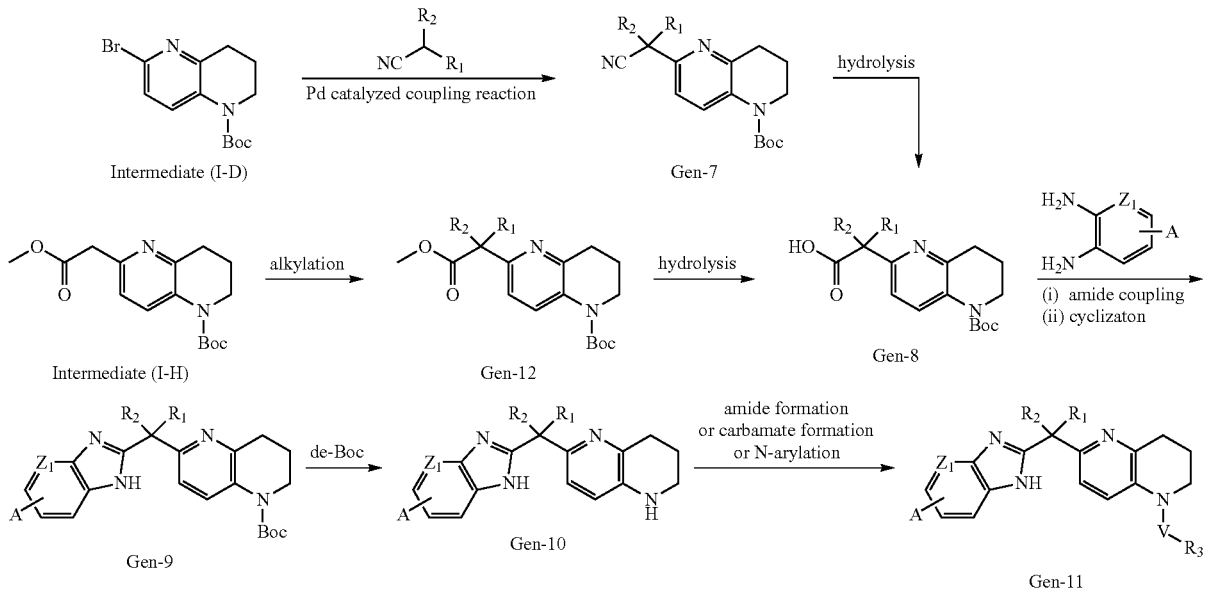

General Scheme 2

Examples

Example 1: Cyclopropyl(6-(1-(6-(trifluoromethyl)-1H-imidazo[4,5-b]pyridin-2-yl)cyclobutyl)-3A-dihydroquinolin-1(2H)-yl)methanone (Ex. 1)

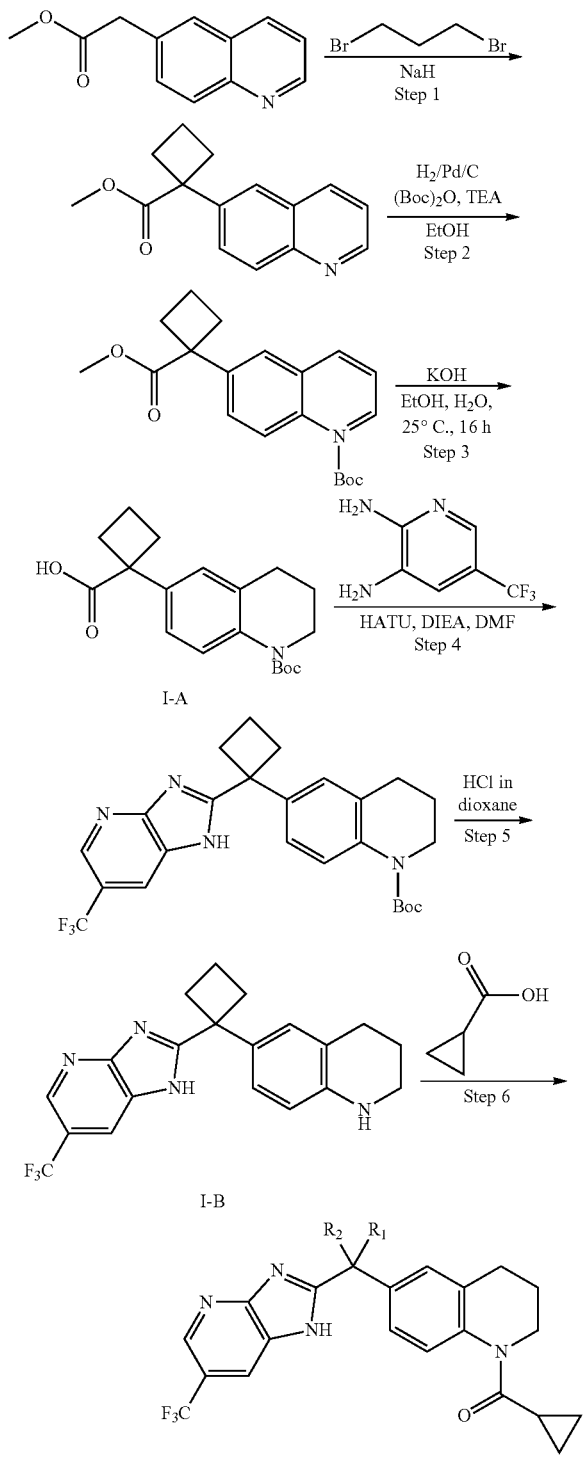

Step 1: Synthesis of methyl 1-(quinolin-6-yl)cyclobutane-1-carboxylate:

To a 2 L round bottom flask, were added methyl 2-(quinolin-6-yl)acetate (56 g, 278 mmol, 1.0 eq) and 1,3-dibromopropane (56.2 g, 278 mmol, 28.4 mL, 1.0 eq) in DMF (1.1 L) at 5° C. Then NaH (24.5 g, 612 mmol, 60% purity, 2.2 eq) was added in portions at 5° C. The reaction suspension was stirred at 18° C. for 2 h. The reaction mixture was poured into saturated NH4Cl (1 L). The mixture was extracted with EtOAc (3×1L). The combined organic layers were washed with brine (1 L) and dried with anhydrous Na$_2$SO$_4$. After filtration, the solvent was removed in vacuo, and the crude product was purified by column chromatography on silica gel eluting with DCM to afford methyl 1-(quinolin-6-yl)cyclobutane-1-carboxylate. MS (D) m/z 242[M+H]$^+$.

Step 2: Synthesis of tert-butyl 6-(1-(methoxycarbonyl)cyclobutyl)-3,4-dihydroquinoline-1(2H)-carboxylate:

To a dry hydrogenation flask (1 L) was added Pd/C (11 g, 10% Pd on carbon), EtOH (45 mL). Then methyl 1-(quinolin-6-yl)cyclobutane-1-carboxylate (36 g, 149 mmol, 1 eq) and Boc$_2$O (39.1 g, 179 mmol, 41.1 mL, 1.2 eq) was added in the reaction suspension. The suspension was degassed under vacuum and purged with H$_2$ three times. The reaction suspension was stirred at 50° C. under H$_2$ (30 Psi) for 12 h. Additional Boc$_2$O (9.77 g, 44.8 mmol, 10.3 mL, 0.3 eq) and TEA (7.55 g, 74.6 mmol, 10.4 mL, 0.5 eq) was added in the reaction suspension at 50° C. and the reaction mixture was stirred for additional 2.5 h. The reaction was monitored by TLC (Petroleum ether: Ethyl acetate=8:1) and it showed the starting material was consumed completely. The reaction mixture was filtered through a pad of celite. The filtrate was concentrated in vacuo and purified by column chromatography on silica gel (EtOAc in petroleum ether: 0-5% gradient) to give tert-butyl 6-(1-(methoxycarbonyl)cyclobutyl)-3,4-dihydroquinoline-1(2H)-carboxylate. MS (EI) m/z 346 [M+H]$^+$.

Step 3: Synthesis of 1-(1-(tert-butoxycarbonyl)-1,2,3,4-tetrahydroquinolin-6-yl)cyclobutane-1-carboxylic acid (I-A)

To a stirred solution of tert-butyl 6-(1-(methoxycarbonyl)cyclobutyl)-3,4-dihydroquinoline-1(2H)-carboxylate (655 mg, 1.915 mmol) in EtOH (10 mL) and Water (5 mL) was added KOH (376 mg, 6.70 mmol) at 15° C. After the addition was finished, the reaction mixture was stirred at 25° C. for 16 h. The reaction was neutralized by the addition of aq. HCl (1 N) until pH~6, extracted by EtOAc(30 mL×3). The organic layers were combined, washed with brine, and dried over Na$_2$SO$_4$. After filtration, the filtrate was concentrated in vacuo. The residue was purified by column chromatography on silica gel (MeOH in DCM, 5-10% gradient) to afford 1-(1-(tert-butoxycarbonyl)-1,2,3,4-tetrahydroquinolin-6-yl)cyclobutane-1-carboxylic acid (I-A). MS (EI) m/z 354 [M+Na]$^+$.

Step 4: Preparation of tert-butyl 6-(1-(6-(trifluoromethyl)-1H-imidazo[4,5-b]pyridin-2-yl)cyclobutyl)-3,4-dihydroquinoline-1(2H)-carboxylate To a vial were added I-A (100 mg, 0.302 mmol), 5-(trifluoromethyl)pyridine-2,3-diamine (64.1 mg, 0.362 mmol), HATU (252 mg, 0.664 mmol), DMF (1000 μl) and DIEA (200 μl, 1.145 mmol). The mixture was heated at 100° C. for 18 h. Concentrated the solvent in vacuo to afford residue, which was purified by column chromatograpy on silica (10 g, EtOAc in hexane, 0-70% gradient) to afford tert-butyl 6-(1-(6-(trifluoromethyl)-1H-imidazo[4,5-b]pyridin-2-yl) cyclobutyl)-3,4-dihydroquinoline-1(2H)-carboxylate. MS (EI) m/z 473 [M+H]+.

Step 5: Preparation of 6-(1-(6-(trifluoromethyl)-1H-imidazo[4,5-b]pyridin-2-yl)cyclobutyl)-1,2,3,4-tetrahydroquinoline (I-B)

To a vial containing tert-butyl 6-(1-(6-(trifluoromethyl)-1H-imidazo[4,5-b]pyridin-2-yl)cyclobutyl)-3,4-dihydroquinoline-1(2H)-carboxylate (32 mg, 0.068 mmol) were added Dioxane (500 μl) and HCl in dioxane (4M, 500 μl, 2.000 mmol). The mixture was stirred at rt for 20 h. Concentrated the solvent in vacuo to afford 6-(1-(6-(trifluoromethyl)-1H-imidazo[4,5-b]pyridin-2-yl)cyclobutyl)-1,2,3,4-tetrahydroquinoline as HCl salt (I-B). MS (EI) m/z 373 [M+H]+.

Step 6: Preparation of cyclopropyl(6-(1-(6-(trifluoromethyl)-1H-imidazo[4,5-b]pyridin-2-yl)cyclobutyl)-3,4-dihydroquinolin-1(2H)-yl)methanone (Ex.1)

To a flask were added I-B (27 mg, 0.066 mmol), HATU (37.7 mg, 0.099 mmol), DMF (600 μl), cyclopropanecarboxylic acid (17 mg, 0.197 mmol) and DIEA (150 μl, 0.859 mmol). The mixture was stirred at rt for 19 h. The mixture was filtered and purified by reversed phase HPLC (ACN/water with 0.1% TFA) to afford the title compound as TFA salt (Ex.1) $^1$H NMR (600 MHz, DMSO-d6) δ8.60 (s, 1H), 8.27 (s, 1H), 7.32 (d, J=8.0 Hz, 1H), 7.21 (s, 1H), 7.14 (d, J=7.9 Hz, 1H), 3.70-3.58 (m, 2H), 3.04-2.96 (m, 2H), 2.77-2.59 (m, 4H), 2.05-1.60 (m, 5H), 0.88-0.78 (m, 2H), 0.77-0.62 (m, 2H); MS (EI) m/z 441 [M+H]+.

Example 2, 3 and 4 were made by using the same procedure as Example 1.

| Ex. No. | Structure | IUPAC Name | Exact Mass [M + H]+ |
|---|---|---|---|
| 2 | 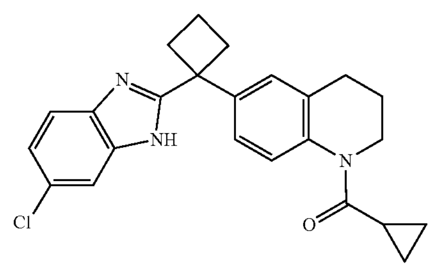 [SMILES: O=C(C1CC1)N1CCCc2cc(C3(c4nc5ccc(Cl)cc5[nH]4)CCC3)ccc21] | {6-[1-(6-chloro-1H-benzimidazol-2-yl)cyclobutyl]-3,4-dihydroquinolin-1(2H)-yl}(cyclopropyl)methanone | Calc'd 406, found 406 |
| 3 | 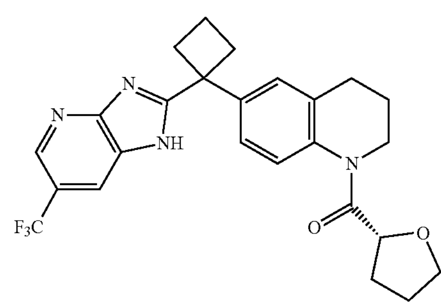 [SMILES: O=C([C@H]1CCCO1)N1CCCc2cc(C3(c4nc5ncc(C(F)(F)F)cc5[nH]4)CCC3)ccc21] | [(2R)-oxolan-2-yl][6-{1-[6-(trifluoromethyl)-1H-imidazo[4,5-b]pyridin-2-yl]cyclobutyl}-3,4-dihydroquinolin-1(2H)-yl]methanone | Calc'd 471, found 471 |
| 4 | 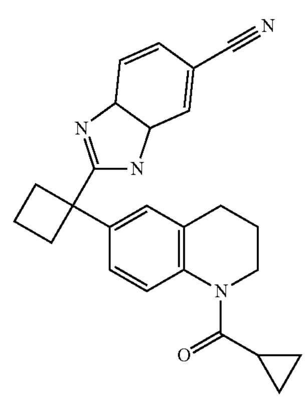 [SMILES: N#CC1=CC2NC(C3(c4ccc5c(c4)CCCN5C(=O)C4CC4)CCC3)=NC2C=C1] | 2-{1-[1-(cyclopropanecarbonyl)-1,2,3,4-tetrahydroquinolin-6-yl]cyclobutyl}-1H-benzimidazole-6-carbonitrile | Calc'd 397, found 397 |

Example 5: Methyl 6-(1-(6-(trifluoromethyl)-1H-imidazo[4,5-b]pyridin-2-yl)cyclobutyl)-3,4-dihydroquinoline-1(2H)-carboxylate (Ex. 5)

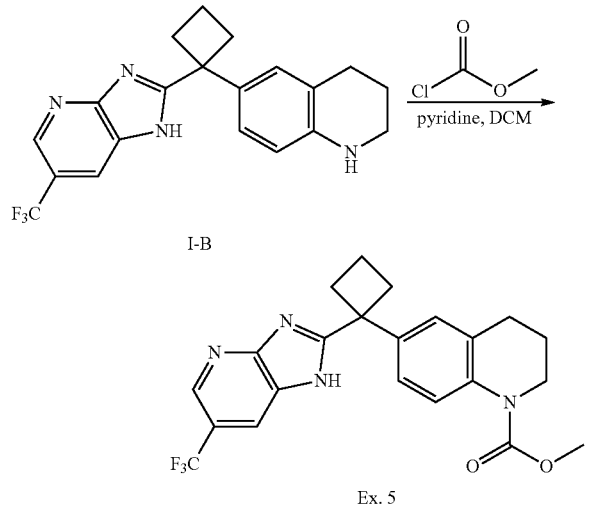

To a solution of I-B (28.3 mg, 0.069 mmol), pyridine (100 µl, 1.236 mmol) in DCM (700 µl), was added methyl chloroformate (34 mg, 0.360 mmol) at 0° C. dropwise and slowly warm to RT. The mixture was stirred at RT for 20 h. The solvent was removed in vacuo. The residue was dissolved into MeOH, filtered and purified by reversed phase HPLC (ACN/water with 0.1% TFA) to afford the title compound as TFA salt (Ex.5) $^1$H NMR (600 MHz, DMSO-d6) δ8.60 (s, 1H), 8.25 (s, 1H), 7.52 (d, J=7.6 Hz, 1H), 7.16-7.02 (m, 2H), 3.63 (s, 3H), 3.63-3.48 (m, 2H), 3.05-2.92 (m, 2H), 2.74-2.59 (m, 4H), 2.00-1.85 (m, 2H), 1.84-1.69 (m, 2H); MS (EI) m/z 431[M+H]$^+$.

Example 6: Cyclopropyl 6-(1-(6-chloro-1H-imidazo[4,5-b]pyridin-2-yl)ethyl)-3,4-dihydroquinoline-1(2H)-carboxylate (Ex. 6)

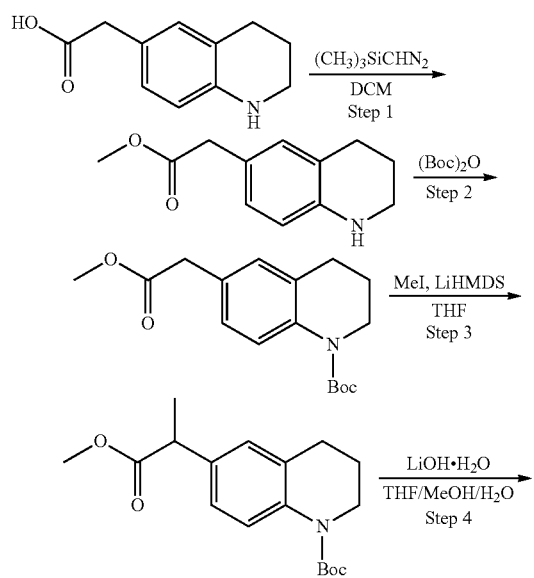

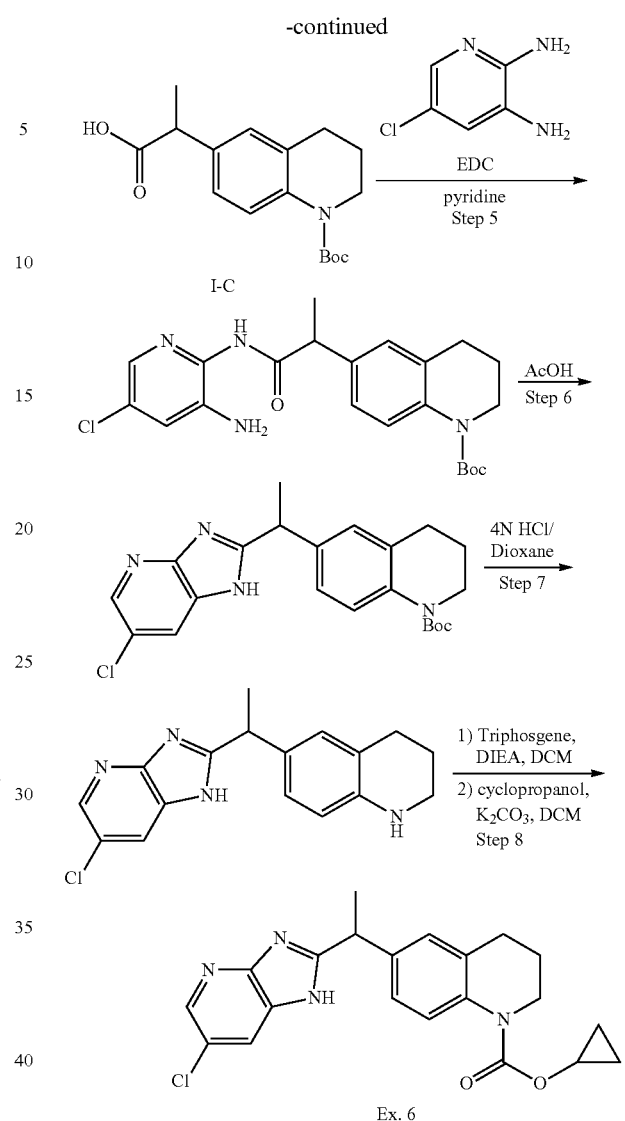

Step 1: Methyl 2-(1,2,3,4-tetrahydroquinolin-6-yl)acetate

To a suspension of 2-(1,2,3,4-tetrahydroquinolin-6-yl) acetic acid (1 g, 5.23 mmol) in DCM (5 ml) at 0° C. was added (trimethylsilyl)diazomethane in hexane solution (2 M, 7.84 ml, 15.69 mmol) dropwise. After the completion of addition, the mixture was concentrated and purified by column chromatography on silica gel (EtOAc: EtOH(3:1) in hexane, 0-80% gradient) to afford methyl 2-(1,2,3,4-tetrahydroquinolin-6-yl)acetate. MS (EI) m/z 206 [M+H]$^+$.

Step 2: tert-butyl 6-(2-methoxy-2-oxoethyl)-3,4-dihydroquinoline-1(2H)-carboxylate.

To a solution of methyl 2-(1,2,3,4-tetrahydroquinolin-6-yl)acetate (2000 mg, 9.74 mmol) in acetonitrile (10 ml) was added Boc anhydride (2.71 ml, 11.69 mmol) at RT. The reaction was monitored by TLC and the starting material was found to converted to product after 24 h. The solvent was removed in vacuo and the residue was purified by column chromatography on silica gel (EtOAc: EtOH(3:1) in hexane, 0-80% gradient) to afford tert-butyl 6-(2-methoxy-2-oxoethyl)-3,4-dihydroquinoline-1(2H)-carboxylate. MS (EI) m/z 306 [M+H]⁺.

Step 3: tert-butyl 6-(1-methoxy-1-oxopropan-2-yl)-3,4-dihydroquinoline-1(2H)-carboxylate.

To a solution of tent-butyl 6-(2-methoxy-2-oxoethyl)-3,4-dihydroquinoline-1(2H)-carboxylate (1000 mg, 3.27 mmol) in THF (20 ml) at −78° C. was added LiHMDS solution in hexane (1 M, 3930 µl, 3.93 mmol)) under nitrogen. The reaction mixture was stirred at −78° C. for 2 h. Then iodomethane (410 µl, 6.55 mmol) was added and the reaction mixture was brought to rt. After stirring for 1 h, the reaction was quenched with NH₄Cl (sat.), diluted with EtOAc and brine. The organic layer was separated, dried over Na₂SO₄ and filtered. The filtrate was concentrated in vacuo and purified by column chromatography on silica gel (EtOAc in hexane: 0-30% gradient) to afford tent-butyl 6-(1-methoxy-1-oxopropan-2-yl)-3,4-dihydroquinoline-1(2H)-carboxylate. MS (EI) m/z 320 [M+H]⁺.

Step 4: 2-(1-(tert-butoxycarbonyl)-1,2,3,4-tetrahydroquinolin-6-yl)propanoic acid (I-C)

To a stirred solution of tert-butyl 6-(1-methoxy-1-oxopropan-2-yl)-3,4-dihydroquinoline-1(2H)-carboxylate (1.0 g, 3.13 mmol) in THF (8 mL), water (4 mL) and MeOH (8 mL) was added lithium hydroxide hydrate (0.394 g, 9.39 mmol) at rt. The resulting reaction mixture was stirred at the rt for 2 h. HCl solution (6N) was added to adjust pH~7. Then the reaction mixture was extracted with EtOAc (30 mL×3). The organic layers were combined, washed with brine, dried over Na₂SO₄ and filtered. The filtrate was concentrated in vacuo to give the crude 2-(1-(tert-butoxycarbonyl)-1,2,3,4-tetrahydroquinolin-6-yl)propanoic acid (I-C). MS (EI) m/z 306 [M+H]⁺.

Step 5: tert-butyl 6-(1-((3-amino-5-chloropyridin-2-yl)amino)-1-oxopropan-2-yl)-3,4-dihydroquinoline-1(2H)-carboxylate To a stirred solution of I-C (900 mg, 2.95 mmol) in pyridine (20 mL) was added EDC (1.7 g, 8.87 mmol) and 5-chloropyridine-2,3-diamine (635 mg, 4.42 mmol) at rt. The reaction mixture was stirred at rt for 16 h. The solvent was removed in vacuo. The reaction was diluted with water (50 mL) and extracted with EtOAc (30 mL×2), the organic layers were combined, washed with brine, dried over Na₂SO₄ and filtered. The filtrate was concentrated in vacuo. The residue was purified by column chromatography on silica gel (EtOAc in petroleum ether, 10-40% gradient) to afford tert-butyl 6-(1-((3-amino-5-chloropyridin-2-yl)amino)-1-oxopropan-2-yl)-3,4-dihydroquinoline-1(2H)-carboxylate. MS (EI) m/z 431 [M+H]⁺.

Step 6: tert-butyl 6-(1-(6-chloro-1H-imidazo[4,5-b]pyridin-2-yl)ethyl)-3,4-dihydroquinoline-1(2H)-carboxylate tert-butyl 6-(1-((3-amino-5-chloropyridin-2-yl)amino)-1-oxopropan-2-yl)-3,4-dihydroquinoline-1(2H)-carboxylate (500 mg, 1.16 mmol) was dissolved in AcOH (25 mL) at rt. Then the mixture was heated at 120° C. for 4 h. The solvent was removed in vacuo to afford crude tert-butyl 6-(1-(6-chloro-1H-imidazo[4,5-1)]pyridin-2-yl)ethyl)-3,4-dihydroquinoline-1(2H)-carboxylate, which was used in next step directly without further purification. MS (EI) m/z 413 [M+H]⁺.

Step 7: 6-(1-(6-chloro-1H-imidazo[4,5]pyridin-2-yl)ethyl)-1,2,3,4-tetrahydroquinoline To a stirred solution of tert-butyl 6-(1-(6-chloro-1H-imidazo[4,5-b]pyridin-2-yl)ethyl)-3,4-dihydroquinoline-1(2H)-carboxylate (400 mg, 0.97 mmol) in dioxane (1 mL) was added HCl in hexane (4M, 5 mL, 2.00 mmol). The mixture was stirred at rt for 2 h. The solvent was evaporated in vacuo. The residue was diluted with NaHCO₃ (sat.) to adjust pH~7, then extracted with EtOAc (10 mL×2). The organic layers were combined, washed with brine, dried over Na₂SO₄, and filtered. The filtrate was concentrated in vacuo. The residue was purified by column chromatography on silica gel (EtOAc in petroleum ether: 0-50% gradient) to afford 6-(1-(6-chloro-1H-imidazo[4,5-b]pyridin-2-yl)ethyl)-1,2,3,4-tetrahydroquinoline. MS (EI) m/z 313 [M+H]⁺.

Step 8: cyclopropyl 6-(1-(6-chloro-1H-imidazo[4,5-b]pyridin-2-yl)ethyl)-3,4-dihydroquin oline-1(2H)-carboxylate (Ex. 6)

To a stirred solution of 6-(1-(6-chloro-1H-imidazo[4,5-b]pyridin-2-yl)ethyl)-1,2,3,4-tetrahydroquinoline (80 mg, 0.256 mmol) in DCM (3 mL) were added DIEA (0.1 mL, 0.573 mmol) and bis(trichloromethyl) carbonate (91 mg, 0.307 mmol) at 0° C. The mixture was stirred at 0° C. for 2 h, K₂CO₃ (99 mg, 0.720 mmol) and cyclopropanol (139 mg, 2.398 mmol) were added. Then the mixture was stirred at 60° C. for 3 h. The reaction was quenched with water and extracted with DCM. The organic layers were combined, washed with brine, dried over Na₂SO₄. After filtration, the filtrate was concentrated in vacuo. The residue was purified by prep-TLC (petroleum ether: EtOAc=1:1) to afford the title compound (Ex.6). ¹H NMR (400 MHz,CD3OD) δ8.39 (d, J=2.2 Hz, 1 H), 8.01 (d, J=2.2 Hz, 1 H), 7.60 (br d, J=7.7 Hz, 1 H), 7.10-7.16 (m, 2 H), 4.47 (q, J=7.2 Hz, 1 H), 4.08-4.15 (m, 1 H), 3.65-3.70 (m, 2 H), 2.75 (t, J=6.5 Hz, 2 H), 1.89 (quin, J=6.3 Hz, 2 H), 1.80 (d, J=7.3 Hz, 3 H), 0.68-0.76 (m, 4 H); MS (EI) m/z 397.0 [M+H]⁺.

Example 7 and Example 8: cyclopropyl (S)-6-(1-(6-cyano-1H-imidazo[4,5-b]pyridin-2-yl)ethyl)-3,4-dihydroquinoline-1(2H)-carboxylate and cyclopropyl (R)-6-(1-(6-cyano-1H-imidazo[4,5-b]pyridin-2-yl)ethyl)-3,4-dihydroquinoline-1(2H)-carboxylate (Ex.7 and Ex. 8)

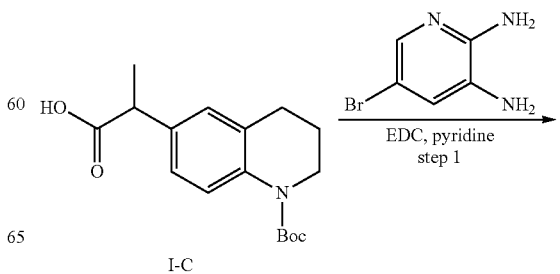

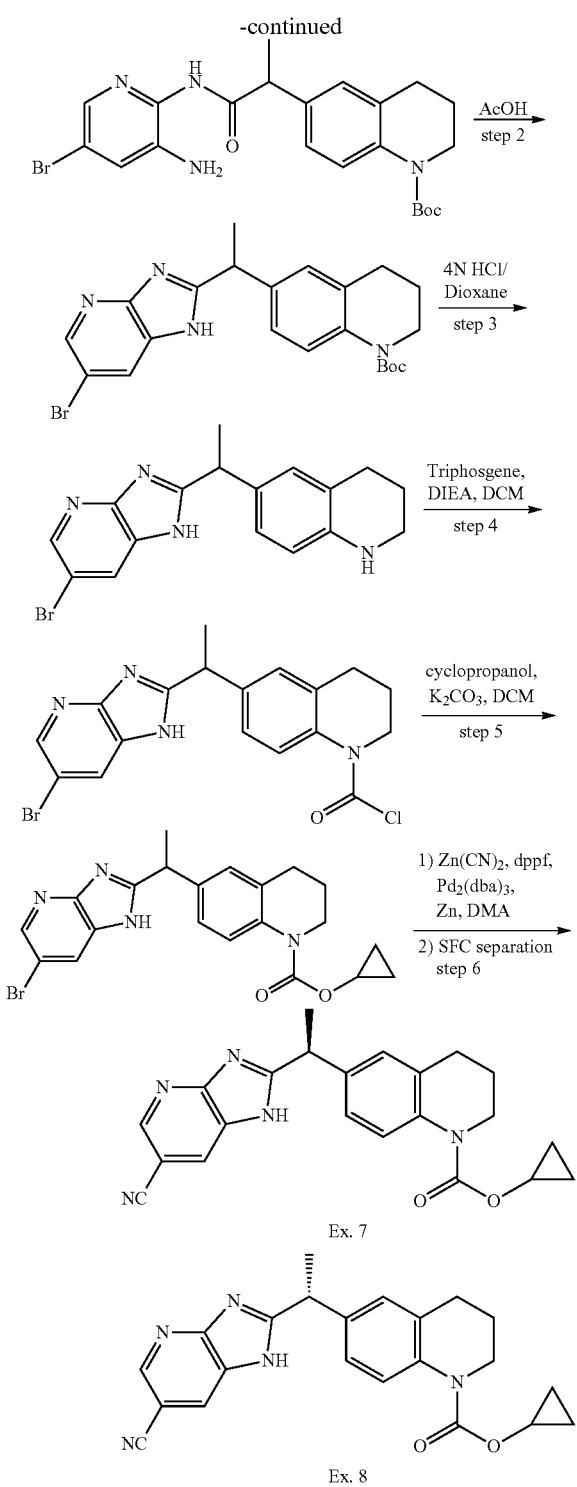

extracted with EtOAc twice. The organic layers were combined, washed with brine, dried over Na₂SO₄ and filtered. The filtrate was concentrated in vacuo to afford residue, which was purified by column chromatography on silica gel (EtOAc in petroleum ether: 10-40% gradient) to afford tert-butyl 6-(1-((3-amino-5-bromopyridin-2-yl)amino)-1-oxopropan-2-yl)-3,4-dihydroquinoline-1(2H)-carboxylate. MS (EI) m/z 475 [M+H]⁺.

Step 2: tert-butyl 6-(1-(6-bromo-1H-imidazo[4,5-b]pyridin-2-yl)ethyl)-3,4-dihydroquinoline-1(2H)-carboxylate tert-butyl 6-(1-((3-amino-5-bromopyridin-2-yl)amino)-1-oxopropan-2-yl)-3,4-dihydroquinoline-1(2H)-carboxylate (1.3 g, 2.73 mmol) was dissolved in AcOH (20 mL) at rt. Then the mixture was heated at 120° C. for 16 h. The solvent was removed in vacuo to afford the crude product tert-butyl 6-(1-(6-bromo-1H-imidazo[4,5-b]pyridin-2-yl)ethyl)-3,4-dihydroquinoline-1(2H)-carboxylate. MS (EI) m/z 401 [M−56+H]⁺.

Step 3: 6-(1-(6-bromo-1H-imidazo[4, 5-b]pyridin-2-yl)ethyl)-1,2,3,4-tetrahydroquinoline To a stirred solution of tert-butyl 6-(1-(6-bromo-1H-imidazo[4,5-b]pyridin-2-yl)ethyl)-3,4-dihydroquinoline-1 (2H)-carboxylate (1.0 g, 2.186 mmol) in MeOH (3 mL) was added HCl solution (4M in dioxane, 10 mL, 40.0 mmol) at rt. The mixture was stirred at rt for 16 h, then concentrated in vacuo. The residue was diluted with EtOAc and NaHCO₃ (aq.) and stirred for 0.5 h. Then the mixture was transferred to separatory funnel. The aqueous layer was extracted with EtOAc three times. The organic layers were combined, washed with brine, dried over Na₂SO₄. After filtration, the filtrate was concentrated in vacuo to afford residue, which was purified by column chromatography on silica gel (EtOAc in petroleum ether: 0-80% gradient) to afford 6-(1-(6-bromo-1H-imidazo[4,5-b]pyridin-2-yl)ethyl)-1,2,3,4-tetrahydroquinoline. MS (EI) m/z 357 [M+H]⁺.

Step 4: 6-(1-(6-bromo-1H-imidazo[4,5-b]pyridin-2-yl)ethyl)-3,4-dihydroquinoline-1(2H)-carbonyl chloride To a stirred solution of 6-(1-(6-bromo-1H-imidazo[4,5-b]pyridin-2-yl)ethyl)-1,2,3,4-tetrahydroquinoline (190 mg, 0.532 mmol) in DCM (3 mL) was added DIEA (0.2 mL, 1.435 mmol) and triphosgene (150 mg, 0.505 mmol) at rt. The reaction was stirred at rt for 1 h. The reaction mixture was quenched with NaHCO₃(aq.) and extracted with DCM three times. The organic layers were combined, washed with brine, dried over Na₂SO₄. After filtration, the filtrate was concentrated in vacuo to give the crude product 6-(1-(6-bromo-1H-imidazo[4,5-b]pyridin-2-yl)ethyl)-3,4-dihydroquinoline-1(2H)-carbonyl chloride, which was used in the next step without further purification. MS (EI) m/z 419 [M+H]⁺.

Step 5: cyclopropyl 6-(1-(6-bromo-1H-imidazo[4,5-b]pyridin-2-yl)ethyl)-3,4-dihydroquinoline-1(2H)-carboxylate To a stirred solution of 6-(1-(6-bromo-1H-imidazo[4,5-b]pyridin-2-yl)ethyl)-3,4-dihydroquinoline-1(2H)-carbonyl chloride (200 mg, 0.477 mmol) in DCM (3 mL) was added K₂CO₃ (198 mg, 1.430 mmol) and cyclopropanol (277 mg, Step 1: tert-butyl 6-(1-((3-amino-5-bromopyridin-2-yl)amino)-1-oxopropan-2-yl)-3,4-dihydroquinoline-1(2H)-carboxylate To a stirred solution of I-C (900 mg, 2.95 mmol) in pyridine (20 mL) were added EDC (1.7 g, 8.87 mmol) and 5-bromopyridine-2,3-diamine (831 mg, 4.42 mmol) at rt. The mixture was stirred at rt for 16 h. The solvent was removed in vacuo. The residue was diluted with water and 4.77 mmol) at rt. The mixture was stirred at 60° C. for 16 h. The reaction mixture was diluted with water and extracted with DCM three times. The organic layers were combined, washed with brine, dried over $Na_2SO_4$. After filtration, the filtrate was concentrated in vacuo to afford residue, which was purified by prep-TLC (petroleum ether:EtOAc=1:1) to afford cyclopropyl 6-(1-(6-bromo-1H-imidazo[4,5-b]pyridin-2-yl)ethyl)-3,4-dihydroquinoline-1(2H)-carboxylate. MS (EI) m/z 441 $[M+H]^+$.

Step 6: cyclopropyl (S)-6-(1-(6-cyano-1H-imidazo[4,5-b]pyridin-2-yl)ethyl)-3,4-dihydroquinoline-1(2H)-carboxylate and cyclopropyl (R)-6-(1-(6-cyano-1H-imidazo[4,5-b]pyridin-2-yl)ethyl)-3,4-dihydroquinoline-1(2H)-carboxylate (Ex.7 and Ex. 8)

To a solution of cyclopropyl 6-(1-(6-bromo-1H-imidazo[4,5-b]pyridin-2-yl)ethyl)-3,4-dihydroquinoline-1(2H)-carboxylate (100 mg, 0.227 mmol), dppf (13 mg, 0.023 mmol) and zinc (20 mg, 0.306 mmol) in DMA (2 mL) were added $Zn(CN)_2$ (50 mg, 0.426 mmol) and $Pd_2(dba)_3$ (12 mg, 0.013 mmol) at rt. The reaction mixture was irradiated in microwave at 150° C. for 1 h. The mixture was cooled to rt, filtered and purified by reversed phase HPLC eluting with water (0.1% TFA)-ACN to afford cyclopropyl 6(1-(6-cyano-1H-imidazo[4,5-b]pyridin-2-yl)ethyl)-3,4-dihydroquinoline-1(2H)-carboxylate. This product was sent to SFC chiral separation (Column: ChiralPak AD-3 150×4.6 mm I.D., 3 µm; Mobile phase A: $CO_2$; Mobile phase B: IPA with 0.05% DEA) to afford the title compounds Example 7 and Example 8.

Example 7, Retention Time: 2.236 min $^1$H NMR (400 MHz, $CD_3OD$) δ8.69 (d, J=1.75 Hz, 1 H), 8.33 (d, J=1.75 Hz, 1 H), 7.58 (br d, J=7.45 Hz, 1 H), 7.09-7.15 (m, 2 H), 4.49 (q, J=7.02 Hz, 1 H), 4.07-4.14 (m, 1 H), 3.62-3.71 (m, 2 H), 2.73 (t, J=6.58 Hz, 2 H), 1.84-1.94 (m, 2 H), 1.80 (d, J=7.45 Hz, 3 H), 0.68-0.74 (m, 4 H); MS (EI) m/z 388 $[M+H]^+$.

Example 8, Retention Time: 6.357 min $^1$H NMR (400 MHz, $CD_3OD$) δ8.70 (d, J=1.75 Hz, 1 H), 8.34 (d, J=1.75 Hz, 1 H), 7.59 (br d, J=7.89 Hz, 1 H), 7.09-7.16 (m, 2 H), 4.49 (q, J=7.45 Hz, 1 H), 4.05-4.15 (m, 1 H), 3.62-3.70 (m, 2 H), 2.74 (t, J=6.58 Hz, 2 H), 1.85-1.93 (m, 2 H), 1.81 (d, J=7.45 Hz, 3 H), 0.69-0.74 (m, 4 H); MS (ESI) m/z 388 $[M+H]^+$.

Example 9: (6-(1-(1H-benzo[d]imidazol-2-yl-3,4-dihydroquinolin-1(2H)-yl)(cyclopropyl)methanone (Ex. 9)

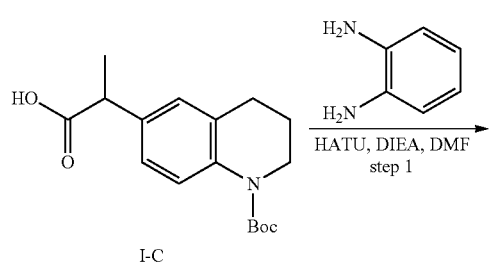

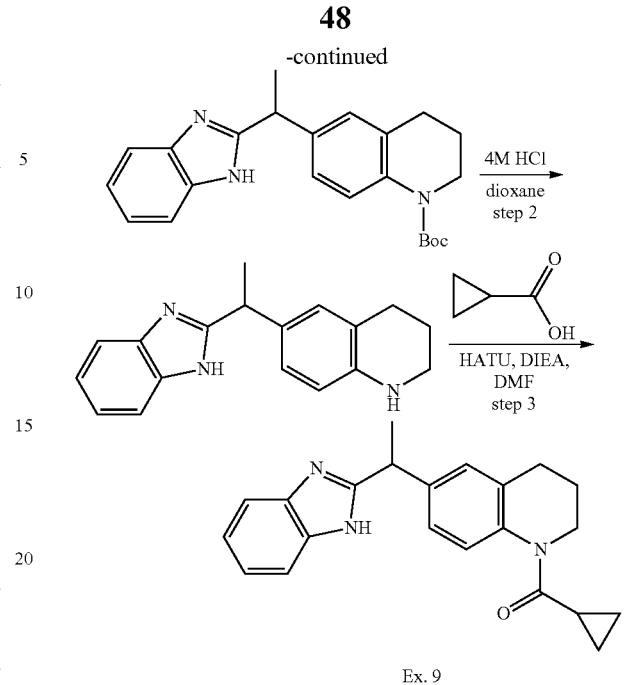

Ex. 9

Step 1: tert-butyl 6-(1-(1H-benzo[d]imidazol-2-yl)ethyl)-3,4-dihydroquinoline-1(2H)-carboxylate To a vial were added I-C (50 mg, 0.164 mmol), benzene-1,2-diamine (26.6 mg, 0.246 mmol), HATU (93 mg, 0.246 mmol), DMF (800 µl) and DIEA (100 µl, 0.573 mmol). The mixture was heated at 100° C. for 18 h. Evaporated the solvent in vacuo to afford residue, which was purified by column chromatography on silica gel (EtOAc in hexane, 0-70% gradient) to afford tert-butyl 6-(1-(1H-benzo[d]imidazol-2-yl)ethyl)-3,4-dihydroquinoline-1(2H)-carboxylate. MS (EI) m/z 378 $[M+H]^+$.

Step 2: 6-(1-(1H-benzo[d]imidazol-2-yl)ethyl)-1,2,3,4-tetrahydroquinoline

To a vial containing tert-butyl 6-(1-(1H-benzo[d]imidazol-2-yl)ethyl)-3,4-dihydroquinoline-1(2H)-carboxylate (48.7 mg, 0.129 mmol) was added dioxane (1 ml). To this solution was added HCl dioxane solution (4 M, 200 µl, 0.800 mmol). The mixture was stirred at rt for 18 h. Evaporated the solvent in vacuo to afford crude 6-(1-(1H-benzo[d]imidazol-2-yl)ethyl)-1,2,3,4-tetrahydroquinoline as HCl salt, which was used in next step directly. MS (EI) m/z 278 $[M+H]^+$.

Step 3: (6-(1-(1H-benzo[d]imidazol-2-yl)ethyl)-3,4-dihydroquinolin-1(2H)-yl)(cyclopropyl)methanone (Ex. 9)

To a vial were added 6-(1-(1H-benzo[d]imidazol-2-yl)ethyl)-1,2,3,4-tetrahydroquinoline HCl salt (40.5 mg, 0.129 mmol), HATU (73.6 mg, 0.194 mmol), DMF (1 ml), cyclopropanecarboxylic acid (26 mg, 0.302 mmol) and DIEA (100 0.573 mmol). The mixture was stirred at rt for 18 h, then filtered and purified by reversed phase HPLC, eluting with water (0.1% TFA)-ACN to afford the title compound as a TFA salt (Ex. 9).

$^1$H NMR (600 MHz, DMSO-d6) δ7.70 (dd, J=5.6, 2.9 Hz, 2H), 7.50-7.41 (m, 2H), 7.39 (d, J=8.0 Hz, 1H), 7.23 (s, 1H), 7.16 (d, J=8.0 Hz, 1H), 4.65 (q, J=6.7 Hz, 1H), 3.75-3.56 (m,

2H), 2.72-2.61 (m, 2H), 1.81 (p, J=6.3 Hz, 2H), 1.76 (d, J=7.1 Hz, 3H), 1.18-0.95 (m, 1H), 0.89-0.79 (m, 2H), 0.77-0.68 (m, 2H); MS (EI) m/z 346 [M+H]⁺.

Example 10: cyclopropyl 6-(1-(6-cyano-1H-imidazo[4,5-b]pyridin-2-yl)cyclobutyl)-3,4-dihydroquinoline-1(2H)-carboxylate (Ex. 10)

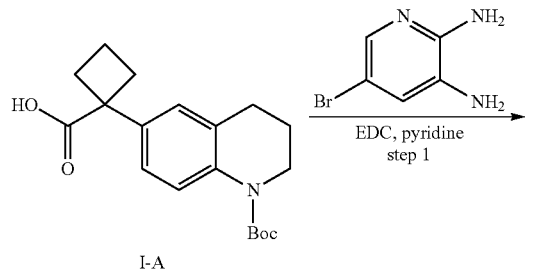

Ex. 10

Step 1: tert-butyl 6-1-((3-amino-5-bromopyridin-2-yl)carbamoyl)cyclobutyl)-3,4-dihydroquinoline-1(2H)-carboxylate To a stirred solution of I-A (480 mg, 1.448 mmol) in pyridine (10 mL) were added EDC (833 mg, 4.35 mmol) and 5-bromopyridine-2,3-diamine (327 mg, 1.738 mmol) at rt. The mixture was stirred at 30° C. for 3 h. The solvent was evaporated in vacuo. The residue was diluted with water and extracted with EtOAc twice. The organic layers were combined, washed with brine, dried over Na₂SO₄. After filtration, the filtrate was concentrated in vacuo to afford residue, which was purified by prep-TLC (SiO₂, petroleum ether: EtOAc=2:1) to afford tert-butyl 6-(1-((3-amino-5-bromopyridin-2-yl)carbamoyl)cyclobutyl)-3,4-dihydroquinoline-1(2H)-carboxylate. MS (EI) m/z 501 [M+H]⁺.

Step 2: tert-butyl 6-(1-(6-bromo-1H-imidazo[4,5-b]pyridin-2-yl)cyclobutyl)-3,4-dihydroquinoline-1(2H)-carboxylate To a stirred solution of tert-butyl 6-(1-((3-amino-5-bromopyridin-2-yl)carbamoyl)cyclobutyl)-3,4-dihydroquinoline-1(2H)-carboxylate (500 mg, 0.997 mmol) in DMF (20 mL) was added acetic acid (5 mL, 87 mmol) ar rt. The reaction mixture was stirred at 130° C. for 16 h. The solvent was evaporated in vacuo. The residue was diluted with NaHCO₃ (sat.) and extracted with EtOAc. The combined organic layers were washed with brine, dried over Na₂SO₄. After filtration, the filtrate was concentrated in vacuo. The residue was purified by prep-TLC (SiO₂, petroleum ether: EtOAc=2:1) to give tert-butyl 6-(1-(6-bromo-1H-imidazo[4,5-b]pyridin-2-yl)cyclobutyl)-3,4-dihydroquinoline-1(2H)-carboxylate. MS (EI) m/z 483 [M+H]⁺.

Step 3: tert-butyl 6-(1-(6-cyano-1H-imidazo[4,5-b]pyridin-2-yl)cyclobutyl)-3,4-dihydroquinoline-1(2H)-carboxylate To a solution of tert-butyl 6-(1-(6-bromo-1H-imidazo[4,5-b]pyridin-2-yl)cyclobutyl)-3,4-dihydroquinoline-1(2H)-carboxylate (170 mg, 0.352 mmol), dppf (8 mg, 0.014 mmol) and zinc (5 mg, 0.076 mmol) in DMA (5 mL) were added Zn(CN)2 (83 mg, 0.703 mmol) and Pd₂(dba)₃ (4 mg, 4.37 μmol) at rt. The mixture was irradiated in microwave at 150° C. for 1 h. Then the reaction was diluted with water and extracted with EtOAc. The combined organic layers were washed with brine, dried over Na₂SO₄. After filtration, the filtrate was concentrated in vacuo to afford residue, which was purified by prep-TLC (SiO₂, petroleum ether: EtOAc=2:1) to give tert-butyl 6-(1-(6-cyano-1H-imidazo[4,5-b]pyridin-2-yl)cyclobutyl)-3,4-dihydroquinoline-1(2H)-carboxylate. MS (EI) m/z 452 [M+Na]⁺.

Step 4: 6-(1-(6-isocyano-1H-imidazo[4,5-b]pyridin-2-yl)cyclobutyl)-1,2,3,4-tetrahydroquinoline To a stirred solution of tert-butyl 6-(1-(6-cyano-1H-imidazo[4,5-b]pyridin-2-yl)cyclobutyl)-3,4-dihydroquinoline-1(2H)-carboxylate (170 mg, 0.396 mmol) in DCM (3 mL) was added TFA (1 mL, 13.46 mmol) at RT. The reaction mixture was stirred at 30° C. for 2 h. The solvent was evaporated in vacuo to afford crude 6-(1-(6-isocyano-1H-imidazo[4,5-b]pyridin-2-yl)cyclobutyl)-1,2,3,4-tetrahydroquinoline as TFA salt, which was used directly in next step without further purification. MS (EI) m/z 330 [M+H]$^+$.

Step 5: cyclopropyl 6-(1-(6-cyano-1H-imidazo[4,5-b]pyridin-2-yl)cyclobutyl)-3,4-dihydroquinoline-1(2H)-carboxylate (Ex. 10)

To a solution of 6-(1-(6-isocyano-1H-imidazo[4,5-b]pyridin-2-yl)cyclobutyl)-1,2,3,4-tetrahydroquinoline TFA salt (30 mg, 0.068 mmol) and DIEA (0.04 mL, 0.229 mmol) in DCM (2 mL) was added triphosgene (40 mg, 0.135 mmol) at 0° C. The mixture was stirred at 0° C. for 0.5 h, then quenched with NaHCO$_3$ (sat.). The reaction mixture was diluted with water and extracted with EtOAc. The combined organic layers were washed with brine, dried over Na$_2$SO$_4$. After filtration, the filtrate was concentrated in vacuo to afford residue. The reside was dissolved in DCM (2 mL), then K$_2$CO$_3$ (28 mg, 0.203 mmol) and cyclopropanol (118 mg, 2.030 mmol) were added. The mixture was stirred at 60° C. for 2 h, then cooled to rt, diluted with water and extracted with EtOAc. The combined organic layers were washed with brine, dried over Na$_2$SO$_4$. After filtration, the filtrate was concentrated in vacuo to afford residue, which was purified by reversed phase HPLC, eluting with water (0.1% TFA)-ACN to afford the title compound as a TFA salt (Ex. 10). $^1$H NMR (400 MHz, CD$_3$OD) δ8.6 (d, J=1.8 Hz, 1 H), 8.3 (d, J=1.8 Hz, 1 H), 7.6 (br d, J=9.2 Hz, 1 H), 7.2 (d, J=8.4 Hz, 1 H), 7.2 (s, 1 H), 4.2-4.1 (m, 1 H), 3.7-3.6 (m, 2 H), 3.1-3.0 (m, 2 H), 2.9-2.8 (m, 2 H), 2.8 (t, J=6.6 Hz, 2 H), 2.2-2.0 (m, 2 H), 1.9-1.8 (m, 2 H), 0.7-0.6 (m, 4 H); MS (EI) m/z 414 [M+H]$^+$.

Example 11: 1-(pyridin-2-yl)-6-(1-(6-(trifluoromethyl)-1H-imidazo[4,5-b]pyridin-2-yl)cyclobutyl)-1,2,3,4-tetrahydroquinoline (Ex. 11)

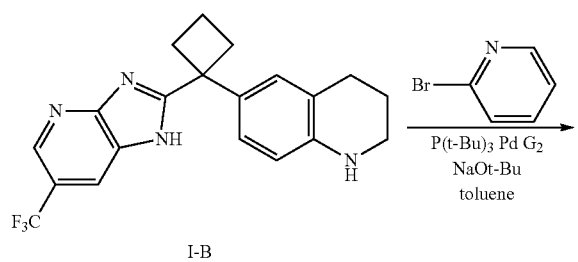

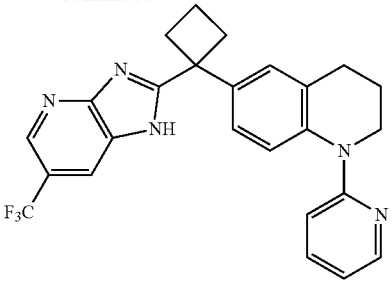
Ex. 11

A vial was charged with I-B (30 mg, 0.073 mmol), 2-bromopyridine (13.91 mg, 0.088 mmol), P(t-Bu)$_3$Pd G2 (2 mg, 3.90 µmol), NaOt-Bu (11.28 mg, 0.117 mmol) and toluene (700 µl). The mixture was evacuated and backfilled with N$_2$, then heated at 120° C. for 20 h. The mixture was filtered. The filtrate was concentrated, diluted with MeOH, filtered and purified by reversed phase HPLC (ACN/water with 0.1% TFA) to afford the title compound as a TFA salt (Ex. 11). $^1$H NMR (600 MHz, DMSO-d6) δ8.61 (s, 1H), 8.27 (s, 1H), 8.16 (d, J=4.0 Hz, 1H), 7.67 (s, 1H), 7.32-7.12 (m, 3H), 7.12-7.02 (m, 1H), 6.96-6.86 (m, 1H), 3.75 (t, J=5.7 Hz, 2H), 3.06-2.94 (m, 2H), 2.75-2.60 (m, 4H), 2.07-1.67 (m, 4H); MS (EI) m/z 450 [M+H]$^+$.

Example 12: 1-(pyrimidin-4-yl)-6-(1-(6-(trifluoromethyl)-1H-imidazo[4,5-b]pyridin-2-yl)cyclobutyl)-1,2,3,4-tetrahydroquinoline (Ex.12)

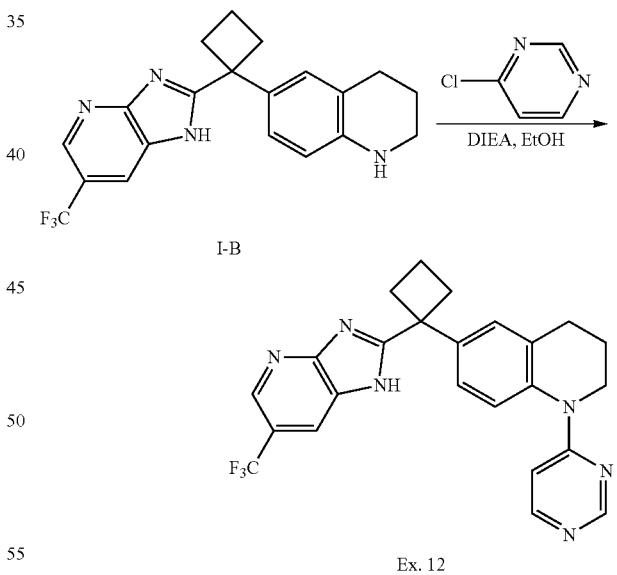

A vial was charged with I-B (30 mg, 0.073 mmol), 4-chloropyrimidine (20 mg, 0.175 mmol), EtOH (600 µl) and DIEA (100 µl, 0.573 mmol). The mixture was irradiated in microwave at 150° C. for 4 h, then filtered and purified by reversed phase HPLC (ACN/water with 0.1% TFA) to afford the title compound as a TFA salt (Ex. 12). $^1$H NMR (600 MHz, DMSO-d6) δ8.88 (s, 1H), 8.61 (s, 1H), 8.29 (broad s, 2H), 7.47 (d, J=8.3 Hz, 1H), 7.34 (s, 1H), 7.27-7.17 (m, 2H), 4.02-3.90 (m, 2H), 3.09-2.98 (m, 2H), 2.79-2.65 (m, 4H), 2.01-1.82 (m, 4H); MS (EI) m/z 451 [M+H]$^+$.

Intermediate I-E: 1-(5-(tert-butoxycarbonyl)-5,6,7,8-tetrahydro-1,5-naphthyridin-2-yl)cyclobutane-1-carboxylic acid

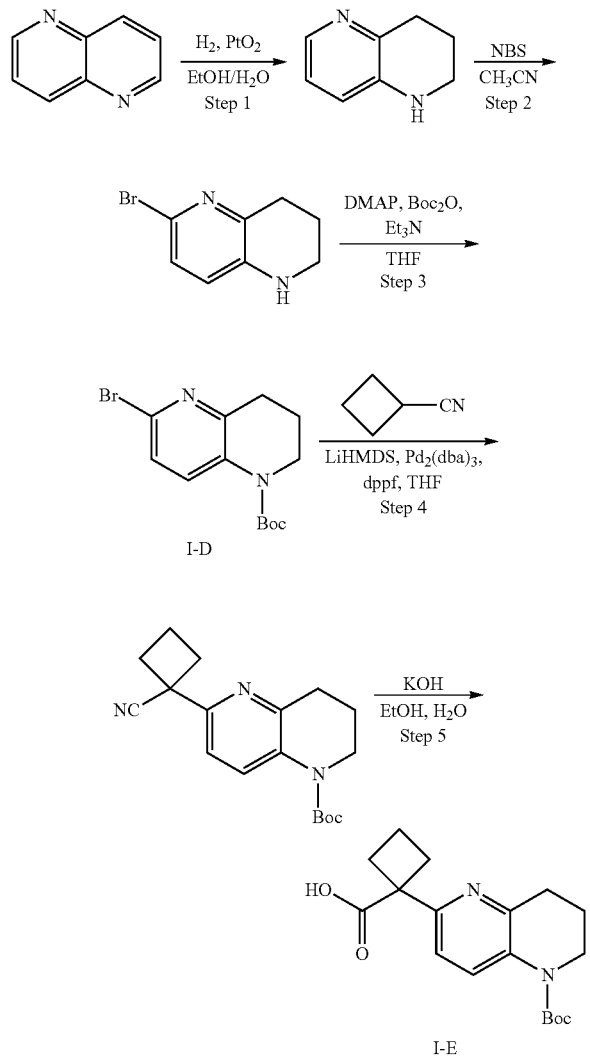

Step 1. 1,2,3,4-tetrahydro-1,5-naphthyridine

To a stirring solution of 1,5-naphthyridine (25 g, 192 mmol) in EtOH (342 mL) and water (18 mL) was added platinum(IV) oxide (2.5 g, 11.01 mmol) at 15° C. The reaction mixture was stirred under H$_2$ (45 psi) at 15° C. for 6 h. Then the reaction mixture was filtered through a celite, washed with MeOH. The filtrate was concentrated in vacuo to afford 1,2,3,4-tetrahydro-1,5-naphthyridine. $^1$H NMR (400 MHz, CD$_3$OD) δ7.62 (dd, J=4.6, 1.5 Hz, 1 H), 6.90-6.95 (m, 1 H), 6.83-6.86 (m, 1 H), 3.22-3.28 (m, 2 H), 2.84 (t, J=6.6 Hz, 2 H), 1.92-2.01 (m, 2 H).

Step 2. 6-bromo-1,2,3,4-tetrahydro-1,5-naphthyridine

To a solution of 1,2,3,4-tetrahydro-1,5-naphthyridine (15 g, 112 mmol) in acetonitrile (150 mL) was added NBS (20.1 g, 113 mmol) at 0° C. After the addition was finished, the reaction mixture was stirred at rt for 1.5 h. The solvent was concentrated in vacuo. The residue was diluted with DCM, washed with Na$_2$SO$_3$ (sat.). The organic layer was washed with brine, dried over Na$_2$SO$_4$, filtered and concentrated in vacuo to afford residue, which was purified by column chromatography on silica gel (EtOAc in petroleum ether: 0-25% gradient) to afford 6-bromo-1,2,3,4-tetrahydro-1,5-naphthyridine. $^1$H NMR (400 MHz, CDCl$_3$) δ7.02 (d, J=8.3 Hz, 1 H), 6.62 (d, J=8.3 Hz, 1 H), 3.53-3.47 (m, 1 H), 3.25-3.32 (m, 1H), 2.90 (t, J=6.5 Hz, 2 H), 2.04-1.96 (m, 2 H).

Step 3. tent-butyl 6-bromo-3,4-dihydro-1,5-naphthyridine-1(2H)-carboxylate (I-D)

To a stirring solution of 6-bromo-1,2,3,4-tetrahydro-1,5-naphthyridine (20 g, 94 mmol) in THF (60 mL) was added Et$_3$N (39.2 mL, 282 mmol), DMAP (3.33 g, 27.2 mmol) and Boc$_2$O (43.5 mL, 188 mmol) at 15° C. After the addition was finished, the reaction mixture was stirred at 80° C. for 8 h. Then another batch of Boc$_2$O (43.5 mL, 188 mmol) was added at 80° C. and the mixture was stirred at 80° C. for additional 12 h. The mixture was concentrated in vacuo to afford residue, which was purified by column chromatography on silica gel (EtOAc in petroleum ether: 0-5% gradient) to afford tent-butyl 6-bromo-3,4-dihydro-1,5-naphthyridine-1(2H)-carboxylate (I-D). MS (EI) m/z 257 [M−56+H]$^+$.

Step 4. tent-butyl 6-(1-cyanocyclobutyl)-3,4-dihydro-1,5-naphthyridine-1(2H)-carboxylate To a solution of I-D in THF (150 mL) were added dppf (1.770 g, 3.19 mmol), Pd$_2$(dba)$_3$ (1.462 g, 1.596 mmol), cyclobutanecarbonitrile (5.18 g, 63.9 mmol), and LiHMDS in THF (1 M, 63.9 mL, 63.9 mmol) at RT. The mixture was stirred at 80° C. for 16 h. The reaction was cooled down to RT, quenched with NH$_4$Cl (sat.), extracted with EtOAc. The combined organic layers were washed with brine, dried over Na$_2$SO$_4$, filtered and concentrated in vacuo to afford residue, which was purified by column chromatography on silica gel (EtOAc in petroleum ether: 5-12% gradient) to afford tert-butyl 6-(1-cyanocyclobutyl)-3,4-dihydro-1,5-naphthyridine-1(2H)-carboxylate. MS (EI) m/z 314 [M+H]$^+$.

Step 5. 1-(5-(tert-butoxycarbonyl)-5,6,7,8-tetrahydro-1,5-naphthyridin-2-yl)cyclobutanecarboxylic acid (I-E)

To a stirring solution of tent-butyl 6-(1-cyanocyclobutyl)-3,4-dihydro-1,5-naphthyridine-1(2H)-carboxylate (4.2 g, 13.40 mmol) in EtOH (80 mL) and water (40 mL) was added potassium hydroxide (2.63 g, 46.9 mmol) at 15° C. The mixture was stirred at 80° C. for 30 h. The reaction was cooled down to rt. HCl (aq., 1M) was added to adjust pH~6 and the reaction mixture was extracted with EtOAc. The combined organic layers were washed with brine, dried over Na$_2$SO$_4$, filtered and concentrated in vacuo to afford residue, which was purified by column chromatography on silica gel (MeOH in DCM: 5-10% gradient) to afford the title compound (I-E). $^1$H NMR (400 MHz, CD$_3$OD) δ8.04 (br t, J=9.6 Hz, 1 H), 7.20 (br dd, J=8.6, 2.4 Hz, 1 H), 3.71-3.76 (m, 2 H), 2.94 (q, J=6.7 Hz, 2 H), 2.71-2.79 (m, 2 H), 2.57-2.65 (m, 2 H), 1.95 -2.04 (m, 4 H), 1.52 (d, J=1.3 Hz, 9 H); MS (EI) m/z 333 [M+H]$^+$.

Example 13: Cyclopropyl(6-(1-(6-(trifluoromethyl)-3H-imidazo[4,5-b]pyridin-2-yl)cyclobutyl)-3,4-dihydro-1,5-naphthyridin-1(2H),-yl)methanone (Ex. 13)

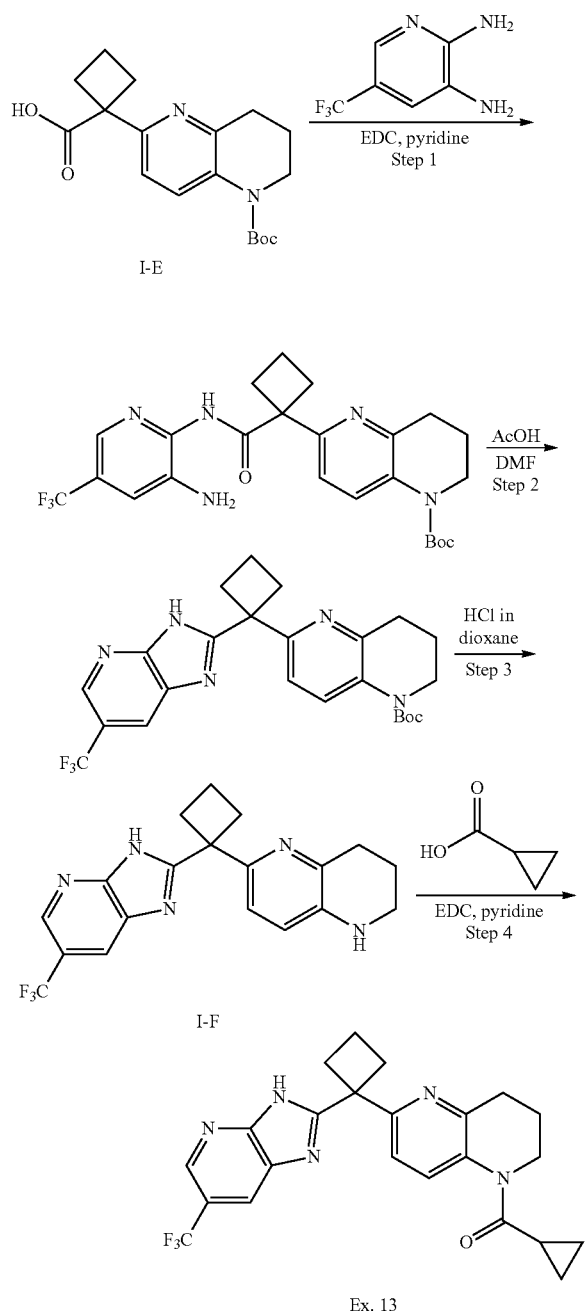

Step 1: tert-butyl 6-(1-((3-amino-5-(trifluoromethyl)pyridin-2-yl)carbamoyl)cyclobutyl)-3,4-dihydro-1,5-naphthyridine-1(2H),-carboxylate To a stirred solution of I-E (800 mg, 2.41 mmol) in pyridine (60 mL) were added EDC (1384 mg, 7.22 mmol) and 5-(trifluoromethyl)pyridine-2,3-diamine (384 mg, 2.17 mmol) at rt. The mixture was stirred at 40° C. for 3h, then cooled down to rt, diluted with water (100 mL), extracted with EtOAc. The combined organic layers were washed with brine, dried over $Na_2SO_4$, filtered and concentrated in vacuo to afford residue, which was purified by column chromatography on silica gel (EtOAc in petroleum ether: 0-30% gradient) to afford tert-butyl 6-(1-((3-amino-5-(trifluoromethyl)pyridin-2-yl)carbamoyl)cyclobutyl)-3,4-dihydro-1,5-naphthyridine-1(2H),-carboxylate. MS (EI) m/z 492 $[M+H]^+$.

Step 2: tert-butyl 6-(1-(6-(trifluoromethyl)-3H-imidazo[4,5-b]pyridin-2-yl)cyclobutyl)-3,4-dihydro-1,5-naphthyridine-1(2H),-carboxylate A solution of tert-butyl 6-(1-((3-amino-5-(trifluoromethyl)pyridin-2-yl)carbamoyl)cyclobutyl)-3,4-dihydro-1,5-naphthyridine-1(2H),-carboxylate (650 mg, 1.32 mmol) in DMF (5 mL) and acetic acid (1 mL) was stirred at 130° C. for 16 h. The reaction was cooled down to rt, diluted with water, extracted with EtOAc. The combined organic layers were washed with brine, dried over $Na_2SO_4$, filtered and concentrated in vacuo to afford the crude tert-butyl 6-(1-(6-(trifluoromethyl)-3H-imidazo[4,5-b]pyridin-2-yl)cyclobutyl)-3,4-dihydro-1,5-naphthyridine-1(2H),-carboxylate, which was used directly in next step without further purification. MS (EI) m/z 474 $[M+H]^+$.

Step 3: 6-(1-(6-(trifluoromethyl)-3H-imidazo[4,5-b]pyridin-2-yl)cyclobutyl)-1,2,3,4-tetrahydro-1,5-naphthyridine (I-F)

A solution of tert-butyl 6-(1-(6-(trifluoromethyl)-3H-imidazo[4,5-b]pyridin-2-yl)cyclobutyl)-3,4-dihydro-1,5-naphthyridine-1(2H),-carboxylate (625 mg, 1.32 mmol) in 4M HCl in dioxane solution (5 mL) was stirred at RT for 3 h. The solvent was evaporated in vacuo. The residue was diluted with water and the pH was adjust to ~8 by $NaHCO_3$ (aq., 2N). The aqueous solution was extracted with EtOAc. The combined organic layers were washed with brine, dried over $Na_2SO_4$, filtered and concentrated in vacuo to afford residue, which was purified by pre-TLC ($SiO_2$, petroleum ether: EtOAc=1:1) to give 6-(1-(6-(trifluoromethyl)-3H-imidazo[4,5-b]pyridin-2-yl)cyclobutyl)-1,2,3,4-tetrahydro-1,5-naphthyridine (I-F). MS (EI) m/z 374 $[M+H]^+$.

Step 4: Cyclopropyl(6-(1-(6-(trifluoromethyl)-3H-imidazo[4,5-b]pyridin-2-yl)cyclobutyl)-3,4-dihydro-1,5-naphthyridin-1(2H),-yl)methanone (Ex. 13)

To a solution of cyclopropanecarboxylic acid (9 mg, 0.1 mmol) in pyridine (3 mL) were added EDC (47 mg, 0.24 mmol) and I-F (30 mg, 0.080 mmol) at RT. The mixture was stirred at 60 ° C. for 3 h, then cooled down to rt, diluted with water, extracted with EtOAc. The combined organic layers were washed with brine, dried over $Na_2SO_4$, filtered and concentrated in vacuo to afford residue, which was purified by reversed phase HPLC, eluting with water (0.1%TFA)-ACN to afford the title compound as a TFA salt (Ex. 13). $^1$H NMR (400 MHz, $CD_3OD$) δ8.7 (d, J=0.9 Hz, 1 H), 8.4 (br d, J=8.3 Hz, 1 H), 8.3 (d, J=1.3 Hz, 1 H), 7.7 (d, J=8.8 Hz, 1 H), 4.0 (t, J=5.9 Hz, 2 H), 3.1-3.0 (m, 6 H), 2.3-2.2 (m, 1 H), 2.2-2.1 (m, 1 H), 2.1-2.0 (m, 3 H), 1.1 (q, J=3.7 Hz, 2 H), 0.9-1.0 (m, 2 H); MS (EI) m/z 442 $[M+H]^+$.

Example 14: (tetrahydro-2H-pyran-2-yl)(6-(1-(6-(trifluoromethyl)-1H-imidazo[4,5-b]pyridin-2-yl)cyclobutyl)-3,4-dihydro-1,5-naphthyridin-1(2H),-yl)methanone (Ex. 14)

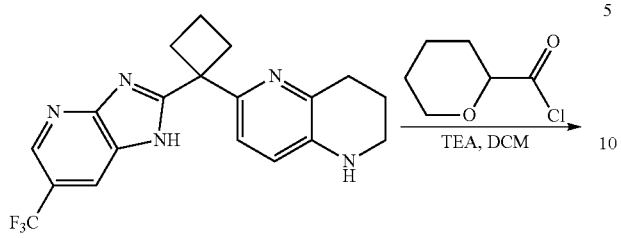

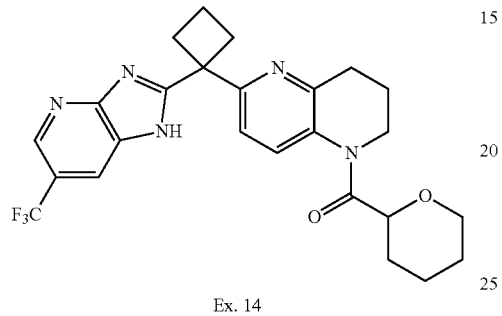

To a stirred solution of I-F (40 mg, 0.107 mmol) in DCM (1 mL) was added TEA (0.044 mL, 0.316 mmol) and tetrahydro-2H-pyran-2-carbonyl chloride (32 mg, 0.215 mmol) at rt. The reaction mixture was stirred at rt for 6 h, diluted with water, extracted with EtOAc. The combined organic layers were washed with brine, dried over $Na_2SO_4$, filtered and concentrated in vacuo to afford residue, which was purified by reversed phase HPLC, eluting with water (0.1% TFA)-ACN to afford the title compound as a TFA salt (Ex. 14). $^1$H NMR (400 MHz, $CD_3OD$) δ8.7 (s, 1 H), 8.4 (br d, J=7.5 Hz, 1 H), 8.3 (d, J=1.3 Hz, 1 H), 7.6 (d, J=8.6 Hz, 1 H), 4.4-4.3 (m, 1 H), 4.0-3.9 (m, 2 H), 3.8-3.7 (m, 1 H), 3.6-3.5 (m, 1 H), 3.1-3.0 (m, 6 H), 2.3-2.2 (m, 1 H), 2.2-2.0 (m, 3 H), 1.9 (br s, 1 H), 1.8-1.7 (m, 2 H), 1.7-1.5 (m, 3 H); MS (EI) m/z 486 [M+H]$^+$.

Example 15 and 16: (S)-(tetrahydro-2H-pyran-2-yl)(6-(1-(6-(trifluoromethyl)-1H-imidazo[4,5-b]pyridin-2-yl)cyclobutyl)-3,4-dihydro-1,5-naphthyridin-1(2H)-yl)methanone and (R)-(tetrahydro-2H-pyran-2-yl)(6-(1-(6-(trifluoromethyl)-1H-imidazo[4,5-b]pyridin-2-yl)cyclobutyl)-3,4-dihydro-1,5-naphthyridin-1(2H)-yl)methanone (Ex. 15 and Ex. 16)

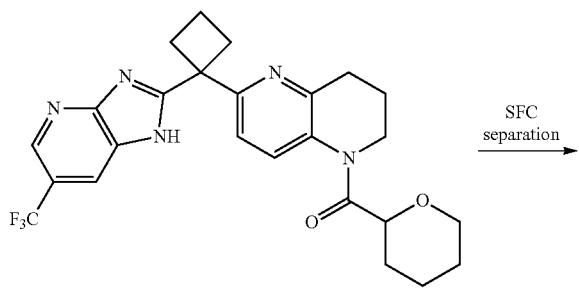

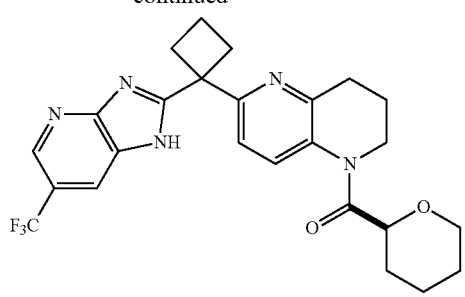

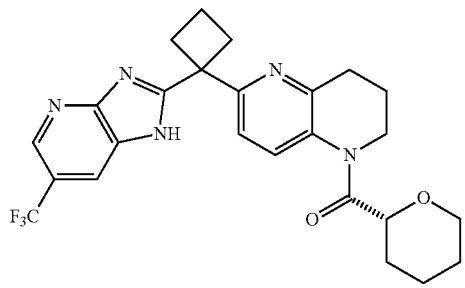

Example 14 was submitted to SFC chiral separation (Column: C2 250 mm×30 mm I.D., 10 um; Mobile phase A: CO2; Mobile phase B: 0.1% $NH_3H_2O$ in EtOH) to afford example 15 and 16.

Example 15: Retention Time: 4.59 Min $^1$H NMR (400 MHz, $CD_3OD$) δ8.7 (s, 1 H), 8.4 (br d, J=7.5 Hz, 1 H), 8.3 (d, J=1.3 Hz, 1 H), 7.6 (d, J=8.6 Hz, 1 H), 4.4-4.3 (m, 1 H), 4.0-3.9 (m, 2 H), 3.8-3.7 (m, 1 H), 3.6-3.5 (m, 1 H), 3.1-3.0 (m, 6 H), 2.3-2.2 (m, 1 H), 2.2-2.0 (m, 3 H), 1.9 (br s, 1 H), 1.8-1.7 (m, 2 H), 1.7-1.5 (m, 3 H); MS (EI) m/z 486 [M+H]$^+$.

Example 16: Retention Time: 5.11 min $^1$H NMR (400 MHz, $CD_3OD$) δ8.7 (s, 1 H), 8.4 (br d, J=7.5 Hz, 1 H), 8.3 (d, J=1.3 Hz, 1 H), 7.6 (d, J=8.6 Hz, 1 H), 4.4-4.3 (m, 1 H), 4.0-3.9 (m, 2 H), 3.8-3.7 (m, 1 H), 3.6-3.5 (m, 1 H), 3.1-3.0 (m, 6 H), 2.3-2.2 (m, 1 H), 2.2-2.0 (m, 3 H), 1.9 (br s, 1 H), 1.8-1.7 (m, 2 H), 1.7-1.5 (m, 3 H); MS (EI) m/z 486 [M+H]$^+$.

Example 17 showed in the following table was prepared in an analogous fashion to Example 14 using the corresponding acid chloride.

| Ex. No. | Structure | IUPAC Name | Exact Mass [M + H]+ |
|---|---|---|---|
| 17 | 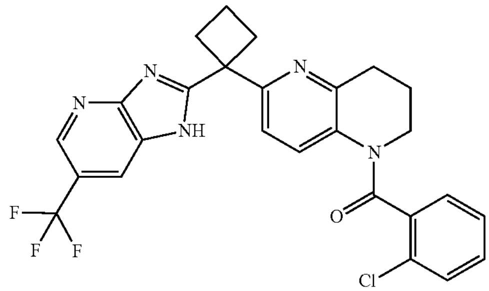 [SMILES: O=C(c1ccccc1Cl)N1CCCc2nc(C3(c4nc5ncc(C(F)(F)F)cc5[nH]4)CCC3)ccc21] | (2-chlorophenyl)[6-{1-[6-(trifluoromethyl)-1H-imidazo[4,5-b]pyridin-2-yl]cyclobutyl}-3,4-dihydro-1,5-naphthyridin-1(2H)-yl]methanone | Calc'd 512, found 512 |

Example 18: methyl 6-(1-(6-(trifluoromethyl)-3H-imidazo[4,5-b]pyridin-2-yl)cyclobutyl)-3,4-dihydro-1,5-naphthyridine-1(2H),-carboxylate (Ex. 18)

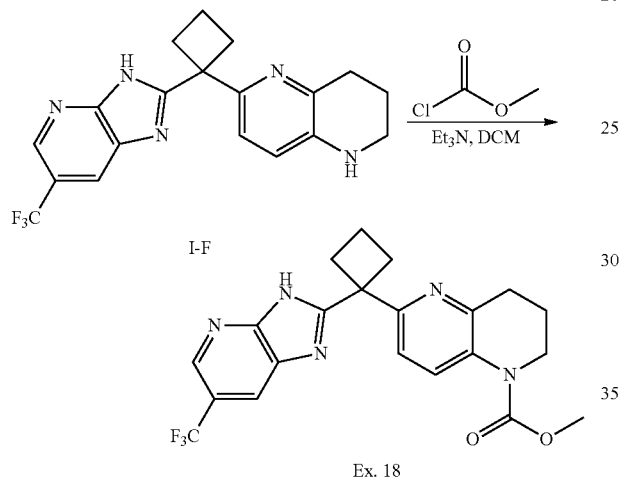

To a solution of I-F (50 mg, 0.134 mmol) in DCM (2 mL) were added TEA (0.055 mL, 0.395 mmol) and methyl carbonochloridate (16 mg, 0.169 mmol) at 0° C. The reaction mixture was stirred at rt for 16 h, diluted with water, extracted with EtOAc. The combined organic layers were washed with brine, dried over $Na_2SO_4$, filtered and concentrated in vacuo to afford residue, which was purified by reversed phase HPLC, eluting with water (0.1% TFA)-ACN to afford the title compound as a TFA salt (Ex. 18). $^1$H NMR (400 MHz, $CD_3OD$) δ8.7 (s, 2 H), 8.2 (br s, 1 H), 7.7 (br s, 1 H), 3.9 (br d, J=5.3 Hz, 2 H), 3.8 (d, J=2.2 Hz, 3 H), 3.1 (br d, J=6.6 Hz, 6 H), 2.3 (br s, 1 H), 2.2 (br s, 1 H), 2.1-2.0 (m, 2 H); MS (ESI) m/z: 432.0 [M+H]$^+$.

Example 19-24 in the following table were prepared in an analogous fashion to Example 18, using the corresponding aryl diamines and corresponding chloroformate.

| Ex | Structure | IUPAC Name | Exact Mass [M + H]+ |
|---|---|---|---|
| 19 | 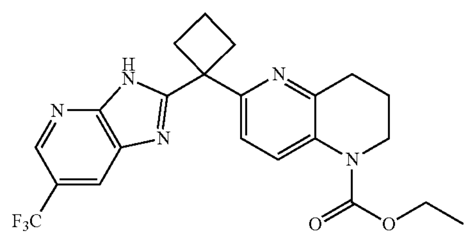 [SMILES: CCOC(=O)N1CCCc2nc(C3(c4nc5cc(C(F)(F)F)cnc5[nH]4)CCC3)ccc21] | ethyl 6-{1-[6-(trifluoromethyl)-3H-imidazo[4,5-b]pyridin-2-yl]cyclobutyl}-3,4-dihydro-1,5-naphthyridine-1(2H)-carboxylate | Calc'd 446, found 446 |
| 20 | 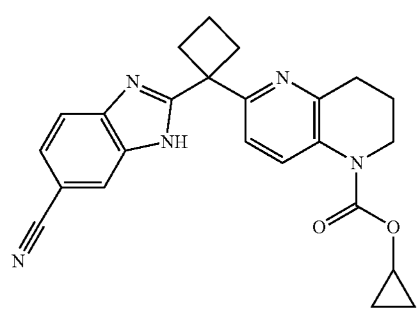 [SMILES: N#Cc1ccc2nc(C3(c4ccc5c(n4)CCCN5C(=O)OC4CC4)CCC3)[nH]c2c1] | cyclopropyl 6-[1-(6-cyano-1H-benzimidazol-2-yl)cyclobutyl]-3,4-dihydro-1,5-naphthyridine-1(2H)-carboxylate | Calc'd 414, found 414 |

-continued

| Ex | Structure | IUPAC Name | Exact Mass [M + H]+ |
|---|---|---|---|
| 21 | 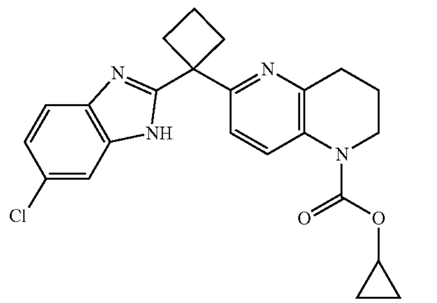 [SMILES: O=C(OC1CC1)N1CCCc2nc(C3(c4nc5ccc(Cl)cc5[nH]4)CCC3)ccc21] | cyclopropyl 6-[1-(6-chloro-1H-benzimidazol-2-yl)cyclobutyl]-3,4-dihydro-1,5-naphthyridine-1(2H)-carboxylate | Calc'd 423, found 423 |
| 22 | 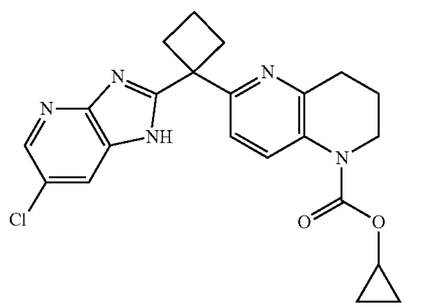 [SMILES: O=C(OC1CC1)N1CCCc2nc(C3(c4nc5ncc(Cl)cc5[nH]4)CCC3)ccc21] | cyclopropyl 6-[1-(6-chloro-1H-imidazo[4,5-b]pyridin-2-yl)cyclobutyl]-3,4-dihydro-1,5-naphthyridine-1(2H)-carboxylate | Calc'd 424, found 424 |
| 23 | 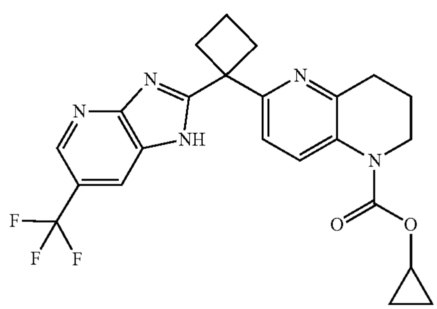 [SMILES: O=C(OC1CC1)N1CCCc2nc(C3(c4nc5ncc(C(F)(F)F)cc5[nH]4)CCC3)ccc21] | cyclopropyl 6-{1-[6-(trifluoromethyl)-1H-imidazo[4,5-b]pyridin-2-yl]cyclobutyl}-3,4-dihydro-1,5-naphthyridine-1(2H)-carboxylate | Calc'd 458, found 458 |
| 24 | 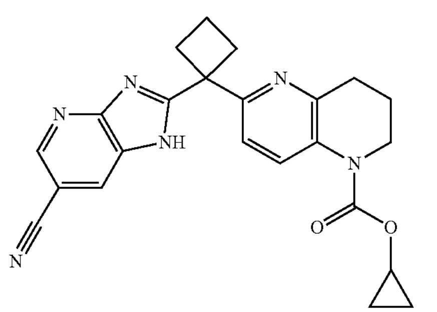 [SMILES: N#Cc1cnc2nc(C3(c4ccc5c(n4)CCCN5C(=O)OC4CC4)CCC3)[nH]c2c1] | cyclopropyl 6-[1-(6-cyano-1H-imidazo[4,5-b]pyridin-2-yl)cyclobutyl]-3,4-dihydro-1,5-naphthyridine-1(2H)-carboxylate | Calc'd 415, found 415 |

Intermediate I-G

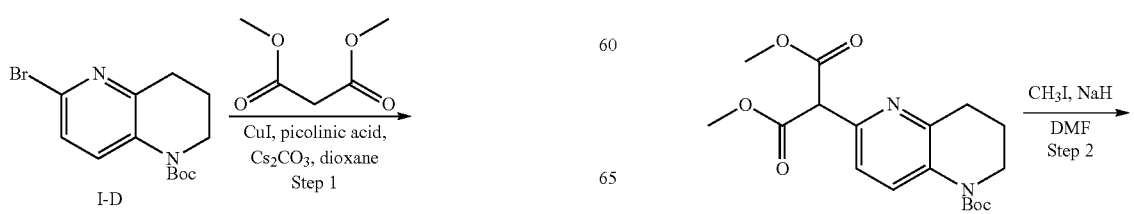

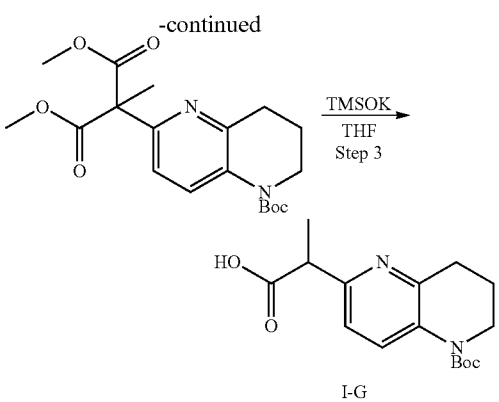

Step 1. Dimethyl 2-(5-(tert-butoxycarbonyl)-5,6,7,8-tetrahydro-1,5-naphthyridin-2-yl)malonate To a solution of tent-butyl 6-bromo-3,4-dihydro-1,5-naphthyridine-1(2H)-carboxylate (10.0 g, 31.9 mmol) and picolinic acid (3.14 g, 25.5 mmol) in 1,4-dioxane (100 mL) were added copper(I) iodide (0.61 g, 3.19 mmol), $Cs_2CO_3$ (31.2 g, 96.0 mmol) and dimethyl malonate (16.87 g, 128 mmol) at rt. Then the mixture was stirred at 100° C. for 16 h. The reaction mixture was cooled down to rt, diluted with EtOAc and filtered. The filtrate was concentrated in vacuo. The residue was purified by column chromatography on silica gel (EtOAc in petroleum ether: 0-15% gradient) to give dimethyl 2-(5-(tert-butoxycarbonyl)-5,6,7,8-tetrahydro-1,5-naphthyridin-2-yl)malonate. MS (EI) m/z 365 [M+H]+.

Step 2. dimethyl 2-(5-(tert-butoxycarbonyl)-5,6,7,8-tetrahydro-1,5-naphthyridin-2-yl)-2-methylmalonate To a solution of dimethyl 2-(5-(tert-butoxycarbonyl)-5,6,7,8-tetrahydro-1,5-naphthyridin-2-yl)malonate (3.0 g, 8.2 mmol) in DMF (25 mL) was added NaH (60%, 0.4 g, 10 mmol) at 0° C. After the addition was finished, the mixture was stirred at 0° C. for 10 min, then MeI (0.62 mL, 9.87 mmol) was added at 0° C. After the addition was finished, the reaction mixture was stirred at 0° C. for 1 h. The reaction was quenched with $NH_4Cl$ (sat. 120 mL), extracted with EtOAc. The combined organic layers were washed with brine, dried over $Na_2SO_4$, filtered and concentrated in vacuo to afford residue, which was purified by column chromatography on silica gel (EtOAc in petroleum ether: 0-30% gradient) to give dimethyl 2-(5-(tert-butoxycarbonyl)-5,6,7,8-tetrahydro-1,5-naphthyridin-2-yl)-2-methylmalonate. MS (EI) m/z 379 [M+H]+.

Step 3. 2-(5-(tert-butoxycarbonyl)-5,6,7,8-tetrahydro-1,5-naphthyridin-2-yl)propanoic acid (I-G)

To a solution of dimethyl 2-(5-(tert-butoxycarbonyl)-5,6,7,8-tetrahydro-1,5-naphthyridin-2-yl)-2-methylmalonate (1000 mg, 2.64 mmol) in THF (20 mL) was added TMSOK (1356 mg, 10.57 mmol) at RT. The mixture was stirred at RT for 15 h, diluted with water, adjusted to pH 6-7 with acetic acid, then extracted with EtOAc. The combined organic layers were washed with brine, dried over $Na_2SO_4$, filtered and concentrated in vacuo to afford crude 2-(5-(tert-butoxycarbonyl)-5,6,7,8-tetrahydro-1,5-naphthyridin-2-yl)pro- panoic acid (I-G), which was used directly in the next step without further purification. MS (EI) m/z 307 [M+H]+.

Example 25: cyclopropyl 6-(1-(6-chloro-1H-benzo[d]imidazol-2-yl)ethyl)-3,4-dihydro-1,5-naphthyridine-1(2H)-carboxylate

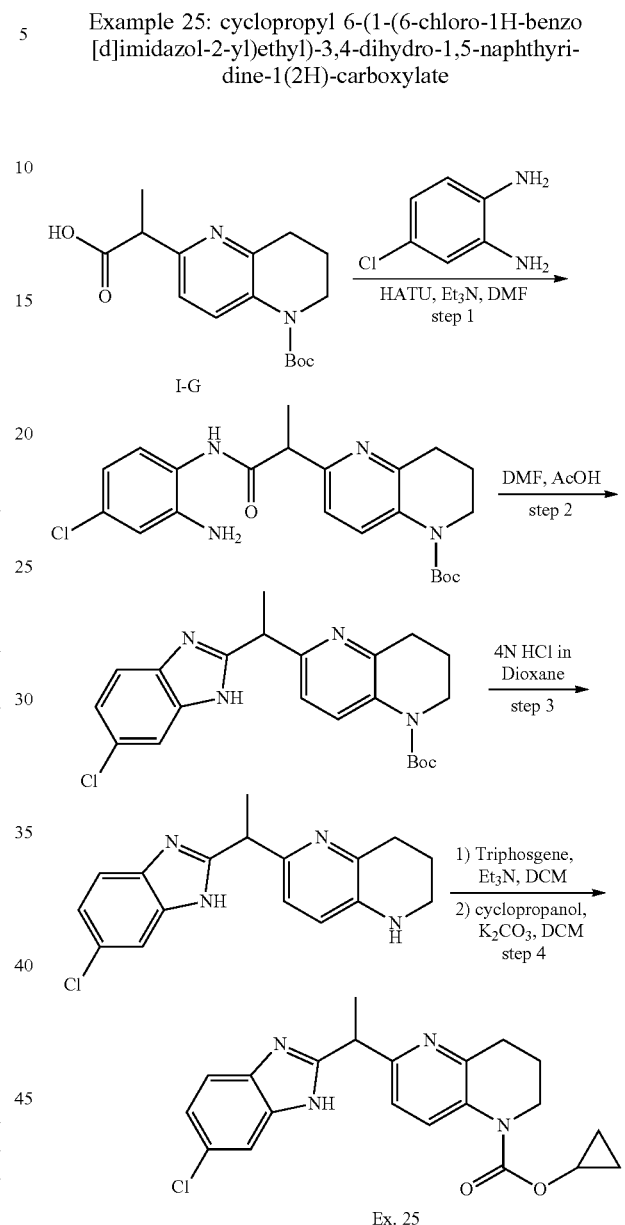

Ex. 25

Step 1: tert-butyl 6-(1-((2-amino-4-chlorophenyl)amino)-1-oxopropan-2-yl)-3,4-dihydro-1,5-naphthyridine-1(2H)-carboxylate To a stirred solution of I-G (400 mg, 1.31 mmol) in DMF (10 mL) was added $Et_3N$ (0.546 mL, 3.92 mmol), HATU (596 mg, 1.567 mmol) and 4-chlorobenzene-1,2-diamine (223 mg, 1.57 mmol) at rt. The mixture was stirred at rt for 16 h. The solvent was removed in vacuo. The residue was diluted with water, extracted with EtOAc. The combined organic layers were washed with brine, dried over $Na_2SO_4$, filtered and concentrated in vacuo to afford residue, which was purified by column chromatography on silica gel (EtOAc in petroleum ether: 10-70% gradient) to give tert-butyl 6-(1-((2-amino-4-chlorophenyl)amino)-1-oxopropan-2-yl)-3,4-dihydro-1,5-naphthyridine-1(2H)-carboxylate. MS (EI) m/z: 431 [M+H]⁺.

Step 2: tert-butyl 6-(1-(6-chloro-1H-benzo[d]imidazol-2-yl)ethyl)-3,4-dihydro-1,5-naphthyridine-1(2H)-carboxylate Tert-butyl 6-(1-((2-amino-4-chlorophenyl)amino)-1-oxopropan-2-yl)-3,4-dihydro-1,5-naphthyridine-1(2H)-carboxylate (170 mg, 0.394 mmol) was dissolved in AcOH (10 mL) and then stirred at 120° C. for 4 h. The solvent was removed in vacuo. The residue was diluted with NaHCO₃ (sat.), extracted with EtOAc. The combined organic layers were washed with brine, dried over Na₂SO₄, filtered and concentrated in vacuo to give the crude tert-butyl 6-(1-(6-chloro-1H-benzo[d]imidazol-2-yl)ethyl)-3,4-dihydro-1,5-naphthyridine-1(2H)-carboxylate, which was used for next step directly without further purification. MS (EI) m/z 313 [M−101+H]⁺.

Step 3: 6-(1-(6-chloro-1H-benzo[d]imidazol-2-yl)ethyl)-1,2,3,4-tetrahydro-1,5-naphthyridine To a stirred solution of tert-butyl 6-(1-(6-chloro-1H-benzo[d]imidazol-2-yl)ethyl)-3,4-dihydro-1,5-naphthyridine-1(2H)-carboxylate (140 mg, 0.339 mmol) in 1,4-Dioxane (1 mL) was added HCl in dioxane (4 M, 0.5 mL, 2.0 mmol) at rt. The reaction mixture was stirred at rt for 2 h. Then the solvent was removed in vacuo to give the crude 6-(1-(6-chloro-1H-benzo[d]imidazol-2-yl)ethyl)-1,2,3,4-tetrahydro-1,5-naphthyridine, which was used in next step directly without further purification. MS (EI) m/z 313 [M+H]⁺.

Step 4: cyclopropyl 6-(1-(6-chloro-1H-benzo[d]imidazol-2-yl)ethyl)-3,4-dihydro-1,5-naphthyridine-1(2H)-carboxylate (Ex.25)

To a stirred solution of 6-(1-(6-chloro-1H-benzo[d]imidazol-2-yl)ethyl)-1,2,3,4-tetrahydro-1,5-naphthyridine (70 mg, 0.224 mmol) in DCM (3 ml) was added Et₃N (0.060 mL, 0.43 mmol) and triphosgene (73.0 mg, 0.246 mmol) at 0° C. After the addition was finished, the reaction mixture was stirred at 25° C. for 1 h. The reaction was quenched with NaHCO₃ (sat.), extracted with DCM. The combined organic layers were washed with brine, dried over Na₂SO₄, filtered and concentrated in vacuo to afford residue. The residue was dissolved in DCM (2 mL), K₂CO₃ (74 mg, 0.54 mmol) and cyclopropanol (130 mg, 2.24 mmol) were added at 25° C. After the addition was finished, the reaction was stirred at 60° C. for 16 h. The reaction mixture was filtered, concentrated and purified by reversed phase HPLC, eluting with water (0.1% TFA)-ACN to afford the title compound as a TFA salt (Ex. 25). ¹H NMR (400 MHz, CD₃OD) δ8.15 (d, J=7.6 Hz, 1H), 7.55-7.64 (m, 2H), 7.36 (dd, J=2.0, 8.4 Hz, 1H), 7.22 (d, J=8.8 Hz, 1H), 4.64 (q, J=7.2 Hz, 1H), 4.11-4.20 (m, 1H), 3.69-3.76 (m, 2H), 2.86-2.97 (m, 2H), 1.91-2.03 (m, 2H), 1.83 (d, J=7.2 Hz, 3H), 0.74 (d, J=4.4 Hz, 4H); MS (EI) m/z 397 [M+H]⁺.

Example 26 and 27: cyclopropyl (S)-6-(1-(6-chloro-1H-benzo[d]imidazol-2-yl)ethyl)-3,4-dihydro-1,5-naphthyridine-1(2H)-carboxylate and cyclopropyl (R)-6-(1-(6-chloro-1H-benzo[d]imidazol-2-yl)ethyl)-3,4-dihydro-1,5-naphthyridine-1(2H)-carboxylate (Ex. 26 and Ex.27)

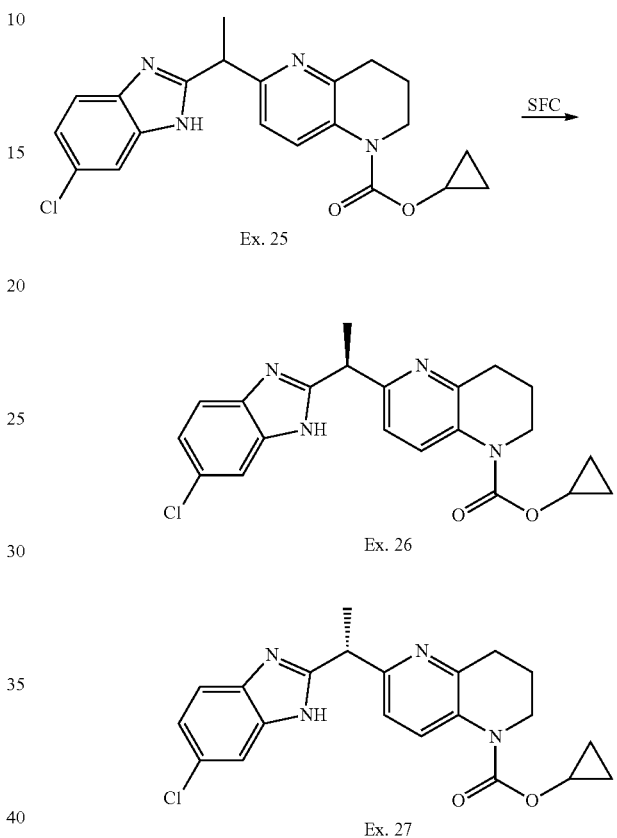

Example 25 was submitted to SFC chiral separation (Column: AD 250 mm×30 mm I.D., 10 um; Mobile phase A: CO₂; Mobile phase B: 0.1% NH₃H₂O in IPA) to afford example 26 and 27.

Example 26: Retention Time: 1.558 min

¹H NMR (400 MHz, CD₃OD) δ8.15 (d, J=7.6 Hz, 1H), 7.55-7.64 (m, 2H), 7.36 (dd, J=2.0, 8.4 Hz, 1H), 7.22 (d, J=8.8 Hz, 1H), 4.64 (q, J=7.2 Hz, 1H), 4.11-4.20 (in, 1H), 3.69-3.76 (m, 2H), 2.86-2.97 (m, 2H), 1.91-2.03 (m, 2H), 1.83 (d, =7.2 Hz, 3H), 0.74 (d, J=4.4 Hz, 4H); MS (EI) m/z 397 [M+H]⁺.

Example 27: Retention Time: 1.986 min

¹HNMR (400 MHz, CD₃OD) δ8.15 (d, J=7.6 Hz, 1H), 7.55-7.64 (m, 2H), 7.36 (dd, J=2.0, 8.4 Hz, 1H), 7.22 (d, J=8.8 Hz, 1H), 4.64 (q, J=7.2 Hz, 1H), 4.11-4.20 (m, 1H), 3.69-3.76 (m, 2H), 2.86-2.97 (m, 2H), 1.91-2.03 (m, 2H), 1.83 (d, J=7.2 Hz, 3H), 0.74 (d, J=4.4 Hz, 4H); MS (EI) m/z 397 [M+H]⁺.

Example 28: cyclopropyl 6-(1-(6-cyano-1H-imidazo[4,5-b]pyridin-2-yl)ethyl)-3,4-dihydro-1,5-naphthyridine-1(2H)-carboxylate (Ex. 28)

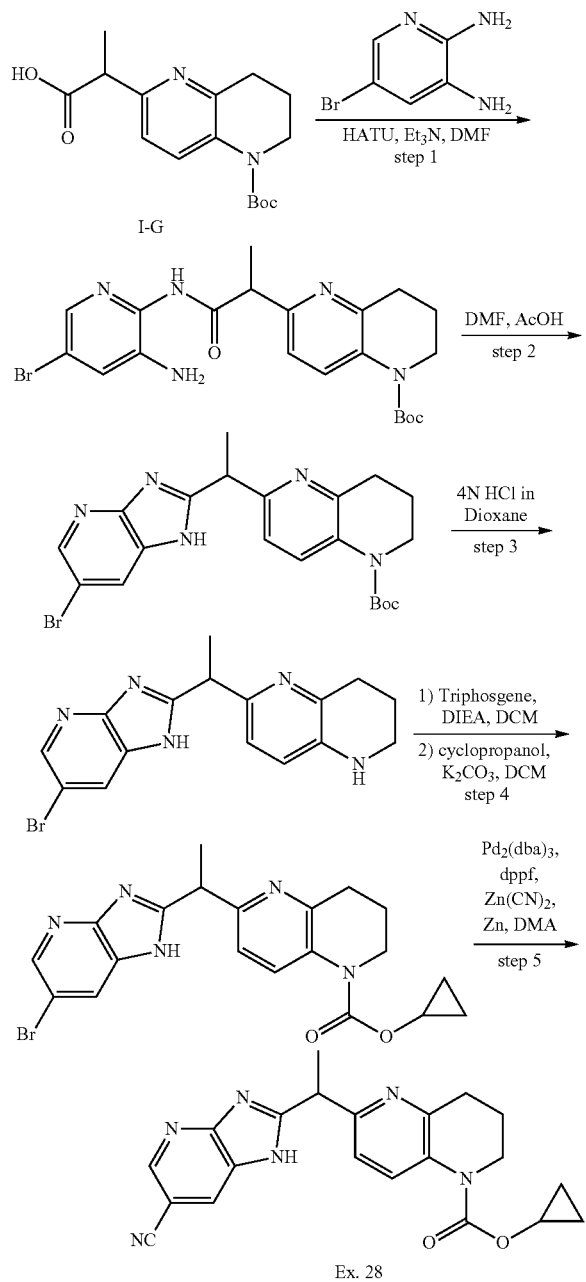

Step 1: tert-butyl 6-(1-((3-amino-5-bromopyridin-2-yl)amino)-1-oxopropan-2-yl)-3,4-dihydro-1,5-naphthyridine-1(2H)-carboxylate To a stirred solution of I-G (730 mg, 2.38 mmol) in DMF (20 mL) were added HATU (1370 mg, 3.60 mmol), 5-bromopyridine-2,3-diamine (672 mg, 3.57 mmol) and Et$_3$N (1.0 mL) at RT. The mixture was stirred at rt for 16 h. The solvent was removed in vacuo. The residue was diluted with water, extracted with EtOAc. The combined organic layers were washed with brine, dried over Na$_2$SO$_4$, filtered and concentrated in vacuo to afford residue, which was purified by column chromatography on silica gel (EtOAc in petroleum ether: 10-40% gradient) to afford tert-butyl 6-(1-((3-amino-5-bromopyridin-2-yl)amino)-1-oxopropan-2-yl)-3,4-dihydro-1,5-naphthyridine-1(2H)-carboxylate. MS (EI) m/z 476 [M+H]$^+$.

Step 2: tert-butyl 6-(1-(6-bromo-1H-imidazo[4,5-b]pyridin-2-yl)ethyl)-3,4-dihydro-1,5-naphthyridine-1(2H)-carboxylate A solution of tert-butyl 6-(1-((3-amino-5-bromopyridin-2-yl)amino)-1-oxopropan-2-yl)-3,4-dihydro-1,5-naphthyridine-1(2H)-carboxylate (1.0 g, 2.1 mmol) in DMF (20 mL) and AcOH (5 mL) was stirred at 130° C. for 16 h. The reaction mixture was concentrated in vacuo to give the crude product tert-butyl 6-(1-(6-bromo-1H-imidazo[4,5-b]pyridin-2-yl)ethyl)-3,4-dihydro-1,5-naphthyridine-1(2H)-carboxylate, which was used in the next step without further purification. MS (EI) m/z 458 [M+H]$^+$.

Step 3: 6-(1-(6-bromo-1H-imidazo[4,5-b]pyridin-2-yl)ethyl)-1,2,3,4-tetrahydro-1,5-naphthyridine To a stirred solution tert-butyl 6-(1-(6-bromo-1H-imidazo[4,5-b]pyridin-2-yl)ethyl)-3,4-dihydro-1,5-naphthyridine-1(2H)-carboxylate (700 mg, 1.527 mmol) in MeOH (5 mL) was added HCl in dioxane (4 M, 0.382 ml, 1.53 mmol) at rt. The mixture was stirred at rt for 16 h, then concentrated in vacuo. The residue was dissolved in NaHCO$_3$(sat.) and extracted with EtOAc. The combined organic layers were washed with brine, dried over Na$_2$SO$_4$, filtered and concentrated in vacuo to afford residue, which was purified by column chromatography on silica gel (EtOAc in petroleum ether: 0-90% gradient) to give 6-(1-(6-bromo-1H-imidazo[4,5-b]pyridin-2-yl)ethyl)-1,2,3,4-tetrahydro-1,5-naphthyridine. MS (EI) m/z 358 [M+H]$^+$.

Step 4: cyclopropyl 6-(1-(6-bromo-1H-imidazo[4,5-b]pyridin-2-yl)ethyl)-3,4-dihydro-1,5-naphthyridine-1(2H)-carboxylate To a stirred solution of 6-(1-(6-bromo-1H-imidazo[4,5-b]pyridin-2-yl)ethyl)-1,2,3,4-tetrahydro-1,5-naphthyridine (250 mg, 0.698 mmol) in DCM (10 mL) was added DIEA (0.30 mL, 2.1 mmol) and triphosgene (311 mg, 1.05 mmol) at 0° C. After the addition was finished, the mixture was stirred at rt for 1 h, quenched with NaHCO$_3$(sat.), and extracted with DCM. The combined organic layers were washed with brine, dried over Na$_2$SO$_4$, filtered and concentrated in vacuo to afford residue. The residue was dissolved in DCM (3 mL), K$_2$CO$_3$ (246 mg, 1.78 mmol) and cyclopropanol (345 mg, 5.94 mmol) were added at RT. After the addition was finished, the reaction was stirred at 60° C. for 16 h. The mixture was diluted with water and extracted with DCM. The combined organic layers were washed with brine, dried over Na$_2$SO$_4$, filtered and concentrated in vacuo to afford residue, which was purified by prep-TLC (petroleum ether: EtOAc=1:1) to give cyclopropyl 6-(1-(6-bromo-1H-imidazo[4,5-b]pyridin-2-yl)ethyl)-3,4-dihydro-1,5-naphthyridine-1(2H)-carboxylate. MS (EI) m/z 442 [M+H]$^+$.

Step 5: cyclopropyl 6-(1-(6-cyano-1H-imidazo[4,5-b]pyridin-2-yl)ethyl)-3,4-dihydro-1,5-naphthyridine-1(2H)-carboxylate (Ex. 28)

To a solution of cyclopropyl 6-(1-(6-bromo-1H-imidazo[4,5-b]pyridin-2-yl)ethyl)-3,4-dihydro-1,5-naphthyridine-1

(2H)-carboxylate (50 mg, 0.11 mmol), dppf (19 mg, 0.034 mmol) and zinc (15 mg, 0.23 mmol) in DMA (2 mL) were added Zn(CN)$_2$ (26 mg, 0.22 mmol) and Pd$_2$(dba)$_3$ (16 mg, 0.017 mmol) at rt. After the addition was finished, the reaction mixture was irradiated in microwave at 150° C. for 1 h. The mixture was filtered, concentrated, and purified by reversed phase HPLC, eluting with water (0.1% TFA)-ACN to afford the title compound as a TFA salt (Ex. 28). $^1$H NMR (400 MHz, CD$_3$OD) δ8.64 (s, 1 H), 8.28 (s, 1 H), 8.09 (br s, 1 H), 7.20 (d, J=8.8 Hz, 1 H), 4.60 (br d, J=3.1 Hz, 1 H), 4.11-4.17 (m, 1 H), 3.70-3.75 (m, 2 H), 2.91 (t, J=6.62 Hz, 2 H), 1.95-2.02 (m, 2 H), 1.82 (d, J=7.3 Hz, 3 H), 0.73 (d, J=4.6 Hz, 4 H), MS (ESI) m/z: 389 [M+H]$^+$.

Example 29: cyclopropyl 6-(1-(6-cyano-1H-benzo[d]imidazol-2-yl)ethyl)-3,4-dihydro-1,5-naphthyridine-1(2H)-carboxylate (Ex 29)

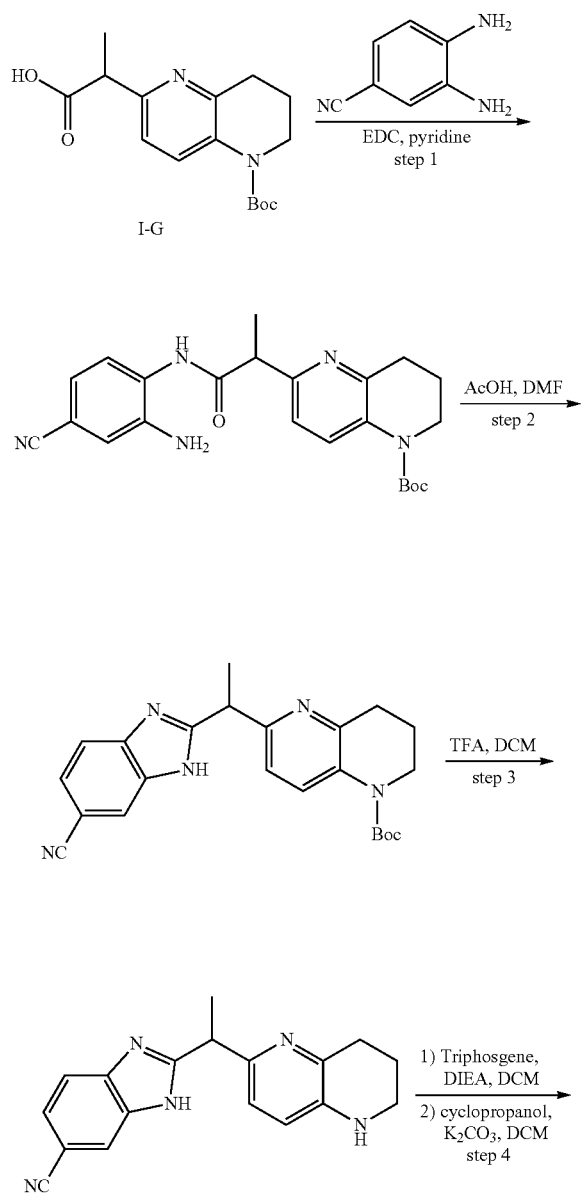

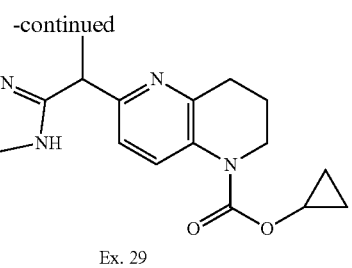

Ex. 29

Step 1: tert-butyl 6-(1-((2-amino-4-cyanophenyl)amino)-1-oxopropan-2-yl)-3,4-dihydro-1,5-naphthyridine-1(2H)-carboxylate To a stirred solution of 2-(5-(tert-butoxycarbonyl)-5,6,7,8-tetrahydro-1,5-naphthyridin-2-yl)propanoic acid (1.0 g, 3.3 mmol) in pyridine (30 mL) was added EDC (1.88 g, 9.79 mmol) and 3,4-diaminobenzonitrile (0.652 g, 4.90 mmol) at rt. The mixture was stirred at rt for 3 h. The reaction was diluted with water, extracted with EtOAc. The combined organic layers were washed with brine, dried over Na$_2$SO$_4$, filtered and concentrated in vacuo to afford residue, which was purified by column chromatography on silica gel (EtOAc in petroleum ether: 0-100% gradient) to give tert-butyl 6-(1-((2-amino-4-cyanophenyl)amino)-1-oxopropan-2-yl)-3,4-dihydro-1,5-naphthyridine-1(2H)-carboxylate. MS (EI) m/z 422 [M+H]$^+$.

Step 2: tert-butyl 6-(1-(6-cyano-1H-benzo[d]imidazol-2-yl)ethyl)-3,4-dihydro-1,5-naphthyridine-1(2H)-carboxylate To a stirred solution of tert-butyl 6-(1-((2-amino-4-cyanophenyl)amino)-1-oxopropan-2-yl)-3,4-dihydro-1,5-naphthyridine-1(2H)-carboxylate (250 mg, 0.593 mmol) in DMF (8 mL) was added acetic acid (2 mL) at rt. After the addition was finished, the reaction was stirred at 130° C. for 15 h. The reaction was cooled down to rt, concentrated in vacuo, diluted with water and extracted with EtOAc. The combined organic layers were washed with brine, dried over Na$_2$SO$_4$, filtered and concentrated in vacuo to afford residue, which was purified by column chromatography on silica gel (EtOAc in petroleum ether: 50-100% gradient) to give tert-butyl 6-(1-(6-cyano-1H-benzo[d]imidazol-2-yl)ethyl)-3,4-dihydro-1,5-naphthyridine-1(2H)-carboxylate. MS (ESI) m/z: 404 [M+H]$^+$.

Step 3: 2-(1-(5,6,7,8-tetrahydro-1,5-naphthyridin-2-yl)ethyl)-1H-benzo[d]imidazole-6-carbonitrile To a stirred solution of tert-butyl 6-(1-(6-cyano-1H-benzo[d]imidazol-2-yl)ethyl)-3,4-dihydro-1,5-naphthyridine-1(2H)-carboxylate (128 mg, 0.317 mmol) in DCM (10 mL) was added TFA (36.2 mg, 0.317 mmol) at RT. The mixture was stirred at rt for 5 h. The solvent was removed in vacuo. The residue was purified by column chromatography on silica gel (MeOH in DCM: 0-10% gradient) to give 2-(1-(5,6,7,8-tetrahydro-1,5-naphthyridin-2-yl)ethyl)-1H-benzo[d]imidazole-6-carbonitrile. MS (ESI) m/z: 304 [M+H]$^+$.

Step 4: cyclopropyl 6-(1-(6-cyano-1H-benzo[d]imidazol-2-yl)ethyl)-3,4-dihydro-1,5-naphthyridine-1(2H)-carboxylate (Ex. 29)

To a stirred solution of 2-(1-(5,6,7,8-tetrahydro-1,5-naphthyridin-2-yl)ethyl)-1H-benzo[d]imidazole-5-carbonitrile (90 mg, 0.30 mmol) in DCM (10 mL) was added DIEA (0.124 mL, 0.890 mmol) and triphosgene (140 mg, 0.472 mmol) at 0° C. After the addition was finished, the reaction was stirred at rt for 1 h. The reaction was quenched with NaHCO₃(sat.) and extracted with DCM. The combined organic layers were washed with brine, dried over Na₂SO₄, filtered and concentrated in vacuo to afford residue. The residue was dissolved in DCM (5 mL), K₂CO₃ (123 mg, 0.890 mmol) and cyclopropanol (172 mg, 2.97 mmol) were added at 0° C. and then stirred at 60° C. for 15 h. The reaction was diluted with water, extracted with DCM. The combined organic layers were washed with brine, dried over Na₂SO₄, filtered and concentrated in vacuo to afford residue, which was purified by reversed phase HPLC, eluting with water (0.1% TFA)-ACN to afford the title compound as a TFA salt (Ex. 29). ¹H NMR (400 MHz, CDCl₃) δ8.1 (s, 1 H), 7.8 (s, 1 H), 7.5 (br s, 2 H), 7.4-7.3 (m, 1 H), 7.2 (d, J=8.8 Hz, 1 H), 4.5 -4.6 (m, 1 H) 4.1-4.2 (m, 1 H) 3.7-3.8 (m, 2 H) 3.0-3.1 (m, 2 H) 2.1 (br s, 2 H) 1.8 (d, J=7.4 Hz, 3 H) 0.8-0.9 (m, 4 H). MS (EI) m/z 388 [M+H]⁺.

Example 30: 1-(2-methylpyrimidin-4-yl)-6-(1-(6-(trifluoromethyl)-3H-imidazo[4,5-b]pyridin-2-yl)cyclobutyl)-1,2,3,4-tetrahydro-1,5-naphthyridine (Ex. 30)

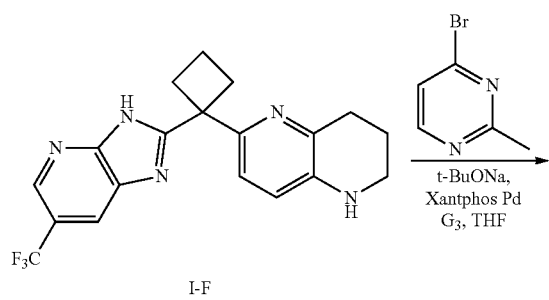

I-F

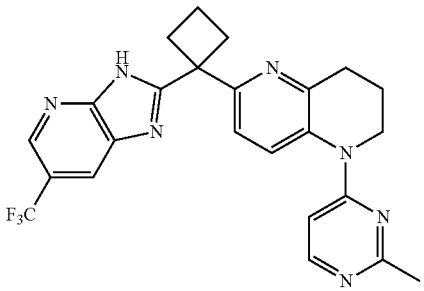

Ex. 30

To a stirred solution of I-F (60 mg, 0.16 mmol) and 4-bromo-2-methylpyrimidine (42 mg, 0.24 mmol) in THF (3 mL) was added and XantPhos Pd G3 (15 mg, 0.016 mmol) and sodium tert-butoxide (46 mg, 0.48 mmol) at rt. After the addition was finished, the reaction was stirred at 60° C. for 15 h. The reaction mixture was filtered and purified by reversed phase HPLC, eluting with water (0.1% TFA)-ACN to afford the title compound as a TFA salt (Ex. 30). ¹H NMR (400 MHz, CDCl₃) δ8.6 (s, 1 H), 8.3-8.4 (m, 2 H), 7.9 (d, J=8.6 Hz, 1 H), 7.5 (d, J=8.6 Hz, 1 H), 7.0 (d, J=7.1 Hz, 1 H), 4.1 (br t, J=6.3 Hz, 3 H), 3.2 (br t, J=6.7 Hz, 4 H), 2.9-3.0 (m, 2 H), 2.7 (s, 3 H), 2.3-2.4 (m, 1 H), 2.2-2.2 (m, 2 H), 2.1-2.2 (m, 1 H); MS (EI) m/z 466 [M+H]⁺.

Example 31-36 in the following table were prepared in an analogous fashion to intermediate I-F and Example 30, using the corresponding aryl diamines and corresponding aryl bromide.

| Ex. No. | Structure | Chemical Name | Exact Mass [M + H]+ |
|---|---|---|---|
| 31 | 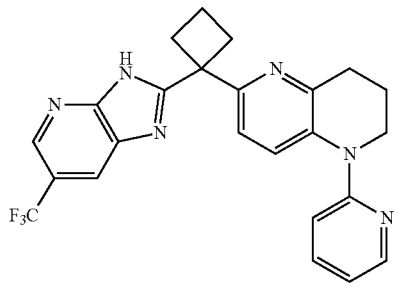 [SMILES: FC(F)(F)c1cnc2[nH]c(C3(c4ccc5c(n4)CCCN5c4ccccn4)CCC3)nc2c1] | 1-(pyridin-2-yl)-6-{1-[6-(trifluoromethyl)-3H-imidazo[4,5-b]pyridin-2-yl]cyclobutyl}-1,2,3,4-tetrahydro-1,5-naphthyridine | Calc'd 451, found 451 |

| Ex. No. | Structure | Chemical Name | Exact Mass [M + H]+ |
|---|---|---|---|
| 32 | 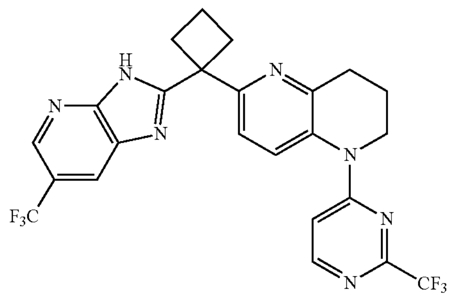 [SMILES: FC(F)(F)c1cnc2[nH]c(C3(c4ccc5c(n4)CCCN5c4ccnc(C(F)(F)F)n4)CCC3)nc2c1] | 6-{1-[6-(trifluoromethyl)-3H-imidazo[4,5-b]pyridin-2-yl]cyclobutyl}-1[2-(trifluoromethyl)pyrimidin-4-yl]-1,2,3,4-tetrahydro-1,5-naphthyridine | Calc'd 520, found 520 |
| 33 | 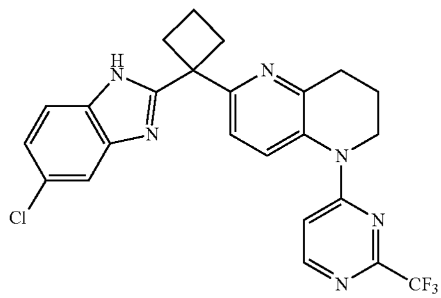 [SMILES: FC(F)(F)c1nccc(N2CCCc3nc(C4(c5nc6cc(Cl)ccc6[nH]5)CCC4)ccc32)n1] | 6-[1-(5-chloro-1H-benzimidazol-2-yl)cyclobutyl]-1-[2-(trifluoromethyl)pyrimidin-4-yl]-1,2,3,4-tetrahydro-1,5-naphthyridine | Calc'd 485, found 485 |
| 34 | 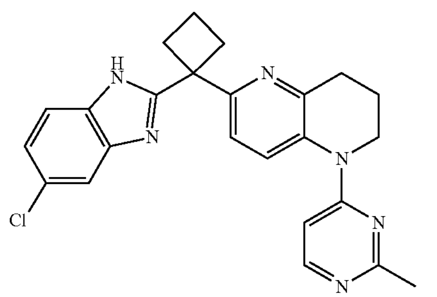 [SMILES: Cc1nccc(N2CCCc3nc(C4(c5nc6cc(Cl)ccc6[nH]5)CCC4)ccc32)n1] | 6-[1-(6-chloro-1H-benzimidazol-2-yl)cyclobutyl]-1-(2-methylpyrimidin-4-yl)-1,2,3,4-tetrahydro-1,5-naphthyridine | Calc'd 431, found 431 |
| 35 | 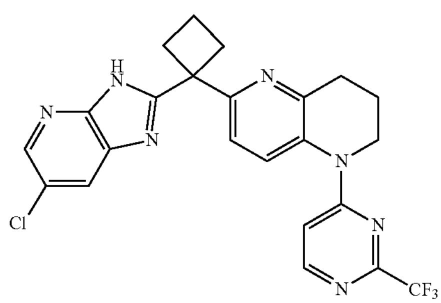 [SMILES: FC(F)(F)c1nccc(N2CCCc3nc(C4(c5nc6cc(Cl)cnc6[nH]5)CCC4)ccc32)n1] | 6-[1-(6-chloro-3H-imidazo[4,5-b]pyridin-2-yl)cyclobutyl]-1-[2-(trifluoromethyl)pyrimidin-4-yl]-1,2,3,4-tetrahydro-1,5-naphthyridine | Calc'd 486, found 486 |
| 36 | 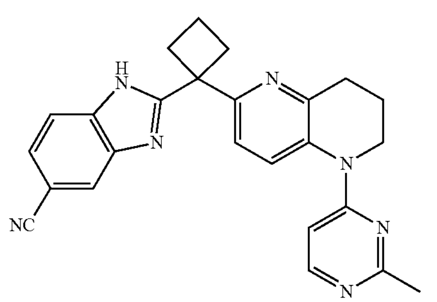 [SMILES: Cc1nccc(N2CCCc3nc(C4(c5nc6cc(C#N)ccc6[nH]5)CCC4)ccc32)n1] | 2-{1-[5-(2-methylpyrimidin-4-yl)-5,6,7,8-tetrahydro-1,5-naphthyridin-2-yl]cyclobutyl}-1H-benzimidazole-6-carbonitrile | Calc'd 422, found 422 |

Example 37: 2-(1-(5-(2-methylpyrimidin-4-yl)-5,6,7,8-tetrahydro-1,5-naphthyridin-2-yl)cyclopropyl)-1H-benzo[d]imidazole-6-carbonitrile (Ex. 37)

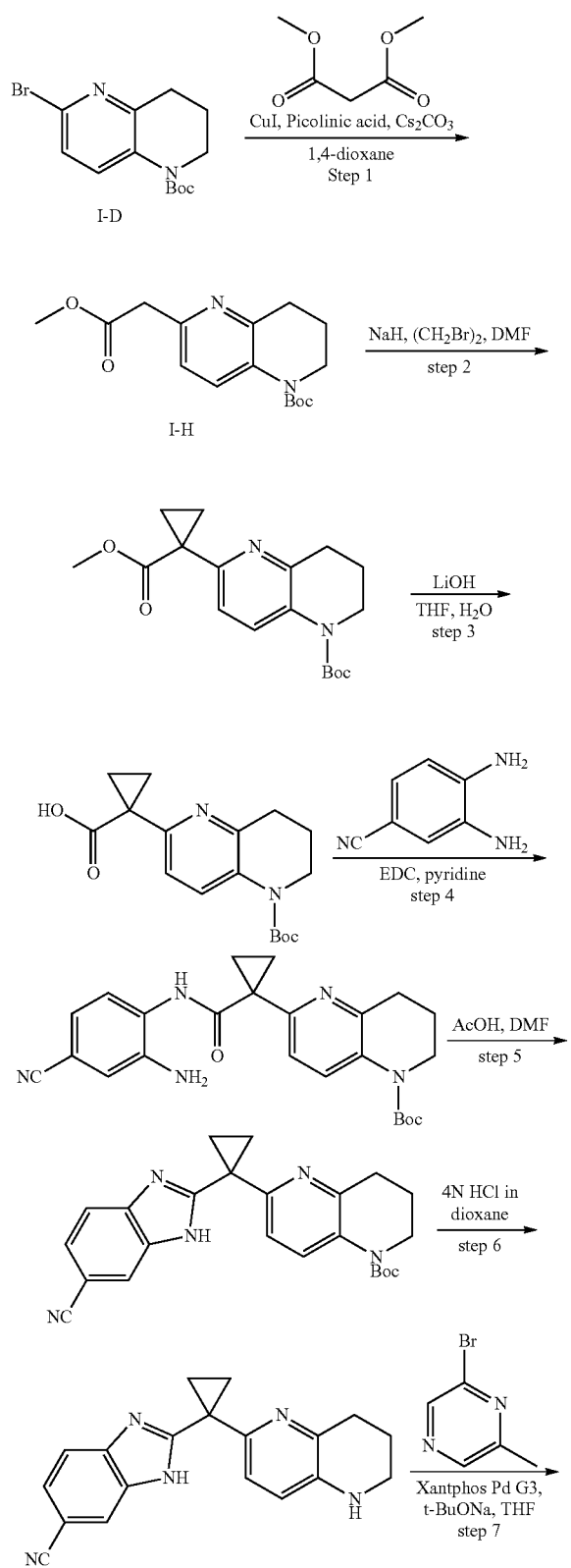

-continued

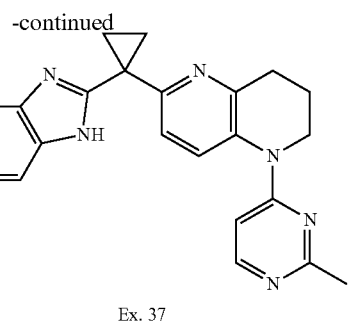

Ex. 37

Step 1. tert-butyl 6-(2-methoxy-2-oxoethyl)-3,4-dihydro-1,5-naphthyridine-1(2H)-carboxylate (I-H)

To a solution of I-D (10.0 g, 31.9 mmol) and picolinic acid (3.14 g, 25.5 mmol) in 1,4-dioxane (100 mL) were added copper(I) iodide (0.61 g, 3.2 mmol) and $Cs_2CO_3$ (31.2 g, 96.0 mmol) at rt. After the addition, dimethyl malonate (16.9 g, 128 mmol) was added to the solution at rt. Then the mixture was stirred at 100° C. for 16 h. The reaction was cooled to rt, diluted with EtOAc and filtered. The filtrate was concentrated in vacuo to afford residue, which was purified by column chromatography on silica gel (EtOAc in petroleum ether: 0-15% gradient) to afford tert-butyl 6-(2-methoxy-2-oxoethyl)-3,4-dihydro-1,5-naphthyridine-1(2H)-carboxylate (I-H). MS (EI) m/z 307 [M+H]+.

Step 2: tert-butyl 6-(1-(methoxycarbonyl)cyclopropyl)-3,4-dihydro-1,5-naphthyridine-1(2H)-carboxylate To a stirred solution of I-H (7.00 g, 22.8 mmol) in DMF (50 mL) was added NaH (2.74 g, 68.5 mmol) and 1,2-dibromoethane (8.58 g, 45.7 mmol) at 0° C. The mixture was stirred at 0° C. for 3 h. Then the reaction was quenched with water, extracted with EtOAc. The combined organic layers were washed with brine, dried over $Na_2SO_4$, filtered and concentrated in vacuo to afford residue, which was purified by column chromatography on silica gel (EtOAc in petroleum ether: 0-40% gradient) to afford tert-butyl 6-(1-(methoxycarbonyl)cyclopropyl)-3,4-dihydro-1,5-naphthyridine-1(2H)-carboxylate. MS (EI) m/z 333 [M+H]+.

Step 3: 1-(5-(tert-butoxycarbonyl)-5,6,7,8-tetrahydro-1,5-naphthyridin-2-yl)cyclopropane-1-carboxylic acid To a stirred solution of tert-butyl 6-(1-(methoxycarbonyl)cyclopropyl)-3,4-dihydro-1,5-naphthyridine-1(2H)-carboxylate (1.0 g, 3.0 mmol) in THF (5 mL) and water (2.5 mL) was added LiOH (0.360 g, 15.0 mmol) at rt. The mixture was stirred at rt for 16 h, adjusted to pH-5 with citric acid (sat.) and extracted with DCM. The combined organic layers were washed with brine, dried over $Na_2SO_4$, filtered and concentrated in vacuo to afford the crude product 1-(5-(tert-butoxycarbonyl)-5,6,7,8-tetrahydro-1,5-naphthyridin-2-yl)cyclopropanecarboxylic acid, which was used in the next step without any further purification. MS (EI) m/z 319 [M+H]+.

Step 4: tert-butyl 6-(1-((2-amino-4-cyanophenyl)carbamoyl)cyclopropyl)-3,4-dihydro-1,5-naphthyridine-1(2H)-carboxylate To a stirred solution of 1-(5-(tert-butoxycarbonyl)-5,6,7,8-tetrahydro-1,5-naphthyridin-2-yl)cyclopropanecarboxylic acid (1.0g, 3.1 mmol) in pyridine (10 mL) were added EDC (1.20 g, 6.28 mmol) and 3,4-diaminobenzonitrile (0.502 g, 3.77 mmol) at rt. The mixture was stirred at rt for 16 h. The solvent was removed in vacuo. The residue was diluted with water, extracted with EtOAc. The combined organic layers were washed with brine, dried over $Na_2SO_4$, filtered and concentrated in vacuo to afford residue which was purified by column chromatography on silica gel (EtOAc in petroleum ether: 0-50% gradient) to afford tert-butyl 6-(1-((2-amino-4-cyanophenyl)carbamoyl)cyclopropyl)-3,4-dihydro-1,5-naphthyridine-1(2H)-carboxylate. MS (EI) m/z 434 [M+H]+.

Step 5: tert-butyl 6-(1-(6-cyano-1H-benzo[d]imidazol-2-yl)cyclopropyl)-3,4-dihydro-1,5-naphthyridine-1(2H)-carboxylate To a stirred solution of tert-butyl 6-(1-((2-amino-4-cyanophenyl)carbamoyl)cyclopropyl)-3,4-dihydro-1,5-naphthyridine-1(2H)-carboxylate (100 mg, 0.231 mmol) in DMF (4 mL) was added acetic acid (1.0 mL, 0.23 mmol) at rt. After the addition was finished, the reaction was stirred at 130° C. for 16 h. The solvent was removed in vacuo. The residue was diluted with $NaHCO_3$ (sat.), extracted with EtOAc. The combined organic layers were washed with brine, dried over $Na_2SO_4$, filtered and concentrated in vacuo to afford residue, which was purified by prep-TLC (petroleum ether: EtOAc=1:1) to give tert-butyl 6-(1-(6-cyano-1H-benzo[d]imidazol-2-yl)cyclopropyl)-3,4-dihydro-1,5-naphthyridine-1(2H)-carboxylate. MS (EI) m/z 416 [M+H]+.

Step 6: 2-(1-(5,6,7,8-tetrahydro-1,5-naphthyridin-2-yl)cyclopropyl)-1H-benzo[d]imidazole-6-carbonitrile To a stirred solution of tert-butyl 6-(1-(6-cyano-1H-benzo[d]imidazol-2-yl)cyclopropyl)-3,4-dihydro-1,5-naphthyridine-1(2H)-carboxylate (60 mg, 0.14 mmol) in 1,4-dioxane (1 mL) was added HCl in dioxane (4 M, 1.5 mL, 6.0 mmol) at rt. The mixture was stirred at rt for 16 h. The solvent was evaporated in vacuo. The residue was diluted with $NaHCO_3$ (sat.), extracted with EtOAc. The combined organic layers were washed with brine, dried over $Na_2SO_4$, filtered and concentrated in vacuo to afford crude 2-(1-(5,6,7,8-tetrahydro-1,5-naphthyridin-2-yl)cyclopropyl)-1H-benzo[d]imidazole-6-carbonitrile. MS (EI) m/z 316 [M+H]+.

Step 7: 2-(1-(5-(2-methylpyrimidin-4-yl)-5,6,7,8-tetrahydro-1,5-naphthyridin-2-yl)cyclopropyl)-1H-benzo[d]imidazole-6-carbonitrile (Ex. 37)

To a stirred solution of 2-(1-(5,6,7,8-tetrahydro-1,5-naphthyridin-2-yl)cyclopropyl)-1H-benzo[d]imidazole-6-carbonitrile (60 mg, 0.19 mmol) in THF (2 mL) was added XantPhos Pd G3 precatalyst (30 mg, 0.032 mmol), 4-bromo-2-methylpyrimidine (30 mg, 0.233 mmol) and t-BuONa (45 mg, 0.47 mmol) at rt. After the addition was finished, the reaction was stirred at 60° C. under $N_2$ atmosphere for 16 h, then filtered. The filtrated was purified by reversed phase HPLC, eluting with water (0.1% TFA)-ACN to afford the title compound as a TFA salt (Ex. 37). $^1$H NMR (400 MHz, $CD_3OD$) δ8.17 (d, J=6.4 Hz, 1 H), 7.95-7.55 (m, 3 H), 7.54-7.50 (m, 1 H), 7.16 (d, J=8.4 Hz, 1 H), 6.92 (d, J=6.6 Hz, 1 H), 4.00-3.95 (m, 2 H), 2.96 (t, J=6.6 Hz , 2 H), 2.49 (s, 3 H), 2.12-2.05 (m, 2 H), 1.74 (brd, J=8.2 Hz, 4 H); MS (EI) m/z 408 [M+H]+.

Example 38-39 in the following table were prepared in an analogous fashion to Example 37, using the corresponding aryl diamines and corresponding aryl bromide.

| Ex. No. | Structure | Chemical Name | Exact Mass [M + H]+ |
|---|---|---|---|
| 38 | 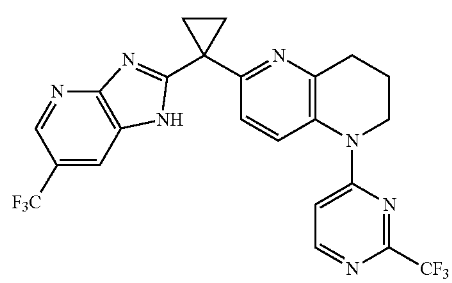 [SMILES: FC(F)(F)c1cnc2nc(C3(c4ccc5c(n4)CCCN5c4ccnc(C(F)(F)F)n4)CC3)[nH]c2c1] | 6-{1-[6-(trifluoromethyl)-3H-imidazo[4,5-b]pyridin-2-yl]cyclopropyl}-1-[2-(trifluoromethyl)pyrimidin-4-yl]-1,2,3,4-tetrahydro-1,5-naphthyridine | Calc'd 506, found 506 |
| 39 | 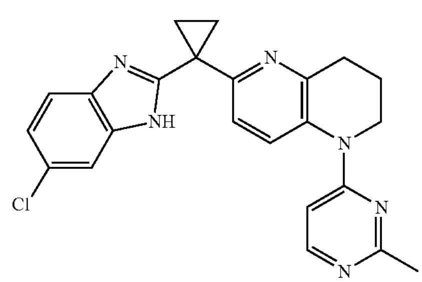 [SMILES: Cc1nccc(N2CCCc3nc(C4(c5nc6ccc(Cl)cc6[nH]5)CC4)ccc32)n1] | 6-[1-(6-chloro-1H-benzimidazol-2-yl)cyclopropyl]-1-(2-methylpyrimidin-4-yl)-1,2,3,4-tetrahydro-1,5-naphthyridine | Calc'd 417, found 417 |

Example 40: cyclopropyl 6-(5-(6-cyano-1H-benzo[d]imidazol-2-yl)spiro[2.3]hexan-5-yl)-3,4-dihydro-1,5-naphthyridine-1(2H)-carboxylate (Ex. 40)

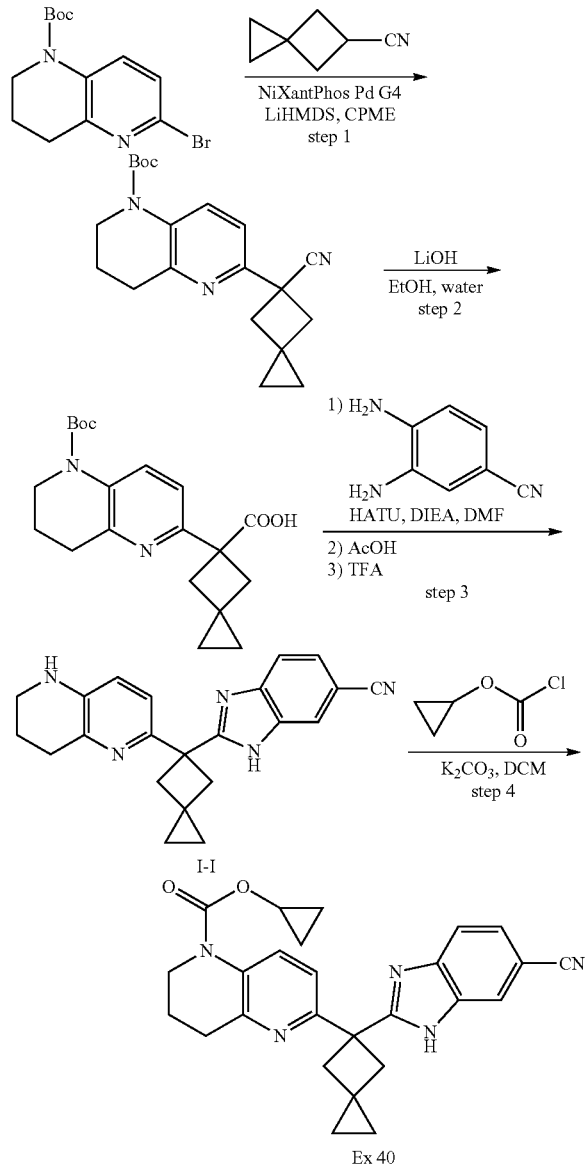

Step 1: tert-butyl 6-(5-cyanospiro[2.3]hexan-5-yl)-3,4-dihydro-1,5-naphthyridine-1(2H)-carboxylate A vial equipped with a stir bar was charged with NiXantPhos Pd G4 (119 mg, 0.130 mmol) and it was placed under nitrogen. To this vial was added tert-butyl 6-bromo-3,4-dihydro-1,5-naphthyridine-1(2H)-carboxylate (500 mg, 1.60 mmol) in 5 ml of CPME. Then spiro[2.3]hexane-5-carbonitrile (205 mgs, 1.92 mmol) was added followed by the dropwise addition of LiHMDS in THF (1M, 2.08 ml, 2.08 mmol). This mixture was stirred at rt for 1 h, quenched with NH$_4$Cl (sat.) and filtered. The filtrate was concentrated in vacuo, purified by column chromatography on silica gel (using hexanes and ethyl acetate as eluent) to give tert-butyl 6-(5-cyanospiro[2.3]hexan-5-yl)-3,4-dihydro-1,5-naphthyridine-1(2H)-carboxylate. MS (EI) m/z 340 [M+H$^+$].

Step 2: 5-(5-(tert-butoxycarbonyl)-5,6,7,8-tetrahydro-1,5-naphthyridin-2-yl)spiro[2.3]hexane-5-carboxylic acid A vial equipped with a stir bar was charged with tent-butyl 6-(5-cyanospiro[2.3]hexan-5-yl)-3,4-dihydro-1,5-naphthyridine-1(2H)-carboxylate (515 mg, 1.52 mmol), 2.5 ml of ethanol and 2.5 ml of water. Then lithium hydroxide (254 mg, 10.6 mmol) was added. The mixture was heated to 65° C. for 96 h. The reaction was then cooled to rt and adjusted to pH~2 with 1M HCl, extracted with EtOAc. The combined organic layers were washed with brine, dried over MgSO$_4$, filtered and concentrated in vacuo to give 5-(5-(tert-butoxycarbonyl)-5,6,7,8-tetrahydro-1,5-naphthyridin-2-yl)spiro[2.3]hexane-5-carboxylic acid. MS (EI) m/z 359 [M+H]$^+$.

Step 3: 2-(5-(5,6,7,8-tetrahydro-1,5-naphthyridin-2-yl)spiro[2.3]hexan-5-yl)-1H-benzo[d]imidazole-6-carbonitrile (I-I)

5-(5-(tert-butoxycarbonyl)-5,6,7,8-tetrahydro-1,5-naphthyridin-2-yl)spiro[2.3]hexane-5-carboxylic acid (220 mg, 0.610 mmol), 3,4-diaminobenzonitrile (98 mg, 0.74 mmol), and HATU (583 mg, 1.53 mmol) were added to a vial. To this vial was added DMF (3 mL), followed by DIEA (0.500 ml, 2.86 mmol). The reaction mixture heated to 100° C. for 20 h. The solvent was evaporated in vacuo and the residue was purified by column chromatography (Isco CombiFlash system, using hexanes and ethyl acetate as eluent) to afford tert-butyl 6-(5-((2-amino-5-cyanophenyl)carbamoyl)spiro[2.3]hexan-5-yl)-3,4-dihydro-1,5-naphthyridine-1(2H)-carboxylate. This amine addition intermediate was then dissolved in 2 ml of acetic acid and heated to 100° C. for 2 h. Then the mixture was cooled to rt and then 1 ml of TFA was added, and it was stirred for 1 h. The mixture was then evaporated in vacuo to afford 2-(5-(5,6,7,8-tetrahydro-1,5-naphthyridin-2-yl)spiro[2.3]hexan-5-yl)-1H-benzo[d]imidazole-6-carbonitrile as a TFA salt. MS (EI) m/z 356 [M+H]$^+$.

Step 4: cyclopropyl 6-(5-(6-cyano-1H-benzo[d]imidazol-2-yl)spiro[2.3]hexan-5-yl)-3,4-dihydro-1,5-naphthyridine-1(2H)-carboxylate (Ex. 40)

The I-I (75 mg, 0.21 mmol) and potassium carbonate (146 mg, 1.06 mmol) were added to a vial with DCM (2 mL). To this vial was added cyclopropyl carbonochloridate (102 mg, 0.840 mmol). The mixture was stirred at rt for 12 h. The solvent was evaporated in vacuo. This residue was then dissolved in ethanol and water (1 mL, 1:1) and lithium hydroxide (9.2 mg, 0.38 mmol) was added and it was stirred for 1 h at rt. The reaction mixture was filtered and purified by reversed phase HPLC, eluting with water (0.1% TFA)-ACN to afford the title compound as a TFA salt (Ex. 40). $^1$H NMR (600 MHz, DMSO-d6) δ8.08 (br s, 1H), 8.06-7.98 (m, 1H), 7.67 (d, J=8.3 Hz, 1H), 7.59 (d, J=8.3 Hz, 1H), 7.26 (d, J=8.6 Hz, 1H), 4.09-4.03 (m, 1H), 3.66-3.59 (m, 2H), 3.08-2.97 (m, 4H), 2.85-2.79 (m, 2H), 1.91-1.80 (m, 2H), 0.68-0.63 (m, 4H), 0.44 -0.39 (m, 4H); MS (EI) m/z 440 [M+H]$^+$.

Example 41: 2-(5-(5-(2-(trifluoromethyl)pyrimidin-4-yl)-5,6,7,8-tetrahydro-1,5-naphthyridin-2-yl)spiro[2,3]hexan-5-yl)-1H-benzo[d]imidazole-6-carbonitrile (Ex. 41)

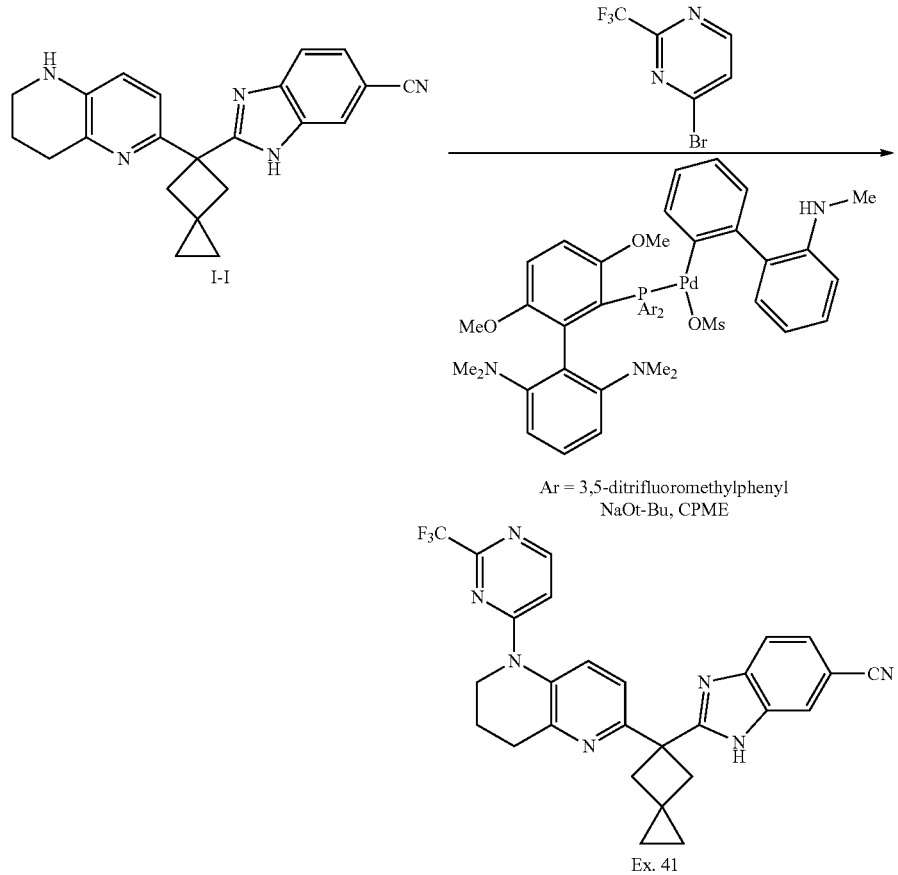

The I-I (45 mg, 0.13 mmol) and Methanesulfonato(2-bis(3,5-di(trifluoromethyl)phenylphosphino)-3,6-dimethoxy-2',6'-bis(dimethylamino)-1,1'-biphenyl)(2'-methylamino-1,1'-biphenyl-2-yl)palladium(II) (22 mg, 0.019 mmol) and 4-bromo-2-trifluoromethylpyrimidine (34.5 mg, 0.150 mmol) and sodium tert-butoxide (18 mg, 0.19 mmol) were all added to a vial equipped with a stir bar. To this vial was added CPME (0.75 ml). The mixture was then heated to 95° C. for 15 h, then cooled down to rt and filtered. The filtrate was evaporated in vacuo and purified by reversed phase HPLC, eluting with water (0.1%TFA)-ACN to afford the title compound as a TFA salt (Ex. 41). $^1$H NMR (600 MHz, DMSO-$d_6$) δ8.46 (d, J=6.1 Hz, 1H), 8.09 (br s, 1H), 8.00 (d,J==8.5 Hz, 1H), 7.69 (d, J=8.3 Hz, 7.60 (d, J=8.3 Hz, 1H), 7.30-7.22 (m, 2H), 3.90-3.84 (m, 2H), 3.10-3.03 (m, 4H), 2.90-2.84 (m, 2H), 2.01-1.95 (m, 2H), 0.47-0.39 (m, 4H). MS (EI) m/z 502 [M+H]$^+$.

BIOLOGICAL ASSAYS

IDO1 Cellular Assay in HeLa Cells Stimulated with IFNγ

HeLa cells were cultured in complete HeLa culture medium (90% EMEM, 10% heat-inactivated fetal bovine serum) and expanded to about 1×10$^9$ cells. The cells were then collected and frozen down at 10×106 cells/vial in 1 mL frozen medium (90% complete HeLa culture medium, 10% DMSO).

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen HeLa cells were thawed and transferred into HeLa assay medium (99% complete HeLa culture medium, 1% Pen/Strep) with 20 mL medium/vial of cells. The cells were spun down at 250 g in a table top centrifuge for 5 min and suspended in same volume of HeLa assay medium. The cells were then counted and adjusted to a density of 2×105 cells/mL in HeLa assay medium. Sterile L-tryptophan were added to the cells with final concentration of 300 uM L-tryptophan. A small aliquot (2 mL/plate) of HeLa cells were set aside and were not treated with IFNγ, to serve as the Max-E control. The rest of HeLa cells were added with sterile IFNγ (Cat# 285-IF, R & D systems) with a final concentration of 100 ng/mL.

HeLa cells with and without IFNγ were dispensed to the respective wells of 384-well assay plates containing the compounds. The plates were incubated for about 48 hours at a 37° C., 5% CO2 incubator. Afterwards, 12 μL of 0.5 M methyl isonipecotate in dimethyl sulfoxide were added into each well and the plates were sealed and incubated at 37° C.

without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Specific $IC_{50}$ activity data for the exemplified compounds disclosed herein is provided in the following table.

| Ex. No. | IDO1 HeLa Cell Assay, IC50 (nM) |
|---|---|
| 1 | 3.867 |
| 2 | 2.919 |
| 3 | 2.452 |
| 4 | 5.258 |
| 5 | 2.741 |
| 6 | 4.26 |
| 7 | 15.32 |
| 8 | 4.458 |
| 9 | 63.41 |
| 10 | 4.228 |
| 11 | 4.879 |
| 12 | 10.46 |
| 13 | 1.681 |
| 14 | 1.577 |
| 15 | 2.141 |
| 16 | 1.741 |
| 17 | 0.9583 |
| 18 | 1.978 |
| 19 | 1.796 |
| 20 | 4.245 |
| 21 | 0.6928 |
| 22 | 1.375 |
| 23 | 1.349 |
| 24 | 3.285 |
| 25 | 1.147 |
| 26 | 0.9819 |
| 27 | 2.289 |
| 28 | 4.469 |
| 29 | 2.48 |
| 30 | 4.365 |
| 31 | 3.335 |
| 32 | 12.95 |
| 33 | 3.408 |
| 34 | 2.919 |
| 35 | 2.693 |
| 36 | 1.938 |
| 37 | 4.813 |
| 38 | 12.51 |
| 39 | 9.146 |
| 40 | 2.824 |
| 41 | 3.177 |

IDO1 Human Whole Blood Assay

Compounds to be tested were serially diluted in ten 3-fold steps in DMSO starting from 10 mM. 3 μL of compound dilutions or DMSO alone were then dispensed from the dilution plate into a polypropylene 96-well assay plate containing 97 μL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. 240 μL of blood was transferred to each of the wells of a v-bottom 96 well plate. 30 μL of compound was transferred from intermediate dilution plate, and incubated for 15 min. 30 μL from stimulants was then transferred to blood and mixed thoroughly. Plate was covered with breathable membrane and incubated at 37° C. for overnight (18 h).

On day 2 isotope labeled standard of kynurenine and tryptophan was made in water at 10×concentration and 30 μL was added to the blood at 3 μM final concentration. The assay plates were centrifuged at 300×G for 10 min with no brake to separate plasma from red blood cells. 60 μL of plasma samples was removed without disturbing red blood cells. Plasma was diluted with RPMI in 1:1 ratio and proteins were precipitated out with two volumes of Acetonitrile. The plates were centrifuged at 4000×G for 60 min. 20 μL of supernatant was carefully transferred to a 384 well plate contain 40 μL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadrupole MS/MS instrument. For each sample, 5 μL were injected onto an Atlantis T3 column (2.1 mm×150 mm, 3 μm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. No. | Human whole blood assay, IC50(nM) |
|---|---|
| 1 | 185.9 |
| 2 | 132.3 |
| 3 | 30.67 |
| 4 | 27.02 |
| 5 | 228.6 |
| 13 | 56.34 |
| 15 | 26.13 |
| 16 | 14.08 |
| 17 | 47.79 |
| 18 | 494.4 |
| 19 | 274.4 |
| 20 | 35 |

-continued

| Ex. No. | Human whole blood assay, IC50(nM) |
|---|---|
| 21 | 44.12 |
| 22 | 60.45 |
| 23 | 64.18 |
| 24 | 120.7 |
| 25 | 117.5 |
| 26 | 55.02 |
| 27 | 56.81 |
| 30 | 354.7 |
| 33 | 83.29 |
| 34 | 139.8 |
| 35 | 53.91 |
| 39 | 10000 |
| 41 | 71.3 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I),

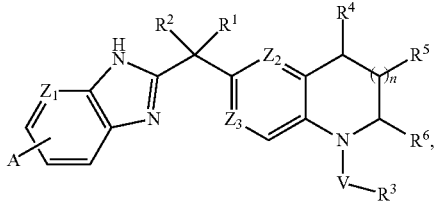

or a pharmaceutically acceptable salt thereof, wherein:
A is selected from H, halogen, CN, and $C_{1-6}$alkyl optionally substituted with 1-3 halogens;
$Z_1$, $Z_2$ and $Z_3$ are each independently selected from $CR^8$ and N;
$R^8$, if present, is H, halogen, $C_{1-6}$alkyl, $OC_{0-6}$alkyl, or $NH_2$;
$R^1$ and $R^2$ are independently selected from H, $C_{1-6}$ alkyl, and $C_{3-6}$ cycloalkyl, optionally substituted with $C_{3-6}$cycloalkyl, or $R^1$ and $R^2$, together with the carbon atom to which they are attached, optionally form $C_{3-6}$cycloalkyl optionally substituted with $C_{3-6}$cycloalkyl;
V is selected from C(O), CONH, and $C_{3-6}$ heterocycle containing 1-4 nitrogen, wherein the $C_{3-6}$ heterocycle is optionally substituted with $CH_3$ or $CF_3$;
$R^3$ is selected from H, $C_{1-6}$ alkyl, $C_{3-6}$cycloalkyl, $OC_{1-6}$-(alkyl, $OC_{3-6}$cycloalkyl, $C_{3-10}$heterocyclyl containing 1-4 nitrogen or oxygen, optionally substituted with halogen, $C_{1-6}$alkyl or $CF_3$, and phenyl optionally substituted with halogen;
$R^4$ and $R^5$ are each independently selected from H, OH, halogen, and $C_{1-6}$alkyl;
$R^6$ is independently selected from H, OH, halogen, and $C_{1-6}$alkyl;
and n is 0, 1, 2, 3, or 4.

2. The compound of claim 1, or a pharmaceutically acceptable salt thereof, wherein A is selected from the group consisting of H, $CF_3$, $CH_3$, CN, or and Cl.

3. The compound of claim 1, or a pharmaceutically acceptable salt thereof, wherein $Z_1$ is CH.

4. The compound of claim 1 or a pharmaceutically acceptable salt thereof, wherein $Z_1$ is N.

5. The compound of claim 1, or a pharmaceutically acceptable salt thereof, wherein $Z_2$ is CH.

6. The compound of any of claim 1, or a pharmaceutically acceptable salt thereof, wherein $Z_2$ is N.

7. The compound of claim 1, or a pharmaceutically acceptable salt thereof, wherein V is C (O).

8. The compound of claim 1, or a pharmaceutically acceptable salt thereof, wherein both $R^1$ and $R^2$ are independently selected from H and $CH_3$, or together with the carbon atom to which they are attached, optionally form $C_{3-6}$cycloalkyl optionally substituted with $C_{3-6}$cycloalkyl.

9. The compound of claim 1, or a pharmaceutically acceptable salt thereof wherein $R^3$ is selected from H, $C_{1-6}$ alkyl, $C_{3-6}$cycloalkyl, $OC_{1-6}$alkyl, $OC_{3-6}$cycloalkyl, and $C_{3-10}$ heterocyclyl containing 1-4 nitrogen or oxygen, optionally substituted with halogen, $C_{1-6}$alkyl or $CF_3$.

10. The compound of claim 1, or a pharmaceutically acceptable salt thereof, wherein $R^3$ is selected from H, $CH_3$, cyclopropyl, tetrahydrofuran, $OCH_3$, O-cyclopropyl, terahydropyran, $OCH_2CH_3$, of and phenyl optionally substituted with halogen.

11. A compound of formula Ia:

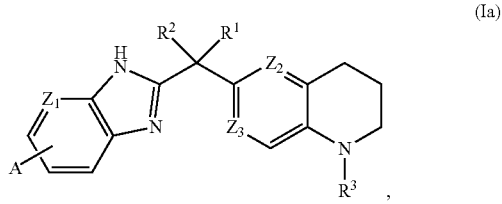

or a pharmaceutically acceptable salt thereof, wherein:
A is selected from H, halogen, CN, $CH_3$, and $CF_3$;
$Z_1$, $Z_2$, and $Z_3$ are each independently selected from CH and N;
$R^1$ and $R^2$ together with the carbon atom to which they are attached form a $C_{3-6}$cycloalkyl, wherein the cycloalkyl is optionally substituted with $C_{3-6}$cycloalkyl; and
$R^3$ is selected from H, $C_{1-6}$ alkyl, $C_{3-6}$cycloalkyl, $OC_{1-6}$alkyl, $OC_{3-6}$cycloalkyl, and $C_{3-10}$ heterocyclyl containing 1-4 nitrogen or oxygen, optionally substituted with halogen, $C_{1-6}$alkyl or $CF_3$.

12. The compound of claim 1 of formula Ib:

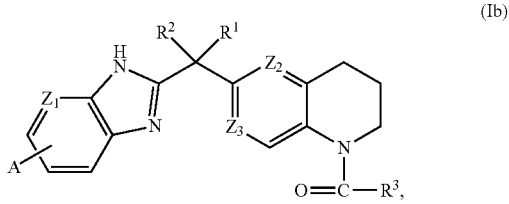

or a pharmaceutically acceptable salt thereof, wherein:
A is selected from H, halogen, CN, $CH_3$, and $CF_3$;
$Z_1$, $Z_2$, and $Z_3$ are each independently selected from CH and N;
$R^1$ and $R^2$ are independently selected from H, $CH_3$, and $C_{3-6}$cycloalkyl, wherein the cycloalkyl is optionally substituted with $C_{3-6}$cycloalkyl, or $R^1$ and $R^2$; together with the carbon atom to which they are attached, optionally form C$_{3-6}$cycloalkyl, wherein the cycloalkyl is optionally substituted with C$_{3-6}$cycloalkyl; and R$^3$ is selected from H, C$_{1-6}$ alkyl, C$_{3-6}$cycloalkyl, OC$_{1-6}$alkyl, OC$_{3-6}$cycloalkyl, and C$_{3-10}$ heterocyclyl containing 1-4 nitrogen or oxygen, optionally substituted with halogen, C$_{1-6}$alkyl or CF$_3$.

13. The compound of claim 1 of formula Ic:

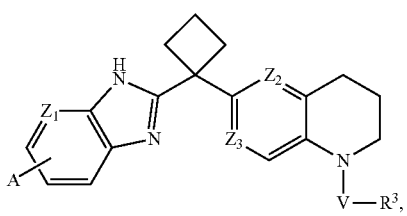

(Ic)

or a pharmaceutically acceptable salt thereof, wherein:
A is selected from H, halogen, CN, CH$_3$, and CF$_3$;
Z$_1$, Z$_2$, and Z$_3$ are each independently selected from CH and N;
V is C (O); and
R$^3$ is selected from H, C$_{1-6}$ alkyl, C$_{3-6}$cycloalkyl, OC$_{1-6}$alkyl, OC$_{3-6}$cycloalkyl, and C$_{3-10}$ heterocyclyl containing 1-4 nitrogen or oxygen, optionally substituted with halogen, C$_{1-6}$alkyl or CF$_3$.

14. The compound of claim 1 of formula If:

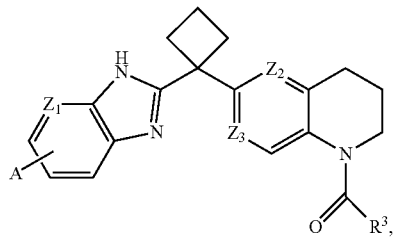

(If)

or a pharmaceutically acceptable salt thereof, wherein:
A is selected from H, halogen, CN, CH$_3$, and CF$_3$;
Z$_1$, Z$_2$, and Z$_3$ are each independently selected from CH and N; and
R$^3$ is selected from H, C$_{1-6}$ alkyl, C$_{3-6}$cycloalkyl, OC$_{1-6}$alkyl, OC$_{3-6}$cycloalkyl, and C$_{3-10}$ heterocyclyl containing 1-4 nitrogen or oxygen, optionally substituted with halogen, C$_{1-6}$alkyl or CF$_3$.

15. The compound of claim 1 of formula Ig:

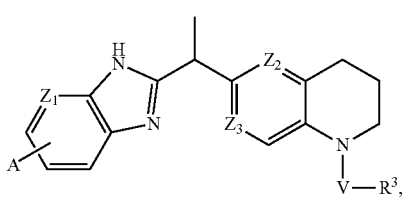

(Ig)

or a pharmaceutically acceptable salt thereof, wherein:
A is selected from H, halogen, CN, CH$_3$, and CF$_3$;
Z$_1$, Z$_2$, and Z$_3$ are each independently selected from CH and N;
V is C (O); and
R$^3$ is selected from H, C$_{1-6}$ alkyl, C$_{3-6}$cycloalkyl, OC$_{1-6}$alkyl, OC$_{3-6}$cycloalkyl, and C$_{3-10}$ heterocyclyl containing 1-4 nitrogen or oxygen, optionally substituted with halogen, C$_{1-6}$alkyl or CF$_3$.

16. A compound which is selected from:

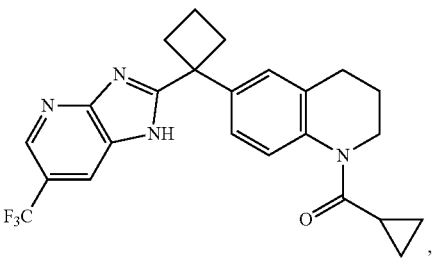

,

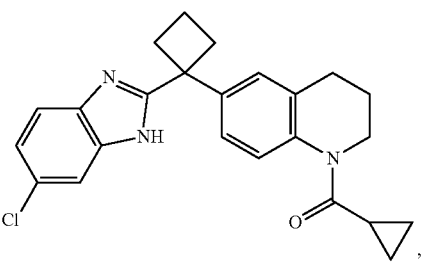

,

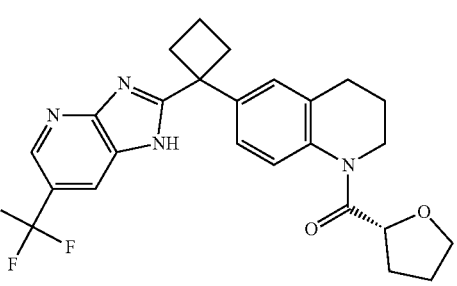

,

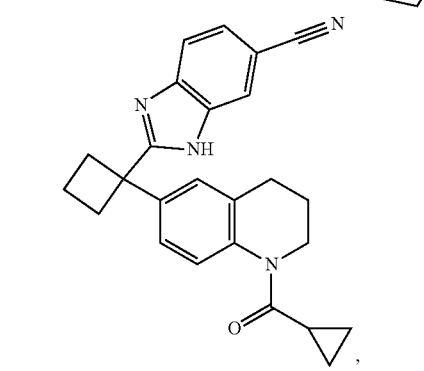

,

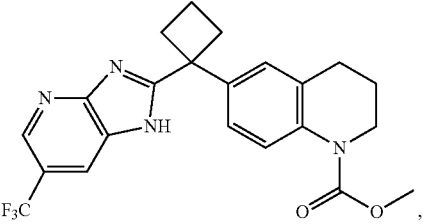

,

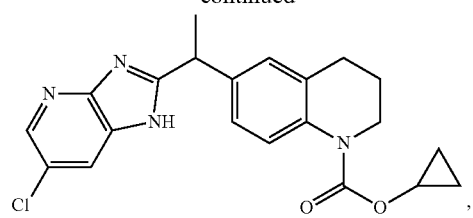,
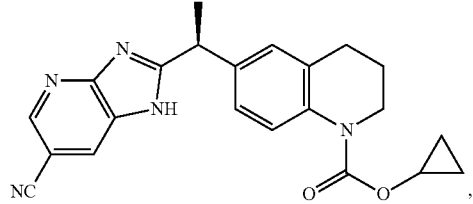,
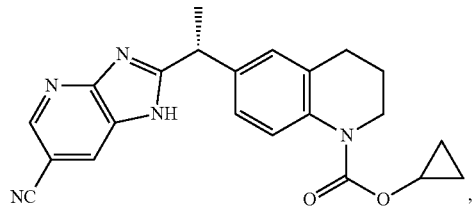,
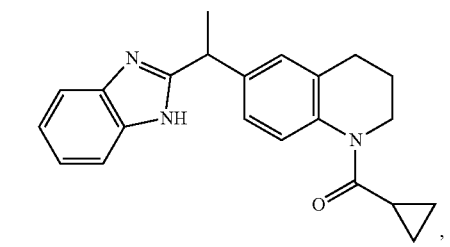,
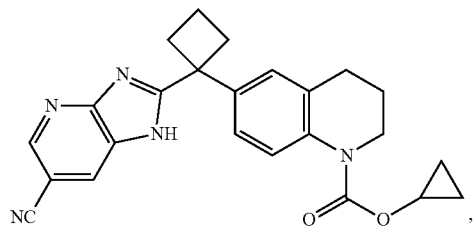,
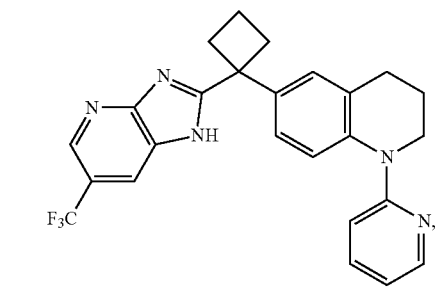,
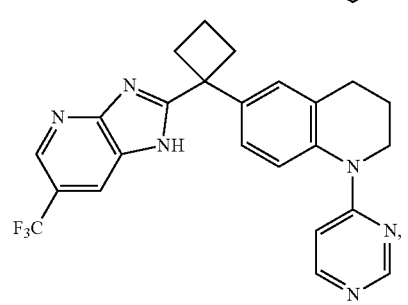,
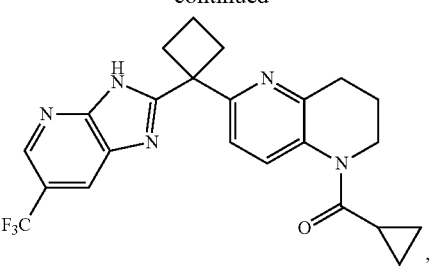,
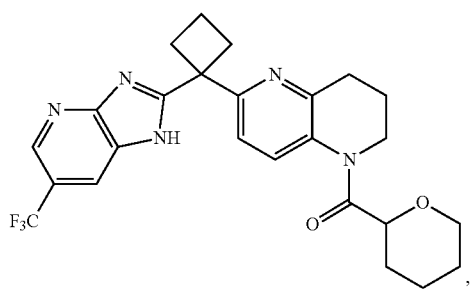,
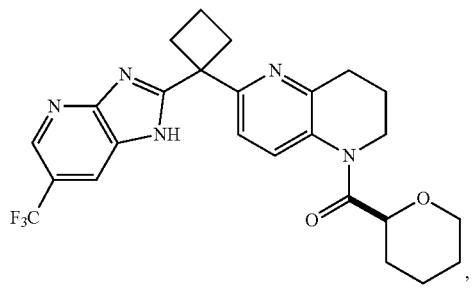,
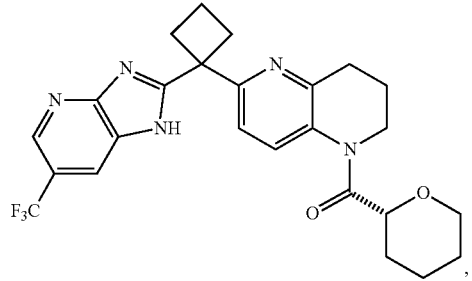,
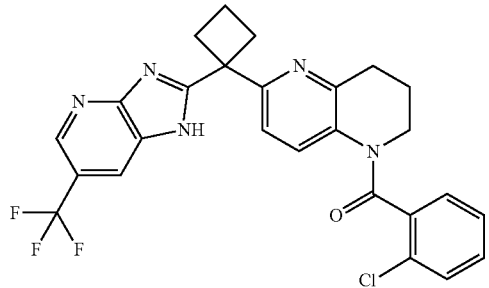,
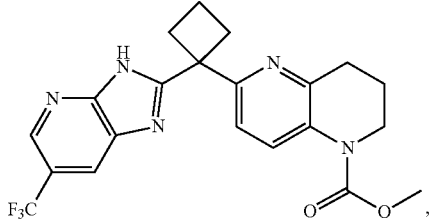, -continued
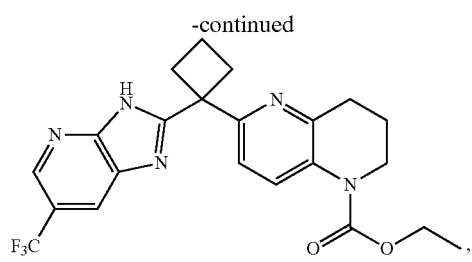
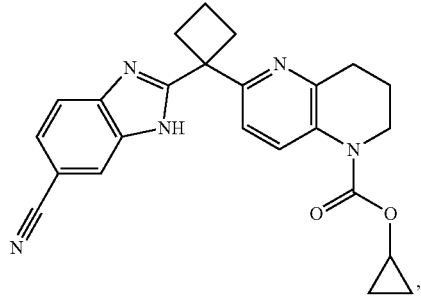
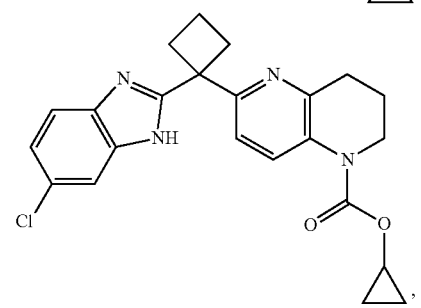
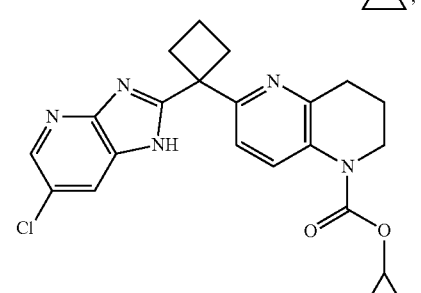
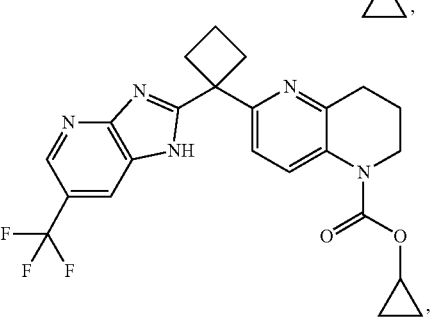
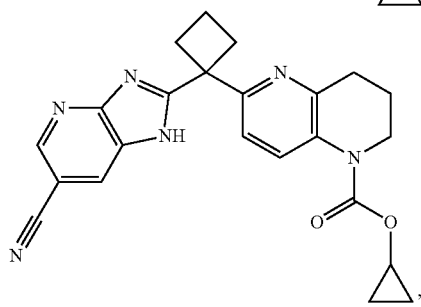
-continued
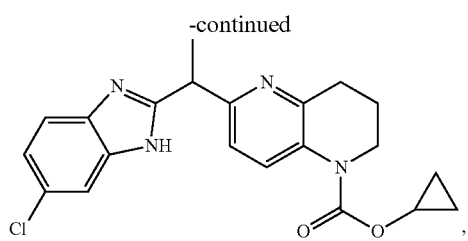
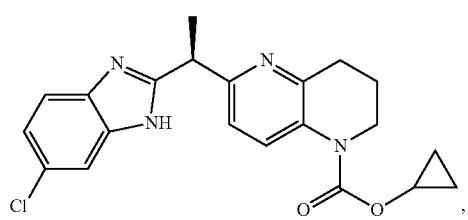
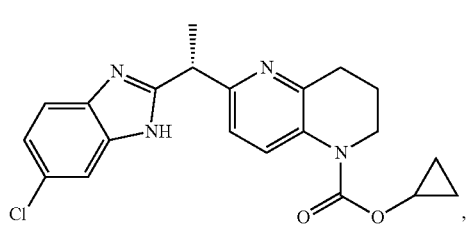
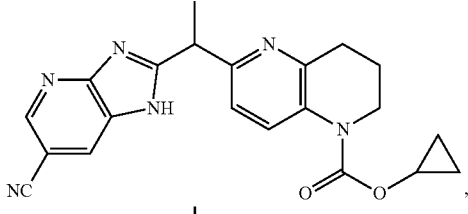
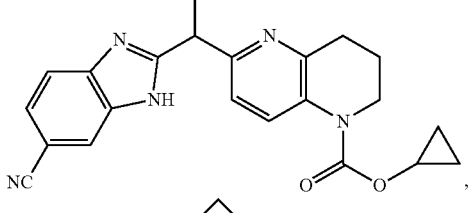
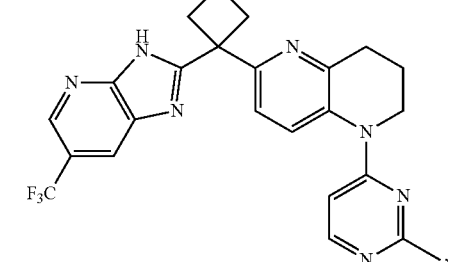
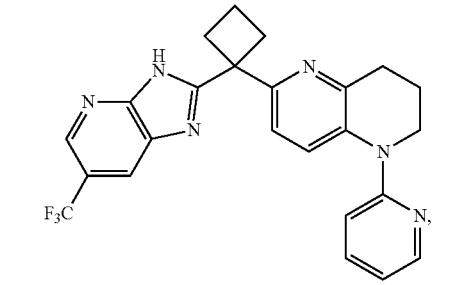

-continued

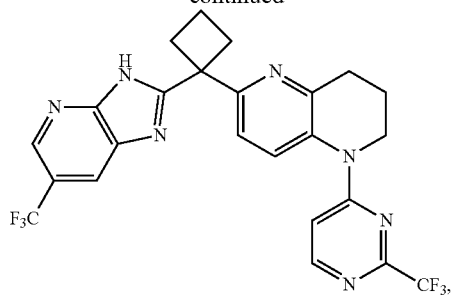
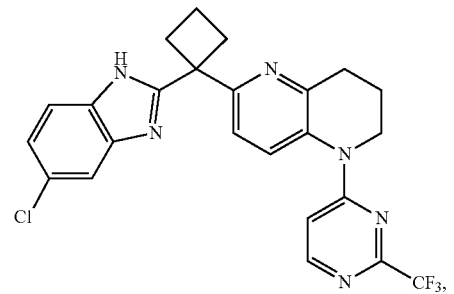
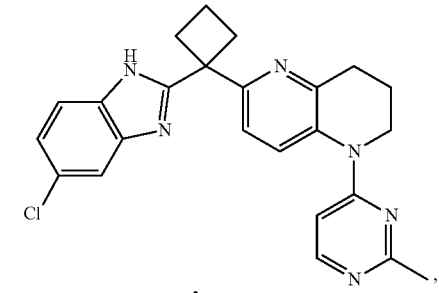
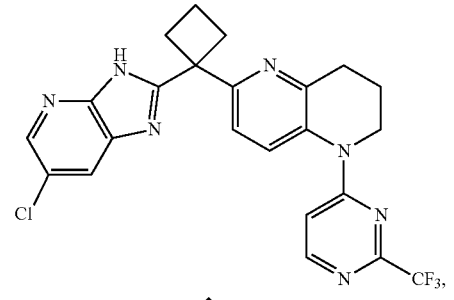
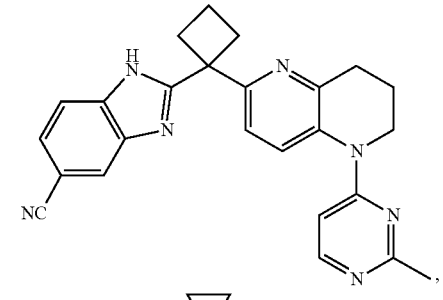
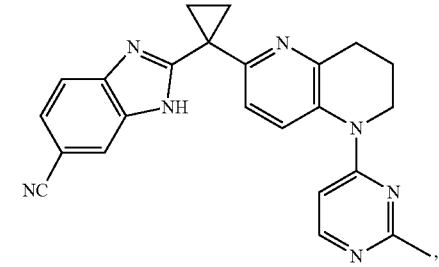

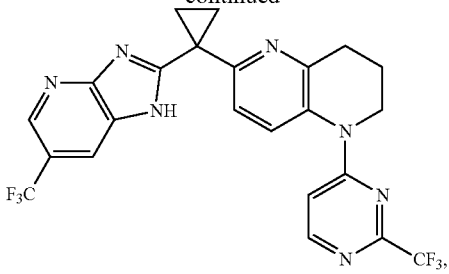
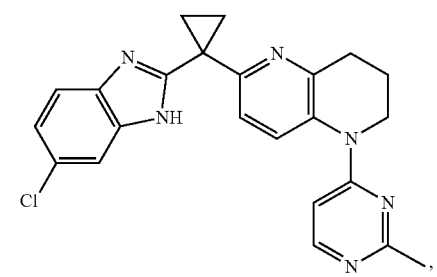
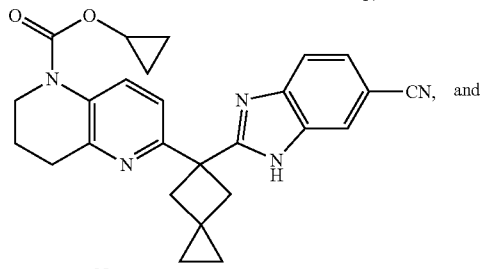
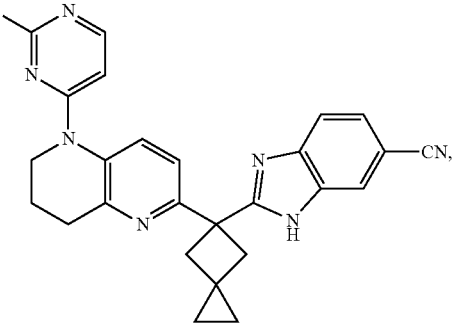

or a pharmaceutically acceptable salt thereof.

17. A composition which comprises an inert carrier and a compound of claim 1 or a pharmaceutically acceptable salt thereof.

18. A method for treating an IDO-associated disease or disorder in a mammalian subject which comprises administering to the subject an effective amount of a compound of claim 1 or a pharmaceutically acceptable salt thereof in combination with another anti-cancer agent.

19. The method of claim 18 wherein the IDO-associated disease or disorder is selected from cancer, viral infection, HCV infection, depression, neurodegenerative disorders, trauma, age-related cataracts, organ transplantation, and autoimmune diseases.

20. The compound of claim 1, or a pharmaceutically acceptable salt thereof, wherein n is 1.

* * * * *